(12) United States Patent
Glanville et al.

(10) Patent No.: US 11,021,531 B1
(45) Date of Patent: Jun. 1, 2021

(54) ANTI-SARS-COV-2 ANTIBODIES DERIVED FROM 2GHW

(71) Applicant: Centivax, Inc., South San Francisco, CA (US)

(72) Inventors: Jacob Glanville, San Francisco, CA (US); Shahrad Daraeikia, San Francisco, CA (US); I-Chieh Wang, San Bruno, CA (US); Sindy Andrea Liao-Chan, San Jose, CA (US); Jean-Philippe Bürckert, Belmont, CA (US); Sawsan Youssef, Menlo Park, CA (US)

(73) Assignee: Centivax, Inc., South San Francisco, CA (US)

( * ) Notice: Subject to any disclaimer, the term of this patent is extended or adjusted under 35 U.S.C. 154(b) by 0 days.

(21) Appl. No.: 15/931,643

(22) Filed: May 14, 2020

Related U.S. Application Data

(60) Provisional application No. 63/014,556, filed on Apr. 23, 2020, provisional application No. 63/014,058, filed on Apr. 22, 2020, provisional application No. 62/993,630, filed on Mar. 23, 2020.

(51) Int. Cl.
| | | |
|---|---|---|
| A61K 39/42 | (2006.01) | |
| C07K 16/10 | (2006.01) | |
| A61P 31/14 | (2006.01) | |
| A61K 39/00 | (2006.01) | |

(52) U.S. Cl.
CPC ............. *C07K 16/10* (2013.01); *A61K 39/42* (2013.01); *A61P 31/14* (2018.01); *A61K 2039/505* (2013.01); *C07K 2317/565* (2013.01); *C07K 2317/622* (2013.01); *C07K 2317/92* (2013.01)

(58) Field of Classification Search
None
See application file for complete search history.

(56) References Cited

PUBLICATIONS

Rudikoff et al., Proc Natl Acad Sci USA 1982 vol. 79 (Year: 1982).*
MacCallum et al. J. Mol. Biol. (1996) 262, 732-745 (Year: 1996).*
Tian et al. Emerging Microbes and Infections, 2020, 9: 382-385. Published online Feb. 17, 2020). (Year: 2020).*
Aiola, C. @Chrisaiola. Dr. Jake Glanville and I discuss what we can expect in the coming weeks, why COVID-19 is much more dangerous than seasonal influenza, and his team's continuing effort to bio-engineer antibodies. @CurlyJungleJake #coronavirus #COVID19 #pandemic (Tweet). Twitter (Mar. 16, 2020). Retrieved Jul. 30, 2020 from https://twitter.com/chrisaiola/status/1239707660896870402?s=20. One page.

(Continued)

*Primary Examiner* — Shanon A. Foley
*Assistant Examiner* — Myron G Hill
(74) *Attorney, Agent, or Firm* — Wilson Sonsini Goodrich & Rosati

(57) ABSTRACT

This disclosure provides antibodies and antigen-binding fragments that are derived from 2ghw and that can be administered to an individual that is infected or suspected of being infected with a virus. Antibodies and antigen-binding fragments provided herein can be capable of treating or curing the virus, and which may provide protection against the virus for up to several weeks. Antibodies and antigen-binding fragments provided herein can be used to diagnose a SARS-Cov-2 infection.

16 Claims, 1 Drawing Sheet
Specification includes a Sequence Listing.

| Virus | Antigen | Sequence | SEQ ID NO |
|---|---|---|---|
| MERS | 5gmq | VECDFSPLLSGTPPQVYNFKRLVFTNCNYNLTKLLSLFSVN DFTCSQISPAAIASNCYSSLILDYFSYPLSMKSDLSVSSAG PISQFNYKQSFSNPTCLILATVPHNLTTITKPLKYSYINKC SRLLSDDRTEVPQLVNANQYSPCVSIVPSTVWEDGDYYRKQ LSPLEGGGWLVASGSTVAMTEQLQMGFGITVQYGTDTNSVC PKL | 106 |
| 2019-nCoV | 2019-Wuhan-Hu-1 | RFPNITNLCPFGEVFNATRFASVYAWNRKRISNCVADYSVL YNSASFSTFKCYGVSPTKLNDLCFTNVYADSFVIRGDEVRQ IAPGQTGKIADYNYKLPDDFTGCVIAWNSNNLDSKVGGNYN YLYRLFRKSNLKPFERDISTEIYQACSTPCNGVEGFNCYFP LQSYGFQPTNGVGYQPYRVVVLSFELLHAPATVCGP | 107 |
| SARS | 2dd8_S spike glycoprotein | PNITNLCPFGEVFNATKFPSVYAWERKKISNCVADYSVLYN STFFSTFKCYGVSATKLNDLCFSNVYADSFVVKGDDVRQIA PGQTGVIADYNYKLPDDFMGCVLAWNTRNIDATSTGNYNYK YRYLRHCKLRPFERDISNVPFSPDGKPCTPPALNCYWPLND YGFYTTTGIGYQPYRVVVLSFELLNAPATVCGPKLSTD | 108 |
| SARS | QDF43825.1 | PNITNLCPFGEVFNATTFPSVYAWERKRISNCVADYSVLYN STSFSTFKCYGVSATKLNDLCFSNVYADSFVVKGDDVRQIA PGQTGVIADYNYKLPDDFMGCVLAWNTRNIDATSTGNYNYK YRSLRHGKLRPFERDISNVPFSPDGKPCTPPAFNCYWPLND YGFFTTNGIGYQPYRVVVLSFELLNAPATVCGPKLSTD | 109 |

(56) References Cited

PUBLICATIONS

Aiola, Chris. Dr. Jake Glanville—Mar. 15, 2020. YouTube video (transcript). Transcribed Sep. 16, 2020 from URL: https://www.youtube.com/watch?v=bEjk-bLVW_8&feature=youtu.be. Mar. 15, 2020. 6 pages.

Beeman. Netflix's 'Pandemic' Doctor Says He May Have Found a Treatment for Coronavirus. Heavy (Apr. 10, 2020). Retrieved Sep. 18, 2020 at URL: https://heavy.com/news/2020/04/jacob-glanville-netflix-pandemic-doctor-coronavirus/. 6 pages.

Centivax Antibodies Neutralize the Pandemic Coronavirus, Independently Confirmed by Three Research Laboratories (USAMRIID, Stanford, and UTMB/GNL). Business Wire (May 18, 2020). Retrieved Jul. 27, 2020 at URL: https://www.businesswire.com/news/home/20200518005767/en/Centivax-Antibodies-Neutralize-Pandemic-Coronavirus-Independently-Confirmed. 3 pages.
CNBC's Closing Bell. @CNBCClosingBell. .@distributedbio is developing a COVID-19 treatment using antibodies produced during the 2002 SARS outbreak. Founder & CEO Dr. @CurleyJungleJake joined us to talk more about the timeline and potential effectiveness of the treatment. (Tweet). Twitter (Apr. 21, 2020). Retrieved Jul. 30, 2020 from https://twitter.com/CNBCClosingBell/status/1252681883772694533?s=20. One page.
Cohen, J. @Sciencecohen. In parallel with vaccine race, 50+ groups are making a boatload of SARS-CoV-2 monoclonal antibodies from recovered patients like Dr. X, mice, SARS-CoV, and computer programs. Yes, access, production, and safety will be issues. But color me optimistic. https://sciencemag.org/news/2020/05/race-antibodies-stop-new-coronavirus (Tweet). Twitter (May 5, 2020). Retrieved Jul. 30, 2020 from https://twitter.com/sciencecohen/status/1257800751184633857?s=20. One page.
Cohen. The race is on for antibodies that stop the new coronavirus. Science (May 5, 2020). Retrieved Aug. 8, 2020 at URL: https://www.sciencemag.org/news/2020/05/race-antibodies-stop-new-coronavirus/. 10 pages.
Co-pending U.S. Appl. No. 15/931,642, filed May 14, 2020.
Co-pending U.S. Appl. No. 15/931,648, filed May 14, 2020.
Co-pending U.S. Appl. No. 15/931,649, filed May 14, 2020.
Co-pending U.S. Appl. No. 15/931,652, filed May 14, 2020.
Co-pending U.S. Appl. No. 15/931,654, filed May 14, 2020.
Coronavirus is 'much worse' than influenza: Doctor. Fox Business News. Video (transcript). Transcribed Sep. 16, 2020 from URL: https://video.foxbusiness.com/v/6142665270001/#sp=show-clips. Mar. 18, 2020. 3 pages.
Distributed Bio CEO on developing therapeutic antibody treatment against coronavirus. CNBC Squawk on the Street video (transcript). Transcribed Sep. 16, 2020 from URL: https://www.cnbc.com/video/2020/03/23/distributed-bio-ceo-on-developing-therapeutic-antibody-treatment-against-coronavirus.html. Mar. 23, 2020. 3 pages.
Distributed Bio. @Distributedbio. An update on our monoclonal antibodies being engineered against #COVID19 from @CurlyJungleJake on @SquawkCNBC this morning. (Tweet). Twitter (Mar. 23, 2020). Retrieved Jul. 30, 2020 from https://twitter.com/distributedbio/status/1242123582341181440?s=20. One page.
Distributed Bio. @Distributedbio. Hear more about our progress on engineering our #monoclonal #antibodies to neutralize #COVID19 from @CurlyJungleJake on @TheStoryFNC with ©marthamaccallum (Tweet). Twitter (Mar. 19, 2020). Retrieved Jul. 30, 2020 from https://twitter.com/distributedbio/status/1240798648054591488?s=20. One page.
Distributed Bio. @Distributedbio. It was a blast working with @chrisaiola and @ZPZProduction re #influenza for #Pandemic on #Netflix—hear more about #coronavirus here. (Tweet). Twitter (Mar. 3, 2020). Retrieved Jul. 30, 2020 from https://twitter.com/distributedbio/status/1234873874669547521?s=20. One page.
Dr. Glanville: 3 to 4 weeks before completing engineering on drug that neutralizes coronavirus. Fox News. Video (transcript). Transcribed Sep. 16, 2020 from URL: https://video.foxnews.com/v/6142979870001#sp=show-clips. Mar. 19, 2020. 3 pages.
Fighting the Pandemic: Potential COVID-19 Treatment. CNBC Closing Bell video (transcript). Transcribed Sep. 16, 2020 from URL: https://twitter.com/CNBCClosingBell/status/1252681883772694533?s=20. Apr. 21, 2020. 2 pages.
Glanville, J. @CurlyJungleJake. Interview on @FoxBusiness where we discuss our #antibody therapeutics program for the #coronavirus. (Tweet). Twitter (Mar. 18, 2020). Retrieved Jul. 30, 2020 from https://twitter.com/CurlyJungleJake/status/1240438128680136704?s=20. One page.
Hwang et al. Structural basis of neutralization by a human anti-severe acute respiratory syndrome spike protein antibody, 80R. J Biol Chem. Nov. 10, 2006;281(45):34610-6.doi: 10.1074/jbc.M603275200. Epub Sep. 5, 2006. DOI: 10.1074/jbc.M603275200.
Liew. The Flu, Snake Bites, and the COVID-19 Virus: Jacob Glanville from Netflix's 'Pandemic.' Harnham (Jan. 30, 2020). Retrieved Sep. 5, 2020 at URL: https://www.harnham.com/us/post/2020-1/a-discussion-with-jacob-glanville-from-netflix-s-pandemic?utm_source=Paiger&utm_medium=Referral. 7 pages.
Prabakaran et al. Structure of severe acute respiratory syndrome coronavirus receptor-binding domain complexed with neutralizing antibody. J Biol Chem. Jun. 9, 2006;281(23):15829-36.doi: 10.1074/jbc.M600697200. Epub Apr. 5, 2006. DOI: 10.1074/jbc.M600697200.
Scientists begin their study of covid-19, looking for antibody. Radio New Zealand (RNZ) broadcast (transcript). Transcribed Sep. 16, 2020 from URL: https://www.rnz.co.nz/national/programmes/first-up/audio/2018736849/scientists-begin-their-study-of-covid-19-looking-for-antibody. Mar. 4, 2020. 4 pages.
Villasanta. Coronavirus Vaccine: Netflix Doctor Says He Found 'Very Potent' Drug to Treat COVID-19. International Business Times (Apr. 1, 2020). Retrieved Sep. 18, 2020 at URL: https://www.ibtimes.com/coronavirus-vaccine-netflix-doctor-says-he-found-very-potent-drug-treat-covid-19-2950576. 5 pages.
Walls et al. Unexpected Receptor Functional Mimicry Elucidates Activation of Coronavirus Fusion. Cell. Feb. 21, 2019; 176(5): 1026-1039.e15. Published online Jan. 31, 2019. doi: 10.1016/j.cell.2018.12.028.
Woods. Doctor in Netflix's 'Pandemic' says he discovered potential coronavirus cure. New York Post (Apr. 1, 2020). Retrieved Sep. 18, 2020 at URL: https://nypost.com/2020/04/01/doctor-in-netflix-doc-says-he-discovered-potential-coronavirus-cure/. 6 pages.

* cited by examiner

| Virus | Antigen | Sequence | SEQ ID NO |
|---|---|---|---|
| MERS | 5gmq | VECDFSPLLSGTPPQVYNFKRLVFTNCNYNLTKLLSLFSVN DFTCSQISPAAIASNCYSSLILDYFSYPLSMKSDLSVSSAG PISQFNYKQSFSNPTCLILATVPHNLTTITKPLKYSYINKC SRLLSDDRTEVPQLVNANQYSPCVSIVPSTVWEDGDYYRKQ LSPLEGGGWLVASGSTVAMTEQLQMGFGITVQYGTDTNSVC PKL | 106 |
| 2019-nCoV | 2019-Wuhan-Hu-1 | RFPNITNLCPFGEVFNATRFASVYAWNRKRISNCVADYSVL YNSASFSTFKCYGVSPTKLNDLCFTNVYADSFVIRGDEVRQ IAPGQTGKIADYNYKLPDDFTGCVIAWNSNNLDSKVGGNYN YLYRLFRKSNLKPFERDISTEIYQAGSTPCNGVEGFNCYFP LQSYGFQPTNGVGYQPYRVVVLSFELLHAPATVCGP | 107 |
| SARS | 2dd8_S spike glycopr otein | PNITNLCPFGEVFNATKFPSVYAWERKKISNCVADYSVLYN STFFSTFKCYGVSATKLNDLCFSNVYADSFVVKGDDVRQIA PGQTGVIADYNYKLPDDFMGCVLAWNTRNIDATSTGNYNYK YRYLRHGKLRPFERDISNVPFSPDGKPCTPPALNCYWPLND YGFYTTTGIGYQPYRVVVLSFELLNAPATVCGPKLSTD | 108 |
| SARS | QDF4382 5.1 | PNITNLCPFGEVFNATTFPSVYAWERKRISNCVADYSVLYN STSFSTFKCYGVSATKLNDLCFSNVYADSFVVKGDDVRQIA PGQTGVIADYNYKLPDDFMGCVLAWNTRNIDATSTGNYNYK YRSLRHGKLRPFERDISNVPFSPDGKPCTPPAFNCYWPLND YGFFTTNGIGYQPYRVVVLSFELLNAPATVCGPKLSTD | 109 |

ANTI-SARS-COV-2 ANTIBODIES DERIVED FROM 2GHW

CROSS-REFERENCE

This application claims the benefit of U.S. Provisional Application Nos. 63/014,556, filed Apr. 23, 2020; 63/014,058, filed Apr. 22, 2020; and 62/993,630, filed Mar. 23, 2020, all of which are incorporated herein by reference in their entireties for all purposes.

SEQUENCE LISTING

The instant application contains a Sequence Listing which has been submitted electronically in ASCII format and is hereby incorporated by reference in its entirety. Said ASCII copy, created on Jun. 22, 2020, is named 44561-720_201_SL.txt and is 60,329 bytes in size.

BACKGROUND OF THE INVENTION

Viruses are small infectious agents that can enter a living cell of an organism. Genetic information from a virus can be injected into the living cell, and can replicate inside the living cell, and be released. Viruses can cause disease in the organism and can spread between organisms. The mechanism by which a virus can cause disease can vary between viruses and can include cell lysis and/or cell death.

Coronaviruses are a group of related viruses that can cause disease, for example in mammals and birds. Coronaviruses can cause respiratory tract infections, such as those causing pneumonia-like diseases, that can range from mild to lethal.

Severe acute respiratory syndrome coronavirus 2 (SARS-Cov-2) is a coronavirus responsible for a pandemic of a respiratory disease, COVID19. An outbreak of this virus was first identified in Wuhan, Hubei, China, and a pandemic was recognized by the World Health Organization on Mar. 11, 2020. The range of the severity of COVID19 is large, from asymptomatic to death. Approximately 20% of infected individuals can require hospitalization. The mortality rate of COVID19 appears to be between 1% and 4%. COVID19 is transmitted between people, for example through respiratory droplets, and can be spread by symptomatic and asymptomatic individuals, including during an extended incubation period. Social distancing has been applied worldwide to decrease the spread of COVID19.

Currently, there is no vaccine or treatment for COVID19. There is an urgent need for new compositions that can be used for treating or preventing SARS-Cov-2 infection and for diagnosing an exposure to SARS-Cov-2 virus.

SUMMARY OF THE INVENTION

Provided herein is a 2ghw-derived antibody or antigen-binding fragment that selectively binds to a severe acute respiratory syndrome coronavirus 2 (SARS-Cov-2). In some embodiments, the antibody or antigen-binding fragment has a binding affinity of less than 50 nanomolar (nM). In further embodiments, the 2ghw-derived antibody or antigen-binding fragment selectively binds to a receptor binding domain (RBD) of SARS-Cov-2. In further embodiments, the 2ghw-derived antibody or antigen-binding fragment comprises an amino acid sequence that is at least 90%, 95%, 98%, 99%, or 100% identical to a VH CDR3 VH CDR3 comprising an amino acid sequence of any one of any one of SEQ ID NOS: 59-70. In further embodiments, the 2ghw-derived antibody or antigen-binding fragment comprises VH CDR3 having an amino acid sequence of CARDRX$_1$X$_2$X$_3$X$_4$X$_5$YW (SEQ ID NO: 58), wherein X$_1$ is N, R, or S; X$_2$ is A, L, V, or Y; X$_3$ is G, M, or Y; X$_4$ is I, L, or F; and X$_5$ is D or G. In further embodiments, the 2ghw-derived antibody or antigen-binding fragment further comprises an amino acid sequence that is at least 90%, 95%, 98%, 99%, or 100% identical to one or more of a VH CDR1 comprising an amino acid of sequence any one of SEQ ID NOS: 30-41 and a VH CDR2 comprising an amino acid sequence of any one of SEQ ID NOS: 44-55. In further embodiments, the 2ghw-derived antibody or antigen-binding fragment further comprises a VH CDR1 having an amino acid sequence of X$_1$X$_2$X$_3$X$_4$X$_5$X$_6$X$_7$X$_8$X$_9$ (SEQ ID NO: 29), wherein X$_1$ is F or L; X$_2$ is T, S, R, or A; X$_3$ is F or V; X$_4$ is S or T; X$_5$ is D, N, or S; X$_6$ is H, N, or Y; X$_7$ is A, G, or Y; X$_8$ is M or I; and X$_9$ is S, T, or N; and a VH CDR2 having an amino acid sequence of X$_1$X$_2$X$_3$X$_4$X$_5$X$_6$GX$_7$X$_8$X$_9$X$_{10}$YA (SEQ ID NO: 43), wherein X$_1$ is A or S; X$_2$ is A or T; X$_3$ is I or M; X$_4$ is N or S; X$_5$ is G, R, N, T, or Y; X$_6$ is D, I, S, or T; X$_7$ is D, G, or S; X$_8$ is D, N, S, T, or Y; and X$_9$ is I, K, or T; and wherein X$_{10}$ is E, F, or Y.

In some embodiments, provided herein is a 2ghw-derived antibody or antigen-binding fragment comprising a VH chain that comprises:
a. a VH CDR1 having an amino acid sequence that is at least 90%, 95%, 98%, 99%, or 100% identical to any one of SEQ ID NOS: 30-41;
b. a VH CDR2 having an amino acid sequence that is at least 90%, 95%, 98%, 99%, or 100% identical to any one of SEQ ID NOS: 44-55; and
c. a VH CDR3 having an amino acid sequence that is at least 90%, 95%, 98%, 99%, or 100% identical to any one of SEQ ID NOS: 59-70.

In some embodiments, provided herein is a 2ghw-derived antibody or antigen-binding fragment comprising a VL chain that comprises:
a. a VL CDR1 having an amino acid sequence that is at least 90%, 95%, 98%, 99%, or 100% identical to any one of SEQ ID NOS: 4-9;
b. a VL CDR2 having an amino acid sequence that is at least 90%, 95%, 98%, 99%, or 100% identical to any one of SEQ ID NOS: 13-15; and
c. a VL CDR3 having an amino acid sequence that is at least 90%, 95%, 98%, 99%, or 100% identical to any one of SEQ ID NOS: 20-26.

In some embodiments, provided herein is a 2ghw-derived antibody or antigen-binding fragment comprising a VL chain that comprises:
a. a VL CDR1 having an amino acid sequence of FASQSX$_1$X$_2$X$_3$X$_4$LX$_5$ (SEQ ID NO: 3), wherein X$_1$ is I or V; X$_2$ is G, R, or S; X$_3$ is R, S, or T; X$_4$ is N or Y; and X$_5$ is A, N, or S;
b. a VL CDR2 having an amino acid sequence of X$_1$ASX$_2$X$_3$X$_4$X$_5$ (SEQ ID NO: 12), wherein X$_1$ is A, G, or S; X$_2$ is S or T; X$_3$ is L or R; X$_4$ is Q or A; and X$_5$ is S or T; and
c. a VL CDR3 having an amino acid sequence of CQX$_1$X$_2$X$_3$X$_4$X$_5$X$_6$X$_7$TW (SEQ ID NO: 19), wherein X$_1$ is Q or H; X$_2$ is A, R, S, or Y; X$_3$ is G, L, N, S, or Y; X$_4$ is N or S; X$_5$ is L, S, T, or W; X$_6$ is P or Q; and X$_7$ is L, P, or V.

In some embodiments, provided herein is a 2ghw-derived antibody or antigen-binding fragment, that comprises (i) a VH CDR3 having an amino acid sequence that is at least 90%, 95%, 98%, 99%, or 100% identical to SEQ ID NO: 68; (ii) a VH CDR1 having an amino acid sequence that is at least 90%, 95%, 98%, 99%, or 100% identical to SEQ ID NO: 39; (ii) a VH CDR2 having an amino acid sequence that is at least 90%, 95%, 98%, 99%, or 100% identical to SEQ ID NO: 53; (iv) a VL CDR1 having an amino acid sequence that is at least 90%, 95%, 98%, 99%, or 100% identical to SEQ ID NO: 7; (v) a VL CDR2 having an amino acid sequence that is at least 90%, 95%, 98%, 99%, or 100% identical to SEQ ID NO: 15; and (vi) a VL CDR3 having an amino acid sequence that is at least 90%, 95%, 98%, 99%, or 100% identical to SEQ ID NO: 25. In further embodiments, the 2ghw-derived antibody or antigen-binding fragment comprises a VH chain having an amino acid sequence that is at least 90%, 95%, 98%, 99%, or 100% identical to any one of SEQ ID NOS: 72-83. In further embodiments, the 2ghw-derived antibody or antigen-binding fragment comprises a VL chain having an amino acid sequence that is at least 90%, 95%, 98%, 99%, or 100% identical to any one of SEQ ID NOS: 84-95. In further embodiments, the 2ghw-derived antibody or antigen-binding fragment comprises a VL having an amino acid sequence that is at least 90%, 95%, 98%, 99%, or 100% identical to any one of SEQ ID NOS: 84-95, and a VH having an amino acid sequence that is at least 90%, 95%, 98%, 99%, or 100% identical to any one of SEQ ID NOS: 72-83. In further embodiments, the 2ghw-derived antibody or antigen-binding fragment comprises a VH having an amino acid sequence that is at least 90%, 95%, 98%, 99%, or 100% identical to SEQ ID NO: 81 and a VL having an amino acid sequence that is at least 90%, 95%, 98%, 99%, or 100% identical to SEQ ID NO: 93. In further embodiments, the 2ghw-derived antibody or antigen-binding fragment comprises an amino acid sequence that is at least 90%, 95%, 98%, 99%, or 100% identical to one or more of a FW-L1 comprising an amino acid sequence of SEQ ID NO: 1 or 2, a FW-L2 comprising an amino acid sequence of SEQ ID NO: 10 or 11, a FW-L3 comprising an amino acid sequence of any one of any one of SEQ ID NOS: 16-18, a FW-L4 comprising amino acid of SEQ ID NO: 27, a FW-H1 comprising an amino acid sequence of SEQ ID NO: 28, a FW-H2 comprising amino acid sequence of SEQ ID NO: 42, a FW-H3 comprising an amino acid sequence of SEQ ID NO: 56 or 57, and a FW-H4 comprising an amino acid sequence of SEQ ID NO: 71. In further embodiments, the 2ghw-derived antibody comprises a monoclonal antibody, a grafted antibody, a chimeric antibody, a human antibody, or a humanized antibody.

In further embodiments, provided herein is a2ghw-derived antibody or antigen-binding fragment wherein the binding affinity is less than 50 nM, 49 nM, 48 nM, 47 nM, 46 nM, 45 nM, 44 nM, 43 nM, 42 nM, 41 nM, 40 nM, 39 nM, 38 nM, 37 nM, 36 nM, 35 nM, 34 nM, 33 nM, 32 nM, 31 nM, 30 nM, 29 nM, 28 nM, 27 nM, 26 nM, 25 nM, 24 nM, 23 nM, 22 nM, 21 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, 1 nM, 990 pM, 980 pM, 970 pM, 960 pM, 950 pM, 940 pM, 930 pM, 920 pM, 910 pM, 900 pM, 890 pM, 880 pM, 870 pM, 860 pM, 850 pM, 840 pM, 830 pM, 820 pM, 810 pM, 800 pM, 790 pM, 780 pM, 770 pM, 760 pM, 750 pM, 740 pM, 730 pM, 720 pM, 710 pM, or 700 pM, or any integer therebetween. In further embodiments, provided herein is a2ghw-derived antibody or antigen-binding fragment wherein the antibody's antigen-binding domain or the antigen-binding fragment comprises a Fab, a Fab', a F(ab')$_2$, a variable fragment (Fv), a triabody, a tetrabody, a minibody, a bispecific F(ab')$_2$, a trispecific F(ab')$_2$, a diabody, a bispecific diabody, a single chain variable fragment (scFv), a scFv-Fc, a Fab-Fc, a VHH, or a bispecific scFv.

Provided herein is a method of preventing or treating a SARS-CoV-2 viral infection or COVID19 in a subject in need thereof. In some embodiments, the method comprises administering to the subject one or more of the 2ghw-derived antibodies or antigen-binding fragments described herein. In further embodiments, the method further comprises administering one or more additional therapies or drugs to the subject.

Provided herein is a method of diagnosing a subject as being infected with a SARS-Cov-2 virus or suspected of being infected with a SARS-Cov-2 virus, the method comprising contacting a sample obtained from the subject with a 2ghw-derived antibody or antigen-binding fragment described herein; detecting the presence or absence of the 2ghw-derived antibody or antigen-binding fragment; and diagnosing the subject as being infected with a SARS-Cov-2 virus when the presence of the 2ghw-derived antibody or antigen-binding fragment is detected. In further embodiments, the sample comprises a nasal swab, a tissue sample, saliva, or blood. In further embodiments, detecting the presence or absence of the 2ghw-derived antibody or antigen-binding fragment comprises an enzyme linked immunosorbent assay (ELISA), an immunospot assay, a lateral flow assay, flow cytometry, immunohistochemistry, or a western blot.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DISCLOSURE OF THE DRAWINGS

The novel features of the invention are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1 provides representative viral antigen sequences.

DETAILED DESCRIPTION OF THE INVENTION

In view of the ongoing pandemic, there is a great need for therapeutic and diagnostic antibodies that selectively bind to severe acute respiratory syndrome coronavirus 2 (SARS-Cov-2).

"2ghw" is a SARS-Cov-1 spike protein receptor binding domain. A "parental clone" or a "parental clone 2ghw" as used herein refers to an antibody that selectively binds to SARS-Cov-1 and which has the following combination of complementarity determining regions (CDRs), or the following variable heavy chain (VH), and variable light chain (VL).

|         | Parental Clone CDRs | SEQ ID NO |
|---------|---------------------|-----------|
| VH CDR1 | FAFSSYAMH           | 96        |
| VH CDR2 | AVISYDGSNKYYA       | 97        |
| VH CDR3 | CARDRSYYLDY         | 98        |
| VL CDR1 | RASQSVRSNLA         | 99        |

-continued

| | | Parental Clone CDRs | SEQ ID NO |
|---|---|---|---|
| VL | CDR2 | DASTRAT | 100 |
| VL | CDR3 | CQQRSNWPPT | 101 |

| Clone | VH/VL | Parental Clone Sequences | SEQ ID NO |
|---|---|---|---|
| 2ghw | VH | EVQLVQSGGGVVQPGKSLRLSCAASGFAFSSYAMH WVRQAPGKGLEWVAVISYDGSNKYYADSVKGRFT ISRDNSKNTLYLQMNSLRAEDTAVYYCARDRSYYL DYWGQGTLVTVSS | 102 |
| 2ghw | VL | ETTLTQSPATLSLSPGERATLSCRASQSVRSNLAWY QQKPGQAPRPLIYDASTRATGIPDRFSGSGSGTDFTL TISRLEPEDFAVYYCQQRSNWPPTFGQGTKVEVK | 103 |

The present disclosure describes 2ghw-derived antibodies and antigen-binding fragments herein that selectively bind to SARS-Cov-2.

A 2ghw-derived antibody or antigen-binding fragment herein that is "derived from" these parental clones and which selectively binds to SARS-Cov-1 refers to an antibody or antigen-binding fragment that does not comprise amino acid sequences that are 100% identical to the combination of CDRs of the parental clone, or that does not comprise amino acid sequences that are 100% identical to the VH having an amino acid sequence of SEQ ID NO: 102 and the VL having an amino acid sequence of SEQ ID NO: 103. Instead, such 2ghw-derived antibodies or antibody-binding fragments can have some degree of sequence identity to the parental clone 2ghw, as disclosed herein.

As used herein, the terms "2ghw-derived antibody or antigen-binding fragment" and "2ghw-derived antibody or antigen-binding fragment herein which selectively binds to SARS-Cov-2" are synonymous.

A 2ghw-derived antibody or antigen-binding fragment herein also refers to an antibody or antigen-binding fragment that selectively binds to SARS-Cov-2, and which has a greater binding affinity for SARS-Cov-2 than to SARS-Cov-1. A 2ghw-derived ed antibody or antigen-binding fragment herein that is derived from the parental clone also refers to a 2ghw-derived antibody or antigen-binding fragment that is capable of neutralizing the activity of SARS-Cov-2. A 2ghw-derived antibody or antigen-binding fragment herein can selectively bind to the receptor binding domain (RBD) of SARS-Cov-2. In one instance, a 2ghw-derived antibody or antigen-binding fragment herein selectively binds solely to SARS-Cov-2, and not to SARS1, SARS2, and/or Middle East Respiratory Syndrome (MERS).

Binding affinity of a 2ghw-derived antibody or antigen-binding fragment herein can be determined by any suitable means including, but not limited to, high-throughput surface plasmon resonance (SPR) kinetic experiments. Briefly, a 2ghw-derived antibody or antigen-binding fragment herein is immobilized to a solid surface using an anti-V5 antibody. Different concentrations of antigen (SARS-Cov-2, SARS-Cov-1, SARS2, or MERS RBD proteins) are flowed over the immobilized 2ghw-derived antibodies or antigen-binding fragments to characterize the interactions to the immobilized 2ghw-derived antibodies or antigen-binding fragments. The SPR signal originates from changes in the refractive index at the surface of a gold sensor chip. An increase in mass associated with a binding event between an antibody or antigen-binding fragment and the antigen causes a proportional increase in the refractive index, which is observed as a change in response. These changes are measured as changes in the resonance angle (60) of refracted light when the antigen, flowing in a microfluidic channel, binds to the immobilized antibody and increases in density at the sensor chip. For antibody-antigen interactions, the change in refractive index on the surface is linearly related to the number of antigens bound to an immobilized antibody. The response signal (the SPR signal) is quantified in resonance units (RU). When a steady-state is achieved (all binding sites occupied), the maximum RU is determined (n: number of binding sites in ligand). Monitoring the change in the SPR signal over time produces a sensorgram, a plot of the binding response (RU) versus time which allows different stages of a binding event to be visualized and evaluated. During the injection of an antigen, the binding response increase is due to the formation of antigen-antibody complexes at the surface and the sensorgram is dominated by the association phase. After a certain time of injection, a steady state is reached, in which binding and dissociating molecules are in equilibrium. The decrease in response after analyte injection is terminated is due to dissociation of the complexes, defining the dissociation phase. Depending on the dissociation rate of the tested antibody, some assays may require a regeneration step in order to reach the baseline again. Fitting the sensorgram data to an appropriate kinetic binding model allows calculation of kinetic parameters such as the association ($k_a$) and dissociation ($k_d$) rate constants, and the binding affinity of the tested interactions.

Preferably, a 2ghw-derived antibody or antigen-binding fragment herein has a binding affinity for SARS-Cov-2 of less than 50 nM. In one instance, a 2ghw-derived antibody or antigen-binding fragment herein can selectively bind to SARS-Cov-2 with a binding affinity of from about 0.7 nM (700 pM) to about 50 nM. In one instance, a 2ghw-derived antibody or antigen-binding fragment herein selectively bind to SARS-Cov-2 with a binding affinity of less than 50 nM, 49 nM, 48 nM, 47 nM, 46 nM, 45 nM, 44 nM, 43 nM, 42 nM, 41 nM, 40 nM, 39 nM, 38 nM, 37 nM, 36 nM, 35 nM, 34 nM, 33 nM, 32 nM, 31 nM, 30 nM, 29 nM, 28 nM, 27 nM, 26 nM, 25 nM, 24 nM, 23 nM, 22 nM, 21 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, nM, 1 nM, 990 pM, 980 pM, 970 pM, 960 pM, 950 pM, 940 pM, 930 pM, 920 pM, 910 pM, 900 pM, 890 pM, 880 pM, 870 pM, 860 pM, 850 pM, 840 pM, 830 pM, 820 pM, 810 pM, 800 pM, 790 pM, 780 pM, 770 pM, 760 pM, 750 pM, 740 pM, 730 pM, 720 pM, 710 pM, or 700 pM, or any integer therebetween.

In any of the embodiments herein, a 2ghw-derived antibody or antigen-binding fragment herein can neutralize the activity of SARS-Cov-2. Neutralization ability of a 2ghw-derived antibody or antigen-binding fragment herein can be assessed using any suitable means including, but not limited to, an in vitro pseudovirus assay. For example, spike genes from a SARS-Cov-2 virus are codon-optimized for human cells and cloned into eukaryotic expression plasmids to generate envelope recombinant plasmids; mammalian cells are then transfected with the plasmids. The transfected mammalian cells are contacted with a 2ghw-derived antibody or antigen-binding fragment herein and trypsinization is determined as a measure of neutralization. In some instances, a 2ghw-derived antibody or antigen-binding fragment herein neutralize SARS-Cov-2 by at least 5%, 10%, 15%, 20%, 25%, 35%, 40%, 45%, 50%, 55%, 60%, 65%, 70%, 75%, 80%, 85%, 90%, or more compared to a non-specific antibody, or compared to an antibody that selectively binds to SARS-Cov-1 or MERS. Neutralization ability of a 2ghw-derived antibody or antigen-binding fragment herein can also be assessed using, for example, an in vivo hamster animal model. For example, hamsters can be injected with either saline or a 2ghw-derived antibody or antigen-binding fragment herein. Body weight and viable signs (e.g., ruffled hair and movement) are recorded. Viral titers are assessed in homogenates of lung tissues and/or by immunohistochemistry of lung tissue. A 2ghw-derived antibody or antigen-binding fragment herein reduces viral titers compared to controls.

Competition assay of the interaction of SARS-Cov-2 with angiotensin-converting enzyme 2 (ACE2) can be assessed using an assay including, but not limited to, a classical sandwich and premix assay format. For example, anti-V5 tag antibodies are biotinylated and loaded onto streptavidin sensor tips. For a classical sandwich assay format, a 2ghw-derived antibody or antigen-binding fragment herein is loaded onto the anti-V5 sensor tips. Following establishment of a baseline, SARS-Cov-2 is added, followed by sandwiching of ACE2 or buffer. Dissociation in buffer is measured. Capture of biotinylated ACE2 is included as a self-blocking control. Alternatively, for a premix assay format, a 2ghw-derived antibody or antigen-binding fragment herein are loaded onto the anti-V5 sensor tips. Following establishment of a baseline, a premix complex of SARS-Cov-2+ACE2, or a SARS-Cov-2 alone are added to the antibodies or antigen-binding fragments. Dissociation in buffer is measured. Capture of biotinylated ACE2 is included as a self-blocking control.

Representative CDR Sequences that Selectively Bind to SARS-Cov-2

A 2ghw-derived antibody or antigen-binding fragment herein that selectively binds to SARS-Cov-2 can comprise a VH CDR3 having an amino acid sequence of CARDRX$_1$X$_2$X$_3$X$_4$X$_5$YW (SEQ ID NO: 58), wherein X$_1$ is N, R, or S; X$_2$ is A, L, V, or Y; X$_3$ is G, M, or Y; X$_4$ is I, L, or F; and X$_5$ is D or G.

A 2ghw-derived antibody or antigen-binding fragment herein that selectively binds to SARS-Cov-2 can comprise a VH CDR1 having an amino acid sequence of X$_1$X$_2$X$_3$X$_4$X$_5$X$_6$X$_7$X$_8$X$_9$ (SEQ ID NO: 29), wherein X$_1$ is F or L; X$_2$ is T, S, R, or A; X$_3$ is F or V; X$_4$ is S or T; X$_5$ is D, N, or S; X$_6$ is H, N, or Y; X$_7$ is A, G, or Y; X$_8$ is M or I; and X$_9$ is S, T, or N.

A 2ghw-derived antibody or antigen-binding fragment herein that selectively binds to SARS-Cov-2 can comprise a VH CDR2 having an amino acid sequence of X$_1$X$_2$X$_3$X$_4$X$_5$X$_6$GX$_7$X$_8$X$_9$X$_{10}$YA (SEQ ID NO: 43), wherein X$_1$ is A or S; X$_2$ is A or T; X$_3$ is I or M; X$_4$ is N or S; X$_5$ is G, R, N, T, or Y; X$_6$ is D, I, S, or T; X$_7$ is D, G, or S; X$_8$ is D, N, S, T, or Y; and X$_9$ is I, K, or T; and wherein X$_{10}$ is E, F, or Y.

A 2ghw-derived antibody or antigen-binding fragment herein that selectively binds to SARS-Cov-2 can comprise a VL CDR1 having an amino acid sequence of FASQSX$_1$X$_2$X$_3$X$_4$LX$_5$ (SEQ ID NO: 3), wherein X$_1$ is I or V; X$_2$ is G, R, or S; X$_3$ is R, S, or T; X$_4$ is N or Y; and X$_5$ is A, N, or S.

A 2ghw-derived antibody or antigen-binding fragment herein that selectively binds to SARS-Cov-2 can comprise a VL CDR2 having an amino acid sequence of X$_1$ASX$_2$X$_3$X$_4$X$_5$ (SEQ ID NO: 12), wherein X$_1$ is A, G, or S; X$_2$ is S or T; X$_3$ is L or R; X$_4$ is Q or A; and X$_5$ is S or T.

A 2ghw-derived antibody or antigen-binding fragment herein that selectively binds to SARS-Cov-2 can comprise a VL CDR3 having an amino acid sequence of CQX$_1$X$_2$X$_3$X$_4$X$_5$X$_6$X$_7$TW (SEQ ID NO: 19), wherein X$_1$ is Q or H; X$_2$ is A, R, S, or Y; X$_3$ is G, L, N, S, or Y; X$_4$ is N or S; X$_5$ is L, S, T, or W; X$_6$ is P or Q; and X$_7$ is L, P, or V.

A 2ghw-derived antibody or antigen-binding fragment herein that selectively binds to SARS-Cov-2 can comprise an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to a VH CDR3 comprising an amino acid sequence of any one of any one of SEQ ID NOS: 59-70. In some instances, a 2ghw-derived antibody or antigen-binding fragment herein that selectively binds to SARS-Cov-2 can further comprise an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to one or more of a VH CDR1 comprising an amino acid sequence of any one of SEQ ID NOS: 30-41 and a VH CDR2 comprising an amino acid sequence of any one of SEQ ID NOS: 44-55. In some instances, a 2ghw-derived antibody or antigen-binding fragment herein that selectively binds to SARS-Cov-2 can further comprise an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to one or more of a VL CDR1 comprising an amino acid sequence of any one of SEQ ID NOS: 4-9, a VL CDR2 comprising an amino acid sequence of any one of SEQ ID NOS: 13-15, and a VL CDR3 comprising an amino acid sequence of any one of SEQ ID NOS: 20-26. In other instances, a 2ghw-derived antibody or antigen-binding fragment herein that selectively binds to SARS-Cov-2 can comprise an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to one or more of a VH CDR1 comprising amino acid sequence of any one of SEQ ID NOS: 30-41, a VH CDR2 comprising amino acid sequence of any one of SEQ ID NOS: 44-55, a VH CDR3 comprising amino acid sequence of any one of any one of SEQ ID NOS: 59-70, a VL CDR1 comprising amino acid sequence of any one of SEQ ID NOS: 4-9, a VL CDR2 comprising amino acid sequence of any one of SEQ ID NOS: 13-15, and a VL CDR3 comprising amino acid sequence of any one of SEQ ID NOS: 20-26.

Representative VH CDR3 Sequences

A 2ghw-derived antibody or antigen-binding fragment herein that selectively binds to SARS-Cov-2 can comprise a VH CDR3 having an amino acid sequence of CARDRX$_1$X$_2$X$_3$X$_4$X$_5$YW (SEQ ID NO: 58), wherein X$_1$ is N, R, or S; X$_2$ is A, L, V, or Y; X$_3$ is G, M, or Y; X$_4$ is I, L, or F; and X$_5$ is D or G. In one instance, the VH CDR3 comprises an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to any one of the following sequences:

| Clone ID | VH CDR3 | SEQ ID NO: |
| --- | --- | --- |
| COVID19_P04_B10 | CARDRSYGIDYW | 59 |
| COVID19_P04_G03 | CARDRSYYLDYW | 60 |
| COVID19_P04_G05 | CARDRSYYLDYW | 61 |
| COVID19_R01_B01 | CARDRGWYLDYW | 62 |
| COVID19_P04_D08 | CARDRRVYLDYW | 63 |
| COVID19_P04_B03 | CARDRSYYLDYW | 64 |
| COVID19_P04_B09 | CARDRSLMLDYW | 65 |
| COVID19_P04_E10 | CARDRSYVGYW | 66 |
| COVID19_R01_A04 | CARDRSYYLDYW | 67 |
| COVID19_R01_D02 | CARDRSGYLDYW | 68 |

| Clone ID | VH CDR3 | SEQ ID NO: |
|---|---|---|
| COVID19_R01_B10 | CARDRSYYLDYW | 69 |
| COVID19_R01_C08 | CARDRSYYVGYW | 70 |

Representative VH CDR1 Sequences

A 2ghw-derived antibody or antigen-binding fragment herein that selectively binds to SARS-Cov-2 can comprise a VH CDR1 having an amino acid sequence of $X_1X_2X_3X_4X_5X_6X_7X_8X_9$ (SEQ ID NO: 29), wherein $X_1$ is F or L; $X_2$ is T, S, R, or A; $X_3$ is F or V; $X_4$ is S or T; $X_5$ is D, N, or S; $X_6$ is H, N, or Y; $X_7$ is A, G, or Y; $X_8$ is M or I; and $X_9$ is S, T, or N. In one instance, the VH CDR1 comprises an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to any one of the following sequences:

| Clone ID | VH CDR1 | SEQ ID NO: |
|---|---|---|
| COVID19_P04_B10 | FRFSDAAIH | 30 |
| COVID19_P04_G03 | FTVSSNYMN | 31 |
| COVID19_P04_G05 | LSVTSNYMS | 32 |
| COVID19_R01_B01 | FTFASHAMS | 33 |
| COVID19_P04_D08 | FTFTNYAMT | 34 |
| COVID19_P04_B03 | FTFSNHYMS | 35 |
| COVID19_P04_B09 | FTFSNSDMN | 36 |
| COVID19_P04_E10 | FSFSSYGMS | 37 |
| COVID19_R01_A04 | FTFSDHYMS | 38 |
| COVID19_R01_D02 | FTFDDYAMH | 39 |
| COVID19_R01_B10 | FTVSSNYMS | 40 |
| COVID19_R01_C08 | FSFSSYGMS | 41 |

Representative VH CDR2 Sequences

A 2ghw-derived antibody or antigen-binding fragment herein that selectively binds to SARS-Cov-2 can comprise a VH CDR2 having an amino acid sequence of $X_1X_2X_3X_4X_5X_6GX_7X_8X_9X_{10}YA$ (SEQ ID NO: 43), wherein $X_1$ is A or S; $X_2$ is A or T; $X_3$ is I or M; $X_4$ is N or S; $X_5$ is G, R, N, T, or Y; $X_6$ is D, I, S, or T; $X_7$ is D, G, or S; $X_8$ is D, N, S, T, or Y; and $X_9$ is I, K, or T; and wherein $X_{10}$ is E, F, or Y. In one instance, the VH CDR2 comprises an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to any one of the following sequences:

| Clone ID | VH CDR2 | SEQ ID NO: |
|---|---|---|
| COVID19_P04_B10 | SAISGSGGSTYYA | 44 |
| COVID19_P04_G03 | SVVYPGGSTYYA | 45 |
| COVID19_P04_G05 | SVIYPGGSTFYA | 46 |
| COVID19_R01_B01 | SGISSDGSITTYA | 47 |
| COVID19_P04_D08 | STMSNIGGDTYYA | 48 |
| COVID19_P04_B03 | SAISGSGGSTYYA | 49 |
| COVID19_P04_B09 | SAISGTGDTTEYA | 50 |
| COVID19_P04_E10 | SAMNRDGSYIYYA | 51 |
| COVID19_R01_A04 | SAISTSGDSTFYA | 52 |
| COVID19_R01_D02 | AIIYEGGSPHYA | 53 |
| COVID19_R01_B10 | SVIYPGGSTFYA | 54 |
| COVID19_R01_C08 | SAMNRDGSYIYYA | 55 |

Representative VL CDR1 Sequences

A2ghw-derived antibody or antigen-binding fragment herein that selectively binds to SARS-Cov-2 can comprise a VL CDR having an amino acid sequence of $FASQSX_1X_2X_3X_4LX_5$ (SEQ ID NO: 3), wherein $X_1$ is I or V; $X_2$ is G, R, or S; $X_3$ is R, S, or T; $X_4$ is N or Y; and $X_5$ is A, N, or S. In one instance, the VL CDR1 comprises an amino acid sequence that is at least 20%, 25%, 30, 35%, 40%, 45%, 50%, 55%, 60%, 65%, 70%, 75%, 80%, 85%, 90%, 95%, 98%, 99% or 100% identical to any one of the following sequences:

| Clone ID | VL CDR1 | SEQ ID NO: |
|---|---|---|
| COVID19_P04_B10 | RASQSISSYLN | 4 |
| COVID19_P04_G03 | RASQSISSYLN | 4 |
| COVID19_P04_G05 | RASQSISSYLN | 4 |
| COVID19_R01_B01 | RASQSISSYLN | 4 |
| COVID19_P04_D08 | RASQSISSYLN | 4 |
| COVID19_P04_B03 | RASQSIGTYLS | 5 |
| COVID19_P04_B09 | RASQSVRSNLA | 6 |
| COVID19_P04_E10 | RASQSVRSNLA | 6 |
| COVID19_R01_A04 | RASQSVRSNLA | 6 |
| COVID19_R01_D02 | RASQSVSNNLA | 7 |
| COVID19_R01_B10 | RASQSVSSSYLA | 8 |
| COVID19_R01_C08 | RASQSVSSNLA | 9 |

Representative VL CDR2 Sequences

A 2ghw-derived antibody or antigen-binding fragment herein that selectively binds to SARS-Cov-2 can comprise a VL CDR2 having an amino acid sequence of $X_1ASX_2X_3X_4X_5$ (SEQ ID NO: 12), wherein $X_1$ is A, G, or S; $X_2$ is S or T; $X_3$ is L or R; $X_4$ is Q or A; and $X_5$ is S or T. In one instance, the VL CDR2 comprises an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to any one of the following sequences:

| Clone ID | VL CDR2 | SEQ ID NO: |
|---|---|---|
| COVID19_P04_B10 | AASSLQS | 13 |
| COVID19_P04_G03 | AASSLQS | 13 |
| COVID19_P04_G05 | AASSLQS | 13 |
| COVID19_R01_B01 | AASSLQS | 13 |
| COVID19_P04_D08 | AASSLQS | 13 |
| COVID19_P04_B03 | GASTRAT | 14 |
| COVID19_P04_B09 | GASTRAT | 14 |
| COVID19_P04_E10 | GASTRAT | 14 |
| COVID19_R01_A04 | GASTRAT | 14 |
| COVID19_R01_D02 | DASTRAT | 15 |
| COVID19_R01_B10 | GASTRAT | 14 |
| COVID19_R01_C08 | GASTRAT | 14 |

Representative VL CDR3 Sequences

A 2ghw-derived antibody or antigen-binding fragment herein that selectively binds to SARS-Cov-2 can comprise a VL CDR3 having an amino acid sequence of CQX$_1$X$_2$X$_3$X$_4$X$_5$X$_6$X$_7$TW (SEQ ID NO: 19), wherein X$_1$ is Q or H; X$_2$ is A, R, S, or Y; X$_3$ is G, L, N, S, or Y; X$_4$ is N or S; X$_5$ is L, S, T, or W; X$_6$ is P or Q; and X$_7$ is L, P, or V. In one instance, the VL CDR3 comprises an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to any one of the following sequences:

| Clone ID | VL CDR3 | SEQ ID NO: |
|---|---|---|
| COVID19_P04_B10 | CQQSYSTPLTF | 20 |
| COVID19_P04_G03 | CQQSYSTPLTF | 20 |
| COVID19_P04_G05 | CQQSYSTPLTF | 20 |
| COVID19_R01_B01 | CQQSYSTPLTF | 20 |
| COVID19_P04_D08 | CQQYGSSPLTF | 21 |
| COVID19_P04_B03 | CQQSLSLPVTF | 22 |
| COVID19_P04_B09 | CQQRNNWPPTF | 23 |
| COVID19_P04_E10 | CQQRNNWPPTF | 23 |
| COVID19_R01_A04 | CQQFGTSPPGLSF | 24 |
| COVID19_R01_D02 | CQQYNNWPPTF | 25 |
| COVID19_R01_B10 | CQQASSTPLTF | 26 |
| COVID19_R01_C08 | CQQRNNWPPTF | 23 |

Representative CDR Combinations

In one instance, the 2ghw-derived antibody or antigen-binding fragment that selectively binds to SARS-Cov-2 can comprise (i) a VH CDR3 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 59; (ii) a VH CDR1 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 30; (ii) a VH CDR2 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 44; (iv) a VL CDR1 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 4; (v) a VL CDR2 having an amino acid sequence that is at least 20%, 25%, 30%, 35%, 40%, 45%, 50%, 55%, 60%, 65%, 70%, 75%, 80%, 85%, 90%, 95% 98%, 99%, or 100% identical to SEQ ID NO: 13; and (vi) a VL CDR3 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 20.

In one instance, the 2ghw-derived antibody or antigen-binding fragment that selectively binds to SARS-Cov-2 can comprise (i) a VH CDR3 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 60; (ii) a VH CDR1 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 31; (ii) a VH CDR2 having an amino acid sequence that is at least 20%, 25%, 30%, 35% 40%, 45%, 50%, 55%, 60%, 65%, 70%, 75%, 80%, 85%, 90%, 95% 98%, 99%, or 100% identical to SEQ ID NO: 45; (iv) a VL CDR1 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 4; (v) a VL CDR2 having an amino acid sequence that is at least 20%, 25%, 30%, 35%, 40%, 45%, 50%, 55%, 60%, 65%, 70%, 75%, 80%, 85%, 90%, 95% 98%, 99%, or 100% identical to SEQ ID NO: 13; and (vi) a VL CDR3 having an amino acid sequence that is at least 20%, 25%, 30%, 35% 40%, 45% 50%, 55% 60%, 65%, 70%, 75% 80%, 85%, 90%, 95% 98%, 99%, or 100% identical to SEQ ID NO: 20.

In one instance, the 2ghw-derived antibody or antigen-binding fragment that selectively binds to SARS-Cov-2 can comprise (i) a VH CDR3 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 61; (ii) a VH CDR1 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 32; (ii) a VH CDR2 having an amino acid sequence that is at least 20%, 25%, 30%, 35%, 40%, 45%, 50%, 55%, 60%, 65%, 70%, 75%, 80%, 85%, 90%, 95% 98%, 99%, or 100% identical to SEQ ID NO: 46; (iv) a VL CDR1 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 4; (v) a VL CDR2 having an amino acid sequence that is at least 20%, 25%, 30%, 35%, 40%, 45%, 50%, 55%, 60%, 65%, 70%, 75%, 80%, 85%, 90%, 95% 98%, 99%, or 100% identical to SEQ ID NO: 13; and (vi) a VL CDR3 having an amino acid sequence that is at least 20%, 25%, 30%, 35%, 40%, 45%, 50%, 55%, 60%, 65%, 70%, 75%, 80%, 85%, 90%, 95% 98%, 99%, or 100% identical to SEQ ID NO: 20.

In one instance, the 2ghw-derived antibody or antigen-binding fragment that selectively binds to SARS-Cov-2 can comprise (i) a VH CDR3 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 62; (ii) a VH CDR1 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 33; (ii) a VH CDR2 having an amino acid sequence that is at least 20%, 25%, 30%, 35%, 40%, 45%, 50%, 55%, 60%, 65%, 70%, 75%, 80%, 85%, 90%, 95% 98%, 99%, or 100% identical to SEQ ID NO: 47; (iv) a VL CDR1 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 4; (v) a VL CDR2 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 13; and (vi) a VL CDR3 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 20.

In one instance, the 2ghw-derived antibody or antigen-binding fragment that selectively binds to SARS-Cov-2 can comprise (i) a VH CDR3 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 63; (ii) a VH CDR1 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 34; (ii) a VH CDR2 having an amino acid sequence that is at least 20%, 25%, 30%, 35%, 40%, 45%, 50%, 55%, 60%, 65%, 70%, 75%, 80%, 85%, 90%, 95% 98%, 99%, or 100% identical to SEQ ID NO: 48; (iv) a VL CDR1 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 4; (v) a VL CDR2 having an amino acid sequence that is at least 20%, 25%, 30%, 35%, 40%, 45%, 50%, 55%, 60%, 65%, 70%, 75%, 80%, 85%, 90%, 95% 98%, 99%, or 100% identical to SEQ ID NO: 13; and (vi) a VL CDR3 having an amino acid sequence that is at least 20%, 25%, 30%, 35%, 40%, 45%, 50%, 55%, 60%, 65%, 70%, 75%, 80%, 85%, 90%, 95% 98%, 99%, or 100% identical to SEQ ID NO: 21.

In one instance, the 2ghw-derived antibody or antigen-binding fragment that selectively binds to SARS-Cov-2 can comprise (i) a VH CDR3 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 64; (ii) a VH CDR1 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 35; (ii) a VH CDR2 having an amino acid sequence that is at least 20%, 25%, 30%, 35%, 40%, 45%, 50%, 55%, 60%, 65%, 70%, 75%, 80%, 85%, 90%, 95% 98%, 99%, or 100% identical to SEQ ID NO: 49; (iv) a VL CDR1 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 5; (v) a VL CDR2 having an amino acid sequence that is at least 20%, 25%, 30%, 35%, 40%, 45%, 50%, 55%, 60%, 65%, 70%, 75%, 80%, 85%, 90%, 95% 98%, 99%, or 100% identical to SEQ ID NO: 14; and (vi) a VL CDR3 having an amino acid sequence that is at least 20%, 25%, 30%, 35%, 40%, 45%, 50%, 55%, 60%, 65%, 70%, 75%, 80%, 85%, 90%, 95% 98%, 99%, or 100% identical to SEQ ID NO: 22.

In one instance, the 2ghw-derived antibody or antigen-binding fragment that selectively binds to SARS-Cov-2 can comprise (i) a VH CDR3 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 65; (ii) a VH CDR1 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 36; (ii) a VH CDR2 having an amino acid sequence that is at least 20%, 25%, 30%, 35%, 40%, 45%, 50%, 55%, 60%, 65%, 70%, 75%, 80%, 85%, 90%, 95% 98%, 99%, or 100% identical to SEQ ID NO: 50; (iv) a VL CDR1 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 6; (v) a VL CDR2 having an amino acid sequence that is at least 20%, 25%, 30%, 35%, 40%, 45%, 50%, 55%, 60%, 65%, 70%, 75%, 80%, 85%, 90%, 95% 98%, 99%, or 100% identical to SEQ ID NO: 14; and (vi) a VL CDR3 having an amino acid sequence that is at least 20%, 25%, 30%, 35%, 40%, 45%, 50%, 55%, 60%, 65%, 70%, 75%, 80%, 85%, 90%, 95% 98%, 99%, or 100% identical to SEQ ID NO: 23.

In one instance, the 2ghw-derived antibody or antigen-binding fragment that selectively binds to SARS-Cov-2 can comprise (i) a VH CDR3 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 66; (ii) a VH CDR1 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 37; (ii) a VH CDR2 having an amino acid sequence that is at least 20%, 25%, 30%, 35%, 40%, 45%, 50%, 55%, 60%, 65%, 70%, 75%, 80%, 85%, 90%, 95% 98%, 99%, or 100% identical to SEQ ID NO: 51; (iv) a VL CDR1 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 6; (v) a VL CDR2 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 14; and (vi) a VL CDR3 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 23.

In one instance, the 2ghw-derived antibody or antigen-binding fragment that selectively binds to SARS-Cov-2 can comprise (i) a VH CDR3 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 67; (ii) a VH CDR1 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 38; (ii) a VH CDR2 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 52; (iv) a VL CDR1 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 6; (v) a VL CDR2 having an amino acid sequence that is at least 20%, 25%, 30%, 35%, 40%, 45%, 50%, 55%, 60%, 65%, 70%, 75%, 80%, 85%, 90%, 95% 98%, 99%, or 100% identical to SEQ ID NO: 14; and (vi) a VL CDR3 having an amino acid sequence that is at least 20%, 25%, 30%, 35% 40%, 45% 50%, 55% 60%, 65%, 70%, 75% 80%, 85%, 90%, 95% 98%, 99%, or 100% identical to SEQ ID NO: 24.

In one instance, the 2ghw-derived antibody or antigen-binding fragment that selectively binds to SARS-Cov-2 can comprise (i) a VH CDR3 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 68; (ii) a VH CDR1 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 39; (ii) a VH CDR2 having an amino acid sequence that is at least 20%, 25%, 30%, 35%, 40%, 45%, 50%, 55%, 60%, 65%, 70%, 75%, 80%, 85%, 90%, 95% 98%, 99%, or 100% identical to SEQ ID NO: 53; (iv) a VL CDR1 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 7; (v) a VL CDR2 having an amino acid sequence that is at least 20%, 25%, 30%, 35%, 40%, 45%, 50%, 55%, 60%, 65%, 70%, 75%, 80%, 85%, 90%, 95% 98%, 99%, or 100% identical to SEQ ID NO: 15; and (vi) a VL CDR3 having an amino acid sequence that is at least 20%, 25%, 30%, 35%, 40%, 45%, 50%, 55%, 60%, 65%, 70%, 75%, 80%, 85%, 90%, 95% 98%, 99%, or 100% identical to SEQ ID NO: 25.

In one instance, the 2ghw-derived antibody or antigen-binding fragment that selectively binds to SARS-Cov-2 can comprise (i) a VH CDR3 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 69; (ii) a VH CDR1 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 40; (ii) a VH CDR2 having an amino acid sequence that is at least 20%, 25%, 30%, 35% 40%, 45% 50%, 55% 60%, 65%, 70%, 75% 80%, 85%, 90%, 95% 98%, 99%, or 100% identical to SEQ ID NO: 54; (iv) a VL CDR1 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 8; (v) a VL CDR2 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 14; and (vi) a VL CDR3 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 26.

In one instance, the 2ghw-derived antibody or antigen-binding fragment that selectively binds to SARS-Cov-2 can comprise (i) a VH CDR3 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 70; (ii) a VH CDR1 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 41; (ii) a VH CDR2 having an amino acid sequence that is at least 20%, 25%, 30%, 35%, 40%, 45%, 50%, 55%, 60%, 65%, 70%, 75%, 80%, 85%, 90%, 95% 98%, 99%, or 100% identical to SEQ ID NO: 55; (iv) a VL CDR1 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to SEQ ID NO: 9; (v) a VL CDR2 having an amino acid sequence that is at least 20%, 25%, 30%, 35%, 40%, 45%, 50%, 55%, 60%, 65%, 70%, 75%, 80%, 85%, 90%, 95% 98%, 99%, or 100% identical to SEQ ID NO: 14; and (vi) a VL CDR3 having an amino acid sequence that is at least 20%, 25%, 30%, 35%, 40%, 45%, 50%, 55%, 60%, 65%, 70%, 75%, 80%, 85%, 90%, 95% 98%, 99%, or 100% identical to SEQ ID NO: 23.

Representative Frameworks (FW) of Antibodies and Antigen-Binding Fragments that Selectively Bind to SARS-Cov-2

A 2ghw-derived antibody or antigen-binding fragment herein that selectively binds to SARS-Cov-2 can comprise an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to one or more of a FW-L1 comprising an amino acid sequence of SEQ ID NO: 1 or 2, a FW-L2 comprising an amino acid sequence of SEQ ID NO: 10 or 11, a FW-L3 comprising an amino acid sequence of any one of any one of SEQ ID NOS: 16-18, a FW-L4 comprising amino acid of SEQ ID NO: 27, a FW-H1 comprising an amino acid sequence of SEQ ID NO: 28, a FW-H2 comprising an amino acid sequence of SEQ ID NO: 42, a FW-H3 comprising an amino acid sequence of SEQ ID NO: 56 or 57, and a FW-H4 comprising an amino acid sequence of SEQ ID NO: 71.

Representative FW-LJ Sequences

In addition to the CDR sequences herein, a 2ghw-derived antibody or antigen-binding fragment herein that selectively binds to SARS-Cov-2 can comprise a VL framework (FW) 1 (FW-L1) having an amino acid sequence of that is at least 20%, 25%, 30%, 35%, 40%, 45%, 50%, 55%, 60%, 65%, 70%, 75%, 80%, 85%, 90%, 95%, 98%, 99%, or 100% identical to any one of the following sequences:

| Clone ID | FW-L1 | SEQ ID NO: |
| --- | --- | --- |
| COVID19_P04_B10 | DIQMTQSPSSLSASVGDRVTITC | 1 |
| COVID19_P04_G03 | DIQMTQSPSSLSASVGDRVTITC | 1 |
| COVID19_P04_G05 | DIQMTQSPSSLSASVGDRVTITC | 1 |
| COVID19_R01_B01 | DIQMTQSPSSLSASVGDRVTITC | 1 |
| COVID19_P04_D08 | DIQMTQSPSSLSASVGDRVTITC | 1 |
| COVID19_P04_B03 | EIVMTQSPATLSVSPGERATLSC | 2 |
| COVID19_P04_B09 | EIVMTQSPATLSVSPGERATLSC | 2 |
| COVID19_P04_E10 | EIVMTQSPATLSVSPGERATLSC | 2 |
| COVID19_R01_A04 | EIVMTQSPATLSVSPGERATLSC | 2 |
| COVID19_R01_D02 | EIVMTQSPATLSVSPGERATLSC | 2 |
| COVID19_R01_B10 | EIVMTQSPATLSVSPGERATLSC | 2 |
| COVID19_R01_C08 | EIVMTQSPATLSVSPGERATLSC | 2 |

Representative FW-L2 Sequences

A 2ghw-derived antibody or antigen-binding fragment herein that selectively binds to SARS-Cov-2 can comprise a FW-L2 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to any one of the following sequences:

| Clone ID | FW-L2 | SEQ ID NO: |
| --- | --- | --- |
| COVID19_P04_B10 | WYQQKPGKAPKLLIY | 10 |
| COVID19_P04_G03 | WYQQKPGKAPKLLIY | 10 |
| COVID19_P04_G05 | WYQQKPGKAPKLLIY | 10 |
| COVID19_R01_B01 | WYQQKPGKAPKLLIY | 10 |
| COVID19_P04_D08 | WYQQKPGKAPKLLIY | 10 |
| COVID19_P04_B03 | WYQQKPGQAPRLLIY | 11 |
| COVID19_P04_B09 | WYQQKPGQAPRLLIY | 11 |
| COVID19_P04_E10 | WYQQKPGQAPRLLIY | 11 |
| COVID19_R01_A04 | WYQQKPGQAPRLLIY | 11 |
| COVID19_R01_D02 | WYQQKPGQAPRLLIY | 11 |
| COVID19_R01_B10 | WYQQKPGQAPRLLIY | 11 |
| COVID19_R01_C08 | WYQQKPGQAPRLLIY | 11 |

Representative FW-L3 Sequences

A 2ghw-derived antibody or antigen-binding fragment herein that selectively binds to SARS-Cov-2 can comprise a FW-L3 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to any one of the following sequences:

| Clone ID | FW-L3 | SEQ ID NO: |
|---|---|---|
| COVID19_P04_B10 | GVPSRFSGSGSGTDFTLTISSLQPEDFATYY | 16 |
| COVID19_P04_G03 | GVPSRFSGSGSGTDFTLTISSLQPEDFATYY | 16 |
| COVID19_P04_G05 | GVPSRFSGSGSGTDFTLTISSLQPEDFATYY | 16 |
| COVID19_R01_B01 | GVPSRFSGSGSGTDFTLTISSLQPEDFATYY | 16 |
| COVID19_P04_D08 | GVPSRFSGSGSGTEFTLTISSLQSEDFAVYY | 17 |
| COVID19_P04_B03 | GIPARFSGSGSGTEFTLTISSLQSEDFAVYY | 18 |
| COVID19_P04_B09 | GIPARFSGSGSGTEFTLTISSLQSEDFAVYY | 18 |
| COVID19_P04_E10 | GIPARFSGSGSGTEFTLTISSLQSEDFAVYY | 18 |
| COVID19_R01-A04 | GIPARFSGSGSGTEFTLTISSLQSEDFAVYY | 18 |
| COVID19_R01_D02 | GIPARFSGSGSGTEFTLTISSLQSEDFAVYY | 18 |
| COVID19_R01_B10 | GIPARFSGSGSGTEFTLTISSLQSEDFAVYY | 18 |
| COVID19_R01_C08 | GIPARFSGSGSGTEFTLTISSLQSEDFAVYY | 18 |

Representative FW-L4 Sequences

A 2ghw-derived antibody or antigen-binding fragment herein that selectively binds to SARS-Cov-2 can comprise FW-L4 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to any one of the following sequences:

| Clone ID | FW-L4 | SEQ ID NO: |
|---|---|---|
| COVID19_P04_B10 | GGGTKVEIKR | 27 |
| COVID19_P04_G03 | GGGTKVEIKR | 27 |
| COVID19_P04_G05 | GGGTKVEIKR | 27 |
| COVID19_R01_B01 | GGGTKVEIKR | 27 |
| COVID19_P04_D08 | GGGTKVEIKR | 27 |
| COVID19_P04_B03 | GGGTKVEIKR | 27 |
| COVID19_P04_B09 | GGGTKVEIKR | 27 |
| COVID19_P04_E10 | GGGTKVEIKR | 27 |
| COVID19_R01_A04 | GGGTKVEIKR | 27 |
| COVID19_R01_D02 | GGGTKVEIKR | 27 |
| COVID19_R01_B10 | GGGTKVEIKR | 27 |
| COVID19_R01_C08 | GGGTKVEIKR | 27 |

Representative FW-H1 Sequences

A 2ghw-derived antibody or antigen-binding fragment herein that selectively binds to SARS-Cov-2 can comprise a VH framework (FW) 1 (FW-H1) having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to any one of the following sequences:

| Clone ID | FW-H1 | SEQ ID NO: |
|---|---|---|
| COVID19_P04_B10 | EVQLVESGGGLVQPGGSLRLSCAASG | 28 |
| COVID19_P04_G03 | EVQLVESGGGLVQPGGSLRLSCAASG | 28 |
| COVID19_P04_G05 | EVQLVESGGGLVQPGGSLRLSCAASG | 28 |
| COVID19 R01_B01 | EVQLVESGGGLVQPGGSLRLSCAASG | 28 |
| COVID19_P04_D08 | EVQLVESGGGLVQPGGSLRLSCAASG | 28 |
| COVID19_P04_B03 | EVQLVESGGGLVQPGGSLRLSCAASG | 28 |
| COVID19_P04_B09 | EVQLVESGGGLVQPGGSLRLSCAASG | 28 |
| COVID19_P04_E10 | EVQLVESGGGLVQPGGSLRLSCAASG | 28 |
| COVID19_R01_A04 | EVQLVESGGGLVQPGGSLRLSCAASG | 28 |
| COVID19_R01_D02 | EVQLVESGGGLVQPGGSLRLSCAASG | 28 |
| COVID19_R01_B10 | EVQLVESGGGLVQPGGSLRLSCAASG | 28 |
| COVID19_R01_C08 | EVQLVESGGGLVQPGGSLRLSCAASG | 28 |

Representative FW-H2 Sequences

A 2ghw-derived antibody or antigen-binding fragment herein that selectively binds to SARS-Cov-2 can comprise a FW-H2 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to any one of the following sequences:

| Clone ID | FW-H2 | SEQ ID NO: |
|---|---|---|
| COVID19_P04_B10 | WVRQAPGKGLEWV | 42 |
| COVID19_P04_G03 | WVRQAPGKGLEWV | 42 |
| COVID19_P04_G05 | WVRQAPGKGLEWV | 42 |
| COVID19_R01_B01 | WVRQAPGKGLEWV | 42 |
| COVID19_P04_D08 | WVRQAPGKGLEWV | 42 |
| COVID19_P04_B03 | WVRQAPGKGLEWV | 42 |
| COVID19_P04_B09 | WVRQAPGKGLEWV | 42 |
| COVID19_P04_E10 | WVRQAPGKGLEWV | 42 |
| COVID19_R01_A04 | WVRQAPGKGLEWV | 42 |
| COVID19_R01_D02 | WVRQAPGKGLEWV | 42 |
| COVID19_R01_B10 | WVRQAPGKGLEWV | 42 |
| COVID19_R01_C08 | WVRQAPGKGLEWV | 42 |

Representative FW-H3 Sequences

A 2ghw-derived antibody or antigen-binding fragment herein that selectively binds to SARS-Cov-2 can comprise a FW-H3 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to any one of the following sequences:

| Clone ID | FW-H3 | SEQ ID NO: |
|---|---|---|
| COVID19_P04_B10 | DSVKGRFTISRDNSKNTLYLQMNSLRAEDTAVYY | 56 |
| COVID19_P04_G03 | DSVKGRFTISRDNSKNTLYLQMNSLRAEDTAVYY | 56 |
| COVID19_P04_G05 | DSVKGRFTISRDNSKNTLYLQMNSLRAEDTAVYY | 56 |
| COVID19_R01_B01 | DSVKGRFTISRDNSKNTLYLQMNSLRAEDTAVYY | 56 |
| COVID19_P04_D08 | DSVKGRFTISRDNSKNTLYLQMNSLRAEDTAVYY | 56 |
| COVID19_P04_B03 | DSVKGRFTISRDNSKNTLYLQMNSLRAEDTAVYY | 56 |
| COVID19_P04_B09 | DSVKGRFTISRDNSKNTLYLQMNSLRAEDTAVYY | 56 |
| COVID19_P04_E10 | DSVKGRFTISRDNSKNTLYLQMNSLRAEDTAVYY | 56 |
| COVID19_R01_A04 | DSVKGRFTISRDNSKNTLYLQMNNLRAEDTAVYY | 57 |
| COVID19_R01_D02 | DSVKGRFTISRDNSKNTLYLQMNSLRAEDTAVYY | 56 |
| COVID19_R01_B10 | DSVKGRFTISRDNSKNTLYLQMNSLRAEDTAVYY | 56 |
| COVID19_R01_C08 | DSVKGRFTISRDNSKNTLYLQMNSLRAEDTAVYY | 56 |

Representative FW-H4 Sequences

A 2ghw-derived antibody or antigen-binding fragment herein that selectively binds to SARS-Cov-2 can comprise a FW-H4 having an amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to any one of the following sequences:

| Clone ID | FW-H4 | SEQ ID NO: |
|---|---|---|
| COVID19_P04_B10 | GQGTLVTVSS | 71 |
| COVID19_P04_G03 | GQGTLVTVSS | 71 |
| COVID19_P04_G05 | GQGTLVTVSS | 71 |
| COVID19_R01_B01 | GQGTLVTVSS | 71 |
| COVID19_P04_D08 | GQGTLVTVSS | 71 |
| COVID19_P04_B03 | GQGTLVTVSS | 71 |
| COVID19_P04_B09 | GQGTLVTVSS | 71 |
| COVID19_P04_E10 | GQGTLVTVSS | 71 |
| COVID19_R01_A04 | GQGTLVTVSS | 71 |
| COVID19_R01_D02 | GQGTLVTVSS | 71 |
| COVID19_R01_B10 | GQGTLVTVSS | 71 |
| COVID19_R01_C08 | GQGTLVTVSS | 71 |

Representative VH and VL Sequences that Selectively Bind to SARS-Cov-2

A 2ghw-derived antibody or antigen-binding fragment herein that selectively binds to SARS-Cov-2 can have a variable heavy (VH) chain amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to any one of the following sequences:

| Clone ID | VH | SEQ ID NO: |
|---|---|---|
| COVID19_P04_B10 | EVQLVESGGGLVQPGGSLRLSCAASGFRFSDAAIHWVRQAPGKGLEWVSAISGSGGSTYYADSVKGRFTISRDNSKNTLYLQMNSLRAEDTAVYYCARDRSYGIDYWGQGTLVTVSS | 72 |
| COVID19_P04_G03 | EVQLVESGGGLVQPGGSLRLSCAASGFTVSSNYMNWVRQAPGKGLEWVSVVYPGGSTYYADSVKGRFTISRDNSKNTLYLQMNSLRAEDTAVYYCARDRSYYLDYWGQGTLVTVSS | 73 |
| COVID19_P04_G05 | EVQLVESGGGLVQPGGSLRLSCAASGLSVTSNYMSWVRQAPGKGLEWVSVIYPGGSTFYADSVKGRFTISRDNSKNTLYLQMNSLRAEDTAVYYCARDRSYYLDYWGQGTLVTVSS | 74 |
| COVID19_R01_B01 | EVQLVESGGGLVQPGGSLRLSCAASGFTFASHAMSWVRQAPGKGLEWVSGISSDGSITTYADSVKGRFTISRDNSKNTLYLQMNSLRAEDTAVYYCARDRGWYLDYWGQGTLVTVSS | 75 |
| COVID19_P04_D08 | EVQLVESGGGLVQPGGSLRLSCAASGFTFTNYAMTWVRQAPGKGLEWVSTMSNIGGDTYYADSVKGRFTISRDNSKNTLYLQMNSLRAEDTAVYYCARDRRVYLDYWGQGTLVTVSS | 76 |
| COVID19_P04_B03 | EVQLVESGGGLVQPGGSLRLSCAASGFTFSNHYMSWVRQAPGKGLEWVSAISGSGGSTYYADSVKGRFTISRDNSKNTLYLQMNSLRAEDTAVYYCARDRSYYLDYWGQGTLVTVSS | 77 |
| COVID19_P04_B09 | EVQLVESGGGLVQPGGSLRLSCAASGFTFSNSDMNWVRQAPGKGLEWVSAISGTGDTTEYADSVKGRFTISRDNSKNTLYLQMNSLRAEDTAVYYCARDRSLMLDYWGQGTLVTVSS | 78 |
| COVID19_P04_E10 | EVQLVESGGGLVQPGGSLRLSCAASGFSFSSYGMSWVRQAPGKGLEWVSAMNRDGSYIYYADSVKGRFTISRDNSKNTLYLQMNSLRAEDTAVYYCARDRSYVGYWGQGTLVTVSS | 79 |

| Clone ID | VH | SEQ ID NO: |
|---|---|---|
| COVID19_R01_A04 | EVQLVESGGGLVQPGGSLRLSCAASGFTFSDHYMSWVRQAPGKGLEWVSAISTSGDSTFYADSVKGRFTISRDNSKNTLYLQMNNLRAEDTAVYYCARDRSYYLDYWGQGTLVTVSS | 80 |
| COVID19_R01_D02 | EVQLVESGGGLVQPGGSLRLSCAASGFTFDDYAMHWVRQAPGKGLEWVAIIYEGGSPHYADSVKGRFTISRDNSKNTLYLQMNSLRAEDTAVYYCARDRSGYLDYWGQGTLVTVSS | 81 |
| COVID19_R01_B10 | EVQLVESGGGLVQPGGSLRLSCAASGFTVSSNYMSWVRQAPGKGLEWVSVIYPGGSTFYADSVKGRFTISRDNSKNTLYLQMNSLRAEDTAVYYCARDRSYYLDYWGQGTLVTVSS | 82 |
| COVID19_R01_C08 | EVQLVESGGGLVQPGGSLRLSCAASGFSFSSYGMSWVRQAPGKGLEWVSAMNRDGSYIYYADSVKGRFTISRDNSKNTLYLQMNSLRAEDTAVYYCARDRSYVGYWGQGTLVTVSS | 83 |

A 2ghw-derived antibody or antigen-binding fragment herein and that selectively binds to SARS-Cov-2 can have a variable light (VL) chain amino acid sequence that is at least 20%, 25%, 30%, 35%, 40%, 45%, 50%, 55%, 60%, 65%, 70%, 75%, 80%, 85%, 90%, 95%, 98%, 99%, or 100% identical to any of the following sequences:

| Clone ID | VL | SEQ ID NO: |
|---|---|---|
| COVID19_P04_B10 | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGGGTKVEIKR | 84 |
| COVID19_P04_G03 | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGGGTKVEIKR | 85 |
| COVID19_P04_G05 | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGGGTKVEIKR | 86 |
| COVID19_R01_B01 | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGGGTKVEIKR | 87 |
| COVID19_P04_D08 | DIQMTQSPSSLSASVGDRVTITCRASQSISSYLNWYQQKPGKAPKLLIYAASSLQSGVPSRFSGSGSGTEFTLTISSLQSEDFAVYYCQQYGSSPLTFGGGTKVEIKR | 88 |
| COVID19_P04_B03 | EIVMTQSPATLSVSPGERATLSCRASQSIGTYLSWYQQKPGQAPRLLIYGASTRATGIPARFSGSGSGTEFTLTISSLQSEDFAVYYCQQSLSLPVTFGGGTKVEIKR | 89 |
| COVID19_P04_B09 | EIVMTQSPATLSVSPGERATLSCRASQSVRSNLAWYQQKPGQAPRLLIYGASTRATGIPARFSGSGSGTEFTLTISSLQSEDFAVYYCQQRNNWPPTFGGGTKVEIKR | 90 |
| COVID19_P04_E10 | EIVMTQSPATLSVSPGERATLSCRASQSVRSNLAWYQQKPGQAPRLLIYGASTRATGIPARFSGSGSGTEFTLTISSLQSEDFAVYYCQQRNNWPPTFGGGTKVEIKR | 91 |
| COVID19_R01_A04 | EIVMTQSPATLSVSPGERATLSCRASQSVRSNLAWYQQKPGQAPRLLIYGASTRATGIPARFSGSGSGTEFTLTISSLQSEDFAVYYCQQFGTSPPGLSFGGGTKVEIKR | 92 |
| COVID19_R01_D02 | EIVMTQSPATLSVSPGERATLSCRASQSVSNNLAWYQQKPGQAPRLLIYDASTRATGIPARFSGSGSGTEFTLTISSLQSEDFAVYYCQQYNNWPPTFGGTKVEIKR | 93 |
| COVID19_R01_B10 | EIVMTQSPATLSVSPGERATLSCRASQSVSSSYLAWYQQKPGQAPRLLIYGASTRATGIPARFSGSGSGTEFTLTISSLQSEDFAVYYCQQASSTPLTFGGGTKVEIKR | 94 |
| COVID19_R01_C08 | EIVMTQSPATLSVSPGERATLSCRASQSVSSNLAWYQQKPGQAPRLLIYGASTRATGIPARFSGSGSGTEFTLTISSLQSEDFAVYYCQQRNNWPPTFGGTKVEIKR | 95 |

In one instance, a 2ghw-derived antibody or antigen-binding fragment, described herein that selectively binds to SARS-Cov-2 can comprise an VH having an amino acid sequence that is at least 70%, 75%, 80%, 85%, 90%, 95%, 98%, 99%, or 100% identical to SEQ ID NO: 72 an VL having an amino acid sequence that is at least 70%, 75%, 80%, 85%, 90%, 95%, 98%, 99%, or 100% identical to SEQ ID NO: 84.

In one instance, a 2ghw-derived antibody or antigen-binding fragment, described herein that selectively binds to SARS-Cov-2 can comprise an VH having an amino acid sequence that is at least 70%, 75%, 80%, 85%, 90%, 95%, 98%, 99%, or 100% identical to SEQ ID NO: 73 an VL having an amino acid sequence that is at least 70%, 75%, 80%, 85%, 90%, 95%, 98%, 99%, or 100% identical to SEQ ID NO: 85.

In one instance, a 2ghw-derived antibody or antigen-binding fragment, described herein that selectively binds to SARS-Cov-2 can comprise an VH having an amino acid sequence that is at least 70%, 75%, 80%, 85%, 90%, 95%, 98%, 99%, or 100% identical to SEQ ID NO: 74 an VL having an amino acid sequence that is at least 70%, 75%, 80%, 85%, 90%, 95%, 98%, 99%, or 100% identical to SEQ ID NO: 86.

In one instance, a 2ghw-derived antibody or antigen-binding fragment, described herein that selectively binds to SARS-Cov-2 can comprise an VH having an amino acid sequence that is at least 70%, 75%, 80%, 85%, 90%, 95%, 98%, 99%, or 100% identical to SEQ ID NO: 75 an VL having an amino acid sequence that is at least 70%, 75%, 80%, 85%, 90%, 95%, 98%, 99%, or 100% identical to SEQ ID NO: 87.

In one instance, a 2ghw-derived antibody or antigen-binding fragment, described herein that selectively binds to SARS-Cov-2 can comprise an VH having an amino acid sequence that is at least 70%, 75%, 80%, 85%, 90%, 95%, 98%, 99%, or 100% identical to SEQ ID NO: 76 an VL having an amino acid sequence that is at least 70%, 75%, 80%, 85%, 90%, 95%, 98%, 99%, or 100% identical to SEQ ID NO: 88.

In one instance, a 2ghw-derived antibody or antigen-binding fragment, described herein that selectively binds to SARS-Cov-2 can comprise an VH having an amino acid sequence that is at least 70%, 75%, 80%, 85%, 90%, 95%, 98%, 99%, or 100% identical to SEQ ID NO: 77 an VL having an amino acid sequence that is at least 70%, 75%, 80%, 85%, 90%, 95%, 98%, 99%, or 100% identical to SEQ ID NO: 89.

In one instance, a 2ghw-derived antibody or antigen-binding fragment, described herein that selectively binds to SARS-Cov-2 can comprise an VH having an amino acid sequence that is at least 70%, 75%, 80%, 85%, 90%, 95%, 98%, 99%, or 100% identical to SEQ ID NO: 78 an VL having an amino acid sequence that is at least 70%, 75%, 80%, 85%, 90%, 95%, 98%, 99%, or 100% identical to SEQ ID NO: 90.

In one instance, a 2ghw-derived antibody or antigen-binding fragment, described herein that selectively binds to SARS-Cov-2 can comprise an VH having an amino acid sequence that is at least 70%, 75%, 80%, 85%, 90%, 95%, 98%, 99%, or 100% identical to SEQ ID NO: 79 an VL having an amino acid sequence that is at least 70%, 75%, 80%, 85%, 90%, 95%, 98%, 99%, or 100% identical to SEQ ID NO: 91.

In one instance, a 2ghw-derived antibody or antigen-binding fragment, described herein that selectively binds to SARS-Cov-2 can comprise an VH having an amino acid sequence that is at least 70%, 75%, 80%, 85%, 90%, 95%, 98%, 99%, or 100% identical to SEQ ID NO: 80 an VL having an amino acid sequence that is at least 70%, 75%, 80%, 85%, 90%, 95%, 98%, 99%, or 100% identical to SEQ ID NO: 92.

In one instance, a 2ghw-derived antibody or antigen-binding fragment, described herein that selectively binds to SARS-Cov-2 can comprise an VH having an amino acid sequence that is at least 70%, 75%, 80%, 85%, 90%, 95%, 98%, 99%, or 100% identical to SEQ ID NO: 81 an VL having an amino acid sequence that is at least 70%, 75%, 80%, 85%, 90%, 95%, 98%, 99%, or 100% identical to SEQ ID NO: 93.

In one instance, a 2ghw-derived antibody or antigen-binding fragment, described herein that selectively binds to SARS-Cov-2 can comprise an VH having an amino acid sequence that is at least 70%, 75%, 80%, 85%, 90%, 95%, 98%, 99%, or 100% identical to SEQ ID NO: 82 an VL having an amino acid sequence that is at least 70%, 75%, 80%, 85%, 90%, 95%, 98%, 99%, or 100% identical to SEQ ID NO: 94.

In one instance, a 2ghw-derived antibody or antigen-binding fragment, described herein that selectively binds to SARS-Cov-2 can comprise an VH having an amino acid sequence that is at least 70%, 75%, 80%, 85%, 90%, 95%, 98%, 99%, or 100% identical to SEQ ID NO: 83 an VL having an amino acid sequence that is at least 70%, 75%, 80%, 85%, 90%, 95%, 98%, 99%, or 100% identical to SEQ ID NO: 95.

Modified Antibodies

The present disclosure provides for modified antibodies. Modified antibodies can comprise antibodies which have one or more modifications which can enhance their activity, binding, specificity, selectivity, or another feature. In one aspect, the present disclosure provides for modified antibodies (which can be heteromultimers) that comprise an anti-SARS-Cov-2 antibody as described herein. Reference to a modified antibody herein also refers to a modified antigen-binding fragment.

A modified antibody can comprise a bispecific modified antibody, a trispecific modified antibody or antigen-binding fragment, or a tetraspecific modified antibody or antigen-binding fragment. A bispecific modified antibody can be able to specifically bind to 2 targets. In some cases, one of the targets a bispecific modified antibody can specifically bind to can be a SARS-Cov-2. A trispecific modified antibody can be able to specifically bind to 3 targets. In some cases, one of the targets a trispecific modified antibody can specifically bind to can be a SARS-Cov-2. A tetraspecific modified antibody can be able to specifically bind to 4 targets. In some cases, one of the targets a tetraspecific modified antibody can specifically bind to can be a SARS-Cov-2.

A modified antibody can comprise a human modified antibody. Also included herein are amino acid sequence variants of the modified antibody which can be prepared by introducing appropriate nucleotide changes into the modified antibody DNA, or by synthesis of the desired modified antibody polypeptide. Such variants include, for example, deletions from, or insertions or substitutions of, residues within the amino acid sequences of the first and second polypeptides forming the modified antibody. Any combination of deletion, insertion, and substitution is made to arrive at the final construct, provided that the final construct possesses the desired antigen-binding characteristics. The amino acid changes also may alter post-translational processes of the modified antibody, such as changing the number or position of glycosylation sites.

"Alanine scanning mutagenesis" can be a useful method for identification of certain residues or regions of the modified antibody polypeptides that might be preferred locations for mutagenesis. Here, a residue or group of target residues are identified (e.g., charged residues such as Arg, Asp, His, Lys, and Glu) and replaced by a neutral or negatively charged amino acid (for example, alanine or polyalanine) to affect the interaction of the amino acids with the surrounding aqueous environment in or outside the cell. Those domains demonstrating functional sensitivity to the substitutions then are refined by introducing further or other variants at or for the sites of substitution. Thus, while the site for introducing an amino acid sequence variation is predetermined, the nature of the mutation per se need not be predetermined.

Normally the mutations can involve conservative amino acid replacements in non-functional regions of the modified antibody. Exemplary mutations are shown below.

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Covalent modifications of antibody, antigen-binding fragment, or modified antibody polypeptides are included within the scope of this disclosure. Covalent modifications of the modified antibody can be introduced into the molecule by reacting targeted amino acid residues of the modified antibody or fragments thereof with an organic derivatizing agent that can be capable of reacting with selected side chains or the N- or C-terminal residues. Another type of covalent modification of the modified antibody polypeptide can comprise altering the native glycosylation pattern of the polypeptide. Herein, "altering" can mean deleting one or more carbohydrate moieties found in the original modified antibody, and/or adding one or more glycosylation sites that are not present in the original modified antibody. Addition of glycosylation sites to the modified antibody polypeptide can be accomplished by altering the amino acid sequence such that it contains one or more N-linked glycosylation sites. The alteration may also be made by the addition of, or substitution by, one or more serine or threonine residues to the original modified antibody sequence (for O-linked glycosylation sites). For ease, the modified antibody amino acid sequence can be altered through changes at the DNA level, particularly by mutating the DNA encoding the modified antibody polypeptide at preselected bases such that codons are generated that will translate into the desired amino acids. Another means of increasing the number of carbohydrate moieties on the modified antibody polypeptide is by chemical or enzymatic coupling of glycosides to the polypeptide. Removal of carbohydrate moieties present on the modified antibody can be accomplished chemically or enzymatically.

Another type of covalent modification of modified antibody comprises linking the modified antibody polypeptide to one of a variety of non-proteinaceous polymers, e.g., polyethylene glycol, polypropylene glycol, or polyoxyalkylenes.

Methods for complexing binding agents or the antibody or antigen-binding fragments herein with another agent are known in the art. Such methods may utilize one of several available heterobifunctional reagents used for coupling or linking molecules.

In one instance, Fc portions of antibodies can be modified to increase half-life of the molecule in the circulation in blood when administered to a subject.

Additionally, antibodies may be produced or expressed so that they do not contain fucose on their complex N-glycoside-linked sugar chains to increase effector functions. Similarly, antibodies can be attached at their C-terminal end to all or part of an immunoglobulin heavy chain derived from any antibody isotype, e.g., IgG, IgA, IgE, IgD, and IgM and any of the isotype sub-classes, e.g., IgG1, IgG2b, IgG2a, IgG3, and IgG4.

Glycosylation of immunoglobulins has been shown to have significant effects on their effector functions, structural stability, and rate of secretion from antibody-producing cells. Antibodies and antigen-binding fragments herein may be glycosylated. Glycosylation at a variable domain framework residue can alter the binding interaction of the antibody with antigen. The present disclosure includes criteria by which a limited number of amino acids in the framework or CDRs of an immunoglobulin chain can be chosen to be mutated (e.g., by substitution, deletion, and/or addition of residues) in order to increase the affinity of an antibody.

Linkers for conjugating antibodies to other moieties are within the scope of the present disclosure. Associations (binding) between antibodies and labels include, but are not limited to, covalent and non-covalent interactions, chemical conjugation, as well as recombinant techniques.

Antibodies, or antigen-binding fragments thereof, can be modified for various purposes such as, for example, by addition of polyethylene glycol (PEG). PEG modification (PEGylation) can lead to one or more of improved circulation time, improved solubility, improved resistance to proteolysis, reduced antigenicity and immunogenicity, improved bioavailability, reduced toxicity, improved stability, and easier formulation.

An antibody or antigen-binding fragment can be conjugated to, or recombinantly engineered with, an affinity tag (e.g., a purification tag). Affinity tags such as, for example, His6 tags (His-His-His-His-His-His) (SEQ ID NO: 104) have been described.

Since it is often difficult to predict in advance the characteristics of a variant modified antibody, it will be appreciated that some screening of the recovered variants may be needed to select an optimal variant. Exemplary methods of screening the recovered variants are described below in the Examples.

Methods of Expressing Antibodies

Also provided herein are methods of making any of these antibodies or polypeptides. The polypeptides can be produced by proteolytic or other degradation of the antibodies, by recombinant methods (i.e., single or fusion polypeptides) as described above, or by chemical synthesis. Polypeptides of the antibodies, especially shorter polypeptides up to about 50 amino acids, can be made by chemical synthesis. Methods of chemical synthesis are commercially available. For example, an antibody could be produced by an automated polypeptide synthesizer employing a solid phase method.

Antibodies may be made recombinantly by first isolating the antibodies and antibody producing cells from host animals, obtaining the gene sequence, and using the gene sequence to express the antibody recombinantly in host cells (e.g., CHO cells). Another method which may be employed is to express the antibody sequence in plants (e.g., tobacco) or transgenic milk. Methods for expressing antibodies recombinantly in plants or milk have been disclosed. Methods for making derivatives of antibodies, e.g., single chain, etc. are also within the scope of the present disclosure.

As used herein, "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected with a polynucleotide(s) of this disclosure.

DNA encoding an antibody may be readily isolated and sequenced using conventional procedures (e.g., by using oligonucleotide probes that are capable of binding specifically to genes encoding the heavy and light chains of the monoclonal antibodies). Hybridoma cells may serve as a source of such DNA. Once isolated, the DNA may be placed into one or more expression vectors (such as expression vectors disclosed in PCT Publication No. WO 87/04462), which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, or by covalently joining to the immunoglobulin coding sequence all or part of the coding sequence for a non-immunoglobulin polypeptide. In that manner, "chimeric" or "hybrid" antibodies are prepared that have the binding specificity of an antibody herein.

Contemplated herein are vectors that encode the one or more antibodies or antigen-binding fragments herein. As used herein, "vector" means a construct, which is capable of delivering, and possibly expressing, one or more gene(s) or sequence(s) of interest in a host cell. Examples of vectors include, but are not limited to, viral vectors; naked DNA or RNA expression vectors; plasmid, cosmid, or phage vectors; DNA or RNA expression vectors associated with cationic condensing agents; DNA or RNA expression vectors encapsulated in liposomes; and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed. An expression vector can be used to direct expression of an antibody. Expression vectors can be administered to obtain expression of an exogenous protein in vivo.

For high level production, a widely used mammalian expression system is one which utilizes Lonza's GS Gene Expression System™. This system uses a viral promoter and selection via glutamine metabolism to provide development of high-yielding and stable mammalian cell lines.

For alternative high-level production, a widely used mammalian expression system is one which utilizes gene amplification by dihydrofolate reductase deficient ("dhfr") Chinese hamster ovary cells. The system is based upon the dihydrofolate reductase "dhfr" gene, which encodes the DHFR enzyme, which catalyzes conversion of dihydrofolate to tetrahydrofolate. In order to achieve high production, dhfr-CHO cells are transfected with an expression vector containing a functional DHFR gene, together with a gene that encodes a desired protein. In this case, the desired protein is recombinant antibody heavy chain and/or light chain.

By increasing the amount of the competitive DHFR inhibitor methotrexate (MTX), the recombinant cells develop resistance by amplifying the dhfr gene. In standard cases, the amplification unit employed is much larger than the size of the dhfr gene, and as a result the antibody heavy chain is co-amplified.

When large scale production of the protein, such as the antibody chain, is desired, both the expression level and the stability of the cells being employed are taken into account.

The present application provides one or more isolated polynucleotides (nucleic acids) encoding a 2ghw-derived antibody or antigen-binding fragment herein, vectors containing such polynucleotides, and host cells and expression systems for transcribing and translating such polynucleotides into polypeptides.

The present application also provides constructs in the form of plasmids, vectors, transcription or expression cassettes which comprise at least one polynucleotide as above.

The present application also provides a recombinant host cell which comprises one or more constructs as above. A nucleic acid encoding any antibody or antigen-binding fragment herein forms an aspect of the present application, as does a method of production of the antibody, which method comprises expression from encoding nucleic acid therefrom. Expression can be achieved by culturing under appropriate conditions recombinant host cells containing the nucleic acid. Following production by expression, an antibody or a portion thereof can be isolated and/or purified using any suitable technique, then used as appropriate.

Systems for cloning and expression of a polypeptide in a variety of different host cells are contemplated for use herein.

A further aspect provides a host cell containing nucleic acid as disclosed herein using any suitable method. A still further aspect provides a method comprising introducing such nucleic acid into a host cell. The introduction can be followed by causing or allowing expression from the nucleic acid, e.g., by culturing host cells under conditions for expression of the gene.

One or more polynucleotides encoding a 2ghw-derived antibody or an antigen-binding fragment can be prepared recombinantly/synthetically in addition to, or rather than, cloned. In a further embodiment, the full DNA sequence of the recombinant DNA molecule or cloned gene(s) of a 2ghw-derived antibody or antigen-binding fragment herein can be operatively linked to an expression control sequence which can be introduced into an appropriate host using any suitable method.

Nucleic acid sequences can be expressed by operatively linking them to an expression control sequence in an appropriate expression vector and employing that expression vector to transform an appropriate host cell. Any of a wide variety of expression control sequences—sequences that control the expression of a nucleic acid sequence operatively linked to it—can be used in these vectors to express the nucleic acid sequences.

A wide variety of host/expression vector combinations can be employed in expressing the nucleic acid sequences of this disclosure. It will be understood that not all vectors, expression control sequences, and hosts will function equally well to express the nucleic acid sequences. Neither will all hosts function equally well with the same expression system. In some embodiments, in selecting a vector, the host is considered such that the vector can function in it. The vector's copy number, the ability to control that copy number, and the expression of any other proteins encoded by the vector, such as antibiotic markers, may also be considered. In certain embodiments, in selecting a vector, the host is considered such that the vector functions in it. The vector's copy number, the ability to control that copy number, and the expression of any other proteins encoded by the vector, such as antibiotic markers, can also be considered.

The present application also provides a method which comprises using a construct as stated above in an expression system in order to express the antibodies (or portions thereof) as above. Considering these and other factors, a variety of vector/expression control sequence/host combinations can be constructed that can express the nucleic acid sequences on fermentation or in large scale animal culture.

Simultaneous incorporation of the antibody (or portion thereof)-encoding nucleic acids and the selected amino acid position changes can be accomplished by a variety of suitable methods including, for example, recombinant and chemical synthesis.

Provided herein are methods of expressing an antibody or antigen-binding fragment antigen-binding that can selectively bind to SARS-Cov-2 in a subject comprising administering to the subject a composition comprising one or more polynucleotides (e.g., mRNA) encoding the antibody or antigen-binding fragment.

In some cases, administering the one or more polynucleotides to the subject can comprise enteral, gastroenteral, oral, transdermal, epicutaneous, intradermal, subcutaneous, nasal administration, intravenous, intraperitoneal, intraarterial, intramuscular, intraosseous infusion, transmucosal, insufflation, or sublingual administration. In some cases, a polynucleotide can be administered via more than one route.

Antibodies or antigen-binding fragments can be synthesized in the subject based at least in part on the polynucleotide encoding the antibody or antigen-binding fragment. For example, a polynucleotide can enter a cell of the subject, and the antibody or antigen-binding fragment can be synthesized at least in part by using the subject's cellular transcription and/or translation machinery. In some cases, for example where the polynucleotide is an mRNA molecule, the antibody or antigen-binding fragment can be synthesized at least in part by using the subject's cellular translation machinery (e.g., ribosomes, tRNA, etc.). In some cases, antibody or antigen-binding fragments can be transported from a cell to the plasma of the subject after translation.

Compositions

Compositions comprising a 2ghw-derived antibody or antigen-binding fragment herein may be prepared for storage by mixing an antibody or antigen-binding fragment having the desired degree of purity with optional pharmaceutically acceptable carriers, excipients or stabilizers (Remington, The Science and Practice of Pharmacy 20th Ed. Mack Publishing (2000)), in the form of lyophilized formulations or aqueous solutions.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline. Compositions comprising such carriers are formulated by well-known conventional methods (see, for example, Remington's Pharmaceutical Sciences, 18th edition, A. Gennaro, Ed., Mack Publishing Co., Easton, Pa., 1990; and Remington, The Science and Practice of Pharmacy 20th Ed. Mack Publishing, 2000).

Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The compositions to be used for in vivo administration may be sterilized. This may be accomplished by, for example, filtration through sterile filtration membranes, or any other art-recognized method for sterilization. Antibody compositions are generally placed into a container having a sterile access port, for example, an intravenous solution bag or vial having a stopper pierceable by a hypodermic injection needle. Other methods for sterilization and filtration are known in the art and are contemplated herein.

In one embodiment of the present invention, the compositions are formulated to be free of pyrogens such that they are acceptable for administration to a subject.

The compositions according to the present invention may be in unit dosage forms such as solutions or suspensions, tablets, pills, capsules, powders, granules, or suppositories, etc., for intravenous, oral, parenteral or rectal administration, or administration by inhalation or insufflation.

The phrase "pharmaceutically acceptable" refers to molecular entities and compositions that are physiologically tolerable and do not typically produce an allergic or similar untoward reaction, such as gastric upset, dizziness and the like, when administered to a subject.

In some instances, an antibody or antigen-binding fragment can be bound to one or more carriers. Carriers can be active and/or inert. Examples of well-known carriers include polypropylene, polystyrene, polyethylene, dextran, nylon, amylases, glass, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation.

One embodiment contemplates the use of the antibodies and antigen-binding fragments to manufacture a medicament for treating a condition, disease or disorder described herein. Medicaments can be formulated based on the physical characteristics of the subject needing treatment, and can be formulated in single or multiple formulations based on the stage of the condition, disease or disorder. Medicaments can be packaged in a suitable package with appropriate labels for the distribution to hospitals and clinics wherein the label is for the indication of treating a subject having a disease described herein. Medicaments can be packaged as a single or multiple units. Instructions for the dosage and administration of the compositions can be included with the packages as described below. The invention is further directed to medicaments of an antibody or antigen-binding fragment and a pharmaceutically acceptable carrier.

Kits

Provided herein are kits that comprise one or more anti-SARS-Cov-2 antibodies or antigen-binding fragments herein. Provided herein is a container means comprising one or more anti-SARS-Cov-2 antibodies or antigen-binding fragments herein. The container means may be any suitable container which may house a liquid or lyophilized composition including, but not limited to, a vial, a syringe, a bottle, an intravenous (IV) bag, an ampoule, or any other suitable container. A syringe may be able to hold any volume of liquid suitable for injection into a subject including, but not limited to, 0.5 cc, 1 cc, 2 cc, 5 cc, 10 cc or more. In some embodiments, the antibody or antigen-binding fragment is lyophilized, and the kit comprises one or more suitable buffers for reconstitution prior to injection.

The kit may comprise one or more instruction sheets describing the use of the one or more antibodies or antigen-binding fragments. The kit may include one or more labels describing the contents and use of the one or more antibodies.

Methods of Prevention or Treatment

The present disclosure provides methods of preventing or treating a subject infected with SARS-Cov-2 (COVID) or suspected of being infected with SARS-Cov-2 in a subject in need thereof, comprising administering to the subject a 2ghw-derived antibody or antigen-binding fragment herein. In one instance, the subject to be treated is symptomatic prior to administration of the antibody. In another instance, the subject to be treated is asymptomatic prior to administration of the antibody.

The present disclosure provides methods of prophylactically treating (e.g., preventing) a subject having one or more co-morbidities or having an increased or high risk of infection.

A "subject" as described herein, includes, but is not limited to, a human, a rodent, a primate, etc. In some instances, the subject to be treated exhibits one or more underlying conditions that exacerbate the infection such as, for example, high blood pressure, heart problems, diabetes, immunocompromised, lung disease, cancer, clots, thrombosis, or a combination thereof.

A subject can be administered a 2ghw-derived antibody or antigen-binding fragment herein in an amount that achieves at least partially a partial or complete reduction of one or more symptoms. Reduction can be, for example, a decrease of one or more symptoms by about 5% or more compared to prior to treatment. For the administration to human patients, the compositions can be formulated by methodology known by one in the art. The amount of an antibody necessary to bring about therapeutic treatment of COVID19 is not fixed per se. The amount of antibody administered may vary with the extensiveness of the disease and size of the human suffering from COVID19. Treatment, in one instance, lowers infection rates in a population of subjects. Treatment may also result in a shortened recovery time, in fewer symptoms, or in less severe symptoms, or a combination thereof compared to an untreated subject who has COVID19.

The 2ghw-derived antibodies and antigen-binding fragments herein may be used to treat a COVID19 infection (an infection caused by SARS-Cov-2) in a subject in need thereof, thereby reducing one or more symptoms of the infection. The one or more symptoms to be treated include, but are not limited to, a fever of over 100.4° F., fatigue, coughing (e.g., a dry cough), aches, pains, runny nose, stuffy nose, sore throat, diarrhea, headaches, shortness of breath, or any combination thereof. In some instances, treatment of a subject includes a reduction by at least 5% in 1 symptom, 2 symptoms, 3 symptoms, 4 symptoms, 5 symptoms, 6 symptoms, 7 symptoms, 8 symptoms, 9 symptoms, 10 symptoms, or 11 symptoms. During at least a portion of this time period the antibody or antigen-binding fragment can protect the subject from infection by SARS-Cov-2. Protecting can comprise for example reducing an infection rate of SARS-Cov-2 or reducing or preventing reproduction of SARS-Cov-2. Treatment can comprise for example reducing symptoms of COVID-19, reducing a death rate, or reducing or preventing reproduction of SARS-Cov-2.

"Administering" is referred to herein as providing one or more compositions to a patient in a manner that results in the composition being inside the patient's body. Such an administration can be by any route including, without limitation, locally, regionally, or systemically, by subcutaneous, intradermal, intravenous, intra-arterial, intraperitoneal, or intramuscular administration (e.g., injection). In one instance, administration is via intradermal injection. In another instance, administration is via subcutaneous injection. In one embodiment, a subject is administered one of the antibodies or antigen-binding fragments herein one or more times. In another embodiment, a subject is administered two of the antibodies or antigen-binding fragments herein one or more times. In another embodiment, a subject is administered three of the antibodies or antigen-binding fragments herein one or more times. In another embodiment, a subject is administered four of the antibodies or antigen-binding fragments herein one or more times. A 2ghw-derived antibody or antigen-binding fragment herein to be administered to the subject exhibits a nM or a pM binding affinity, e.g., between 50 nM and 700 pM.

The present disclosure provides methods of reducing the death rate of infection by SARS-Cov-2 by administering to a subject in need thereof a composition comprising one or more polynucleotides (e.g., mRNA) encoding an antibody or antigen-binding fragment that can specifically bind to SARS-Cov-2. Reduction in death rate can be determined for example by comparing the rate of death of subjects infected by SARS-Cov-2 between a cohort that receives the composition and a cohort that does not receive the composition. Death rate can be determined for example by determining the number of infected subjects of a cohort wherein infection by SARS-Cov-2 results in death. In some cases, the death rate can be reduced compared with subjects not administered a composition comprising an mRNA molecule provided herein by at least 5%, at least 10%, at least 20%, at least 30%, at least 40%, at least 50%, at least 60%, at least 70%, at least 80%, or at least 90%. In some cases, the death rate can be reduced compared with subjects not administered a composition comprising an mRNA molecule provided herein by about 10%, about 20%, about 30%, about 40%, about 50%, about 60%, about 70%, about 80%, about 90%, or a range between any two foregoing values.

The present disclosure also provides methods for reducing the infection rate of SARS-Cov-2 by administering to a subject non infected with SARS-Cov-2 a composition comprising one or more polynucleotides (e.g., mRNA) encoding an antibody or antigen-binding fragment that can specifically bind to SARS-Cov-2. Reduction in infection rate can be determined for example by comparing the rate of infection of subjects exposed to SARS-Cov-2 between a cohort that receives the composition and a cohort that does not receive the composition. Infection of a subject can be determined by analyzing a sample from the subject for the presence or absence of SARS-Cov-2 after suspected or confirmed exposure to SARS-Cov-2, or after an elapsed time in which exposure to SARS-Cov-2 is likely. In some cases, the infection rate can be reduced compared with subjects not administered a composition comprising an mRNA molecule provided herein by at least 5%, at least 10%, at least 20%, at least 30%, at least 40%, at least 50%, at least 60%, at least 70%, at least 80%, or at least 90%. In some cases, the infection rate can be reduced compared with subjects not administered a composition comprising an mRNA molecule provided herein by about 10%, about 20%, about 30%, about 40%, about 50%, about 60%, about 70%, about 80%, about 90%, or a range between any two foregoing values.

The present disclosure also provides methods for slowing or preventing reproduction of SARS-Cov-2 in a subject by administering to a subject infected with SARS-Cov-2 a composition comprising one or more polynucleotides (e.g., mRNA) encoding an antibody or antigen-binding fragment that can specifically bind to SARS-Cov-2. Slowing or preventing reproduction of SARS-Cov-2 can be determined for example by comparing the rate of reproduction of the virus in subjects infected SARS-Cov-2 between a cohort that receives the composition and a cohort that does not receive the composition. Replication of SARS-Cov-2 can be determine for example by determining (directly or indirectly) the amount of SARS-Cov-2 in a sample acquired from the subject at different time points. Assays that can be used to determine amount of SARS-Cov-2 in a sample can include a plaque assay, a focus forming assay, an endpoint dilution assay, a protein assay (e.g., a bicinchoninic acid assay or a single radial immunodiffusion assay), transmission electron microscopy, tunable resistive pulse sensing, flow cytometry, qPCR, ELISA, or another acceptable method. An assay can be performed on a whole sample or a fraction of a sample, or SARS-Cov-2 can be isolated from the sample prior to performing an assay. In some cases, the reproduction of SARS-Cov-2 can be slowed compared with subjects not administered a composition comprising an mRNA molecule provided herein by at least 5%, at least 10%, at least 20%, at least 30%, at least 40%, at least 50%, at least 60%, at least 70%, at least 80%, or at least 90%. In some cases, the reproduction of SARS-Cov-2 can be slowed compared with subjects not administered a composition comprising an mRNA molecule provided herein by about 10%, about 20%, about 30%, about 40%, about 50%, about 60%, about 70%, about 80%, about 90%, or a range between any two foregoing values.

The present disclosure also provides methods of activating T cells in a subject comprising administering to a subject a composition comprising one or more polynucleotides (e.g., mRNA) encoding an antibody or antigen-binding fragment that can specifically bind to SARS-Cov-2. In some cases, T cell activation can be elevated compared with subjects not administered the composition. Activation of T cells can be determined for example by comparing the activation of T cells in subjects infected SARS-Cov-2 between a cohort that receives the composition and a cohort that does not receive the composition. In one aspect, the activation of T cells in the subject can be directed to an anti-SARS-Cov-2 response in the subject. Activated T cells in the subject can reduce severity of COVID-19 symptoms, death rate, time to recovery, or viral reproduction in the subject. Activation of T cells can be measured for example by measuring T cell proliferation, measuring cytokine production (e.g., via enzyme-linked immunosorbent assays or enzyme-linked immunospot assays), or detection of cell-surface markers associated with T cell activation (e.g., CD69, CD40L, CD137, CD25, CD71, CD26, CD27, CD28, CD30, CD154, or CD134) for example by flow cytometry. In some cases, the T cell activation can be elevated compared with subjects not administered a composition comprising an mRNA molecule provided herein by at least 5%, at least 10%, at least 20%, at least 30%, at least 40%, at least 50%, at least 60%, at least 70%, at least 80%, or at least 90%. In some cases, the T cell activation can be elevated compared with subjects not administered a composition comprising an mRNA molecule provided herein by about 10%, about 20%, about 30%, about 40%, about 50%, about 60%, about 70%, about 80%, about 90%, or a range between any two foregoing values.

The present disclosure also provides methods for inducing T cell proliferation in a subject comprising administering to a subject a composition comprising one or more polynucleotides (e.g., mRNA) encoding an antibody or antigen-binding fragment that can specifically bind to SARS-Cov-2. In some cases, T cell proliferation can be elevated compared with subjects not administered the composition. In some cases, T cell proliferation can be directed to an anti-SARS-Cov-2 response in the subject. In some cases, T cell proliferation in the subject can reduce or decrease severity of COVID-19 symptoms, death rate, time to recovery, or viral reproduction in the subject. T cell proliferation can be determined for example by cell counting, viability staining, optical density assays, or detection of cell-surface markers associated with T cell activation (e.g., CD69, CD40L, CD137, CD25, CD71, CD26, CD27, CD28, CD30, CD154, or CD134) for example by flow cytometry. In some cases, T cell proliferation can be elevated compared with subjects not administered a composition comprising an mRNA molecule provided herein by at least 5%, at least 10%, at least 20%, at least 30%, at least 40%, at least 50%, at least 60%, at least 70%, at least 80%, or at least 90%. In some cases, T cell proliferation can be elevated compared with subjects not administered a composition comprising an mRNA molecule provided herein by about 10%, about 20%, about 30%, about 40%, about 50%, about 60%, about 70%, about 80%, about 90%, or a range between any two foregoing values.

The present disclosure also provides methods for inducing a memory T cell response in a subject comprising administering to a subject a composition comprising one or more polynucleotides (e.g., mRNA) encoding an antibody or antigen-binding fragment that can specifically bind to SARS-Cov-2. In some cases, a memory T cell response can be elevated compared with subjects not administered the composition. In some cases, a memory T cell response in the subject can reduce or decrease i severity of COVID-19 symptoms, death rate, time to recovery, or viral reproduction in the subject. A memory T cell response can be directed to an anti-SARS-Cov-2 response in the subject. A memory T cell response can be determined for example by measuring T cell markers associated with memory T cells, measuring local cytokine production related to memory immune response, or detecting memory T cell-surface markers for example by flow cytometry. In some cases, the memory T cell response can be elevated compared with subjects not administered a composition comprising an mRNA molecule provided herein by at least 5%, at least 10%, at least 20%, at least 30%, at least 40%, at least 50%, at least 60%, at least 70%, at least 80%, or at least 90%. In some cases, the memory T cell response can be elevated compared with subjects not administered a composition comprising an mRNA molecule provided herein by about 10%, about 20%, about 30%, about 40%, about 50%, about 60%, about 70%, about 80%, about 90%, or a range between any two foregoing values.

A polynucleotide (e.g., mRNA) herein can be administered in any route available, including, but not limited to, enteral, gastroenteral, oral, transdermal, epicutaneous, intradermal, subcutaneous, nasal administration, intravenous, intraperitoneal, intraarterial, intramuscular, intraosseous infusion, transmucosal, insufflation, or sublingual administration. In some cases, mRNA of the present disclosure can be administered parenterally (e.g., includes subcutaneous, intravenous, intraperitoneal, intratumoral, intramuscular, intra-articular, intra-synovial, intrasternal, intrathecal, intrahepatic, intralesional and injection or infusion techniques), intraventricularly, orally, by inhalation spray, topically, rectally, nasally, buccally, or via an implanted reservoir.

Actual dosage levels of antibody can be varied so as to obtain an amount of the active ingredient that is effective to achieve the desired therapeutic response without being toxic to the patient. The selected dosage level will depend upon a variety of factors including the activity of the particular antibody employed, the route of administration, the time of administration, the rate of excretion of the particular antibody being employed, the duration of the treatment, other drugs, compounds and/or materials used in combination with the particular composition employed, the age, sex, weight, condition, general health and prior medical history of the patient being treated, and like factors well known in the medical arts.

The antibodies and antigen-binding fragments herein can be administered to a subject in various dosing amounts and over various time frames.

A physician or veterinarian can readily determine and prescribe the effective amount (ED50) of the antibody or antigen-binding fragment required. For example, the physician or veterinarian could start doses of the antibody or antigen-binding fragment employed in the composition at levels lower than that required in order to achieve the desired therapeutic effect and gradually increase the dosage until the desired effect is achieved. Alternatively, a dose can remain constant.

The antibody or antigen-binding fragment can be administered to a patient by any convenient route such as described above. Regardless of the route of administration selected, the antibodies or antigen-binding fragments, which can be used in a suitable hydrated form, and/or the compositions, are formulated into acceptable dosage forms.

Toxicity and therapeutic efficacy of compounds can be determined by standard procedures in cell cultures or experimental animals, e.g., for determining the LD50 (the dose lethal to 50% of the population) and the $ED_{50}$ (the dose therapeutically effective in 50% of the population). The dose ratio between toxic and therapeutic effects is the therapeutic index and it can be expressed as the ratio LD50/ED50. While compounds that exhibit toxic side effects may be used, care should be taken to design a delivery system that targets such compounds to the site of affected tissue in order to minimize potential damage to healthy cells and, thereby, reduce side effects.

Data obtained from cell culture assays and/or animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound, a therapeutically effective dose can be estimated initially from cell culture assays. A dose can be formulated in animal models to achieve a circulating plasma concentration arrange that includes the IC50 (i.e., the concentration of the test compound which achieves a half-maximal inhibition) as determined in cell culture. Levels in plasma can be measured, for example, by high performance liquid chromatography. Such information can be used to more accurately determine useful doses in humans.

It will be understood that administration of one or more of the antibodies or antigen-binding fragments herein can be supplemented by one or more additional therapies or drugs such as, for example, respiratory therapy; one or more blood thinners or anti-coagulants; statins; hydroxy chloroquine; intubation; one or more antibiotics (e.g., doxycycline, Azithromycin, etc.); one or more decongestants (e.g., Mucinex, Sudafed, etc.); one or more anti-histamines and/or glucocorticoids (e.g., Zyrtec, Claritin, Allegra, fluticasone luroate, etc.); one or more pain relievers (e.g., acetominophen); one or more zinc-containing medications (e.g., Zycam, etc.); Azithromycin, hydroquinolone, or a combination thereof; one or more integrase inhibitors (e.g., Bictegravir, dolutegravir (Tivicay), elvitegravir, raltegravir, or a combination thereof); one or more nucleoside/nucleotide reverse transcriptase inhibitors (NRTIs; e.g., abacavir (Ziagen), emtricitabine (Emtriva), lamivudine (Epivir), tenofovir alafenamide fumarate (Vemlidy), tenofovir disoproxil fumarate (Viread), zidovudine (Retrovir), didanosine (Videx, Videx EC), stavudine (Zerit), or a combination thereof); a combination of NRTIs (e.g., (i) abacavir, lamivudine, and zidovudine (Trizivir), (ii) abacavir and lamivudine (Epzicom), (iii) emtricitabine and tenofovir alafenamide fumarate (Descovy), (iv) emtricitabine and tenofovir disoproxil fumarate (Truvada), (v) lamivudine and tenofovir disoproxil fumarate (Cimduo, Temixys), (vi) lamivudine and zidovudine (Combivir), etc.); a combination of Descovy and Truvada; one or more non-nucleoside reverse transcriptase inhibitors (NNRTIs; e.g., doravirine (Pifeltro), efavirenz (Sustiva), etravirine (Intelence), nevirapine (Viramune, Viramune XR), rilpivirine (Edurant), delavirdine (Rescriptor), or a combination thereof); one or more Cytochrome P4503A (CYP3A) inhibitors (e.g., cobicistat (Tybost), ritonavir (Norvir), etc.); one or more protease inhibitors (PIs; e.g., atazanavir (Reyataz), darunavir (Prezista), fosamprenavir (Lexiva), lopinavir, ritonavir (Norvir), tipranavir (Aptivus), etc.); one or PIs in combination with cobicistat, ritonavir, Lopinavir, Tipranavir, Atazanavir, fosamprenavir, indinavir (Crixivan), nelfinavir (Viracept), saquinavir (Invirase), or a combination thereof; Atazanavir; fosamprenavir; a combination of Atazanavir, darunavir and cobicistat; one or more fusion inhibitors (e.g., enfuvirtide (Fuzeon); one or more post-attachment inhibitors (e.g., ibalizumab-uiyk (Trogarzo)); one or more Chemokine coreceptor antagonists (CCR5 antagonists; e.g., maraviroc (Selzentry)); and one or more viral entry inhibitors (e.g., enfuvirtide (Fuzeon), ibalizumab-uiyk (Trogarzo), maraviroc (Selzentry), etc.); or a combination thereof.

Non-limiting examples of combinations include one or more of the antibodies or antigen-binding fragments herein to be administered with one or more of the following: (1) Azithromycin, hydroquinolone, or a combination thereof, (2) darunavir and cobicistat (Prezcobix), (3) lopinavir and ritonavir (Kaletra), (4) abacavir, lamivudine, and zidovudine (Trizivir), (5) abacavir and lamivudine (Epzicom), (6) emtricitabine and tenofovir alafenamide fumarate (Descovy), (7) emtricitabine and tenofovir disoproxil fumarate (Truvada), (8) lamivudine and tenofovir disoproxil fumarate (Cimduo, Temixys), (9) lamivudine and zidovudine (Combivir), (10), atazanavir and cobicistat (Evotaz), (11) doravirine, lamivudine, and tenofovir disoproxil fumarate (Delstrigo), (12) efavirenz, lamivudine, and tenofovir disoproxil fumarate (Symfi), (13) efavirenz, lamivudine, and tenofovir disoproxil fumarate (Symfi Lo), (14) efavirenz, emtricitabine, and tenofovir disoproxil fumarate (Atripla), (15) emtricitabine, rilpivirine, and tenofovir alafenamide fumarate (Odefsey), (16) emtricitabine, rilpivirine, and tenofovir disoproxil fumarate (Complera), (17) elvitegravir, cobicistat, emtricitabine, and tenofovir disoproxil fumarate (Stribild), (18) elvitegravir, cobicistat, emtricitabine, and tenofovir alafenamide fumarate (Genvoya), (19) abacavir, dolutegravir, and lamivudine (Triumeq), (20) bictegravir, emtricitabine, and tenofovir alafenamide fumarate (Biktarvy), (21) dolutegravir and lamivudine (Dovato), (22) dolutegravir and rilpivirine (Juluca), (23) darunavir, cobicistat, emtricitabine, and tenofovir alafenamide fumarate (Svmtuza).

Non-limiting examples of combinations include one or more of the antibodies or antigen-binding fragments herein to be administered with one or more blood thinners. Blood thinners to be co-administered include, but are not limited to, anti-platelet, and anti-coagulation medications. Anti-platelet medications are those such as, for example, aspirin, clopidogrel (PLAVIX®); prasugrel (EFFIENT®); ticlopidine (TICLID®); ticagrelor (BRILINTA®); and combinations thereof. Anticoagulants include, but are not limited to, Warfarin (COUMADIN®, JANTOVEN®); Heparin (e.g., FRAGMIN, INNOHEP®, and LOVENOX®); Eabigatran (PRADAXA®); Epixaban (ELIQUIS®); Non-vitamin K antagonist oral anticoagulants (NOACs) such as, for example, Rivaroxaban (XARELTO®); Factor Xa inhibitors such as, for example, Edoxaban (SAVAYSA®), Fondaparinux (ARIXTRA®); and combinations thereof.

Diagnostics

Provided herein are methods of diagnosing a subject suspected of being infected with SARS-Cov-2 by contacting a sample obtained from the subject with one or more 2ghw-derived antibodies or antigen-binding fragments herein.

A "sample" from a subject to be tested utilizing one or more of the assays herein includes, but is not limited to, a nasal swab, a tissue sample, saliva, blood, etc. In some instances, the sample is treated prior to use in a diagnostic assay. For example, a nasal swab may be flushed with phosphate buffered saline (PBS); a fluid sample may be centrifuged to concentrate the sample components; blood may be treated with heparin to prevent coagulation, etc.

Samples may be tested in any suitable assay including, but not limited to, an enzyme linked immunosorbent assay (ELISA), an immunospot assay, a lateral flow assay, immunohistochemistry (IHC), western blot, flow cytometry, etc. The sample is contacted with a 2ghw-derived antibody or antigen-binding fragment herein, and when the presence of the antibody or antigen-binding fragment bound to a SARS-Cov-2 is detected, the subject is diagnosed as being infected with SARS-Cov-2 and/or having a COVID-19 infection.

In one instance, a sample obtained from a subject is contacted with a 2ghw-derived antibody or antigen-binding fragment herein that selectively binds to SARS-Cov-2 and the presence or absence of the antibody or antigen-binding fragment is determined. The subject is diagnosed as being infected with SARS-Cov-2 when the presence of the 2ghw-derived antibody or antigen-binding fragment is detected.

Exemplary Definitions

The term "about" as used herein, generally refers to a range that is 2%, 5%, 10%, 15% greater than or less than (±) a stated numerical value within the context of the particular usage. For example, "about 10" would include a range from 8.5 to 11.5. As used herein, the terms "about" and "approximately," when used to modify a numeric value or numeric range, indicate that deviations of up to about 0.2%, about 0.5%, about 1%, about 2%, about 5%, about 7.5%, or about 10% (or any integer between about 1% and 10%) above or below the value or range remain within the intended meaning of the recited value or range.

As used in this specification and the appended claims, the singular forms "a," "an," and "the" include plural references unless the context clearly dictates otherwise. Thus, for example, references to "a method" include one or more methods, and/or steps of the type described herein and/or which will become apparent to those persons skilled in the art upon reading this disclosure.

Polypeptides (e.g., proteins) and polynucleotides (e.g., nucleic acids) herein can be isolated and/or purified from their natural environment in substantially pure or homogeneous form. Methods of purifying proteins and nucleic acids are contemplated for use herein. "Isolated" (used interchangeably with "substantially pure") when applied to polypeptides means a polypeptide or a portion thereof which, by virtue of its origin or manipulation: (i) is present in a host cell as the expression product of a portion of an expression vector; (ii) is linked to a protein or other chemical moiety other than that to which it is linked in nature; or (iii) does not occur in nature, for example, a protein that is chemically manipulated by appending, or adding at least one hydrophobic moiety to the protein so that the protein is in a form not found in nature. By "isolated" it is further meant a protein that is: (i) synthesized chemically or (ii) expressed in a host cell and purified away from associated and contaminating proteins. The term generally means a polypeptide that has been separated from other proteins and nucleic acids with which it naturally occurs. The polypeptide may also be separated from substances such as antibodies or gel matrices (polyacrylamide) which are used to purify it. As used herein, substantially pure, isolated," or purified refers to material which is at least 50% pure (e.g., free from contaminants), at least 60% pure, at least 70% pure, at least 80% pure, at least 85% pure, at least 90% pure, at least 91% pure, at least 92% pure, at least 93% pure, at least 94% pure, at least 95% pure, at least 96% pure, at least 97% pure, at least 98% pure, or at least 99% pure.

Polypeptides can be isolated and purified from culture supernatant or ascites by saturated ammonium sulfate precipitation method, an euglobulin precipitation method, a caproic acid method, a caprylic acid method, ion exchange chromatography (DEAE or DE52), or affinity chromatography using anti-Ig column or a protein A, protein G, or protein L column such as described in more detail below. In one aspect, reference to a binding agent, an antibody or an antigen-binding fragment also refers to an "isolated binding agent," an "isolated antibody," or an "isolated antigen-binding fragment." In another aspect, reference to a binding agent, an antibody, or an antigen-binding fragment also refers to a "purified binding agent," a "purified antibody," or a "purified antigen-binding fragment."

Antibodies can be "isolated" and "purified" from the culture supernatant or ascites mentioned above by saturated ammonium sulfate precipitation, euglobulin precipitation method, caproic acid method, caprylic acid method, ion exchange chromatography (DEAE or DE52), or affinity chromatography using anti-Ig column or a protein A, G or L column using art-recognized conventional methods.

As used herein, the term "antibody" refers to an immunoglobulin (Ig), polypeptide, or a protein having a binding domain which is, or is homologous to, an antigen-binding domain. The term further includes "antigen-binding fragments" and other interchangeable terms for similar binding fragments as described below. Native antibodies and native immunoglobulins (Igs) are generally heterotetrameric glycoproteins of about 150,000 Daltons, composed of two identical light chains and two identical heavy chains. Each light chain is typically linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ("VH") followed by a number of constant domains ("CH"). Each light chain has a variable domain at one end ("VL") and a constant domain ("CL") at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains. In some instances, an antibody or an antigen-binding fragment comprises an isolated antibody or antigen-binding fragment, a purified antibody or antigen-binding fragment, a recombinant antibody or antigen-binding fragment, a modified antibody or antigen-binding fragment, or a synthetic antibody or antigen-binding fragment.

Antibodies and antigen-binding fragments herein can be partly or wholly synthetically produced. An antibody or antigen-binding fragment can be a polypeptide or protein having a binding domain which can be, or can be homologous to, an antigen-binding domain. In one instance, an antibody or an antigen-binding fragment can be produced in an appropriate in vivo animal model and then isolated and/or purified. It would be understood that the antibodies or antigen-binding fragments herein can be modified as described below or as known in the art.

Antibodies useful in the present invention encompass, but are not limited to, monoclonal antibodies, polyclonal antibodies, antibody fragments (e.g., Fab, Fab', F(ab')2, Fv, Fc, scFv, scFv-Fc, Fab-Fc, scFv-zipper, scFab, crossFab, camelids (VHH), etc.), chimeric antibodies, bispecific antibodies, multispecific antibodies, heteroconjugate antibodies, single chain (ScFv), mutants thereof, fusion proteins comprising an antibody portion (e.g., a domain antibody), humanized antibodies, human antibodies, and any other modified configuration of the immunoglobulin molecule that comprises an antigen recognition site of the required specificity, including glycosylation variants of antibodies, amino acid sequence variants of antibodies, and covalently modified antibodies.

Depending on the amino acid sequence of the constant domain of its heavy chains, immunoglobulins (Igs) can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. An Ig or portion thereof can, in some cases, be a human Ig. In some instances, a CH3 domain can be from an immunoglobulin. In some cases, a chain or a part of an antibody or antigen-binding fragment, a modified antibody or antigen-binding, or a binding agent can be from an Ig. In such cases, an Ig can be IgG, an IgA, an IgD, an IgE, or an IgM. In cases where the Ig is an IgG, it can be a subtype of IgG, wherein subtypes of IgG can include IgG1, an IgG2a, an IgG2b, an IgG3, and an IgG4. In some cases, a CH3 domain can be from an immunoglobulin selected from the group consisting of an IgG, an IgA, an IgD, an IgE, and an IgM.

The "light chains" of antibodies (immunoglobulins) from any vertebrate species can be assigned to one of two clearly distinct types, called kappa or ("κ" or "K") and lambda or ("λ"), based on the amino acid sequences of their constant domains.

As used herein, a "monoclonal antibody" refers to an antibody obtained from a population of substantially homogeneous antibodies, e.g., the individual antibodies comprising the population are identical except for possible naturally-occurring mutations that may be present in minor amounts. In contrast to polyclonal antibody preparations, which typically include different antibodies directed against different determinants (epitopes), each monoclonal antibody is directed against a single determinant on the antigen (epitope). The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, 1975, *Nature,* 256:495, or may be made by recombinant DNA methods such as described in U.S. Pat. No. 4,816,567. The monoclonal antibodies may also be isolated from phage libraries generated using the techniques described in McCafferty et al., 1990, *Nature,* 348:552-554, for example. Other methods are known in the art and are contemplated for use herein.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. Amino acid residues of CDRs and framework regions are as described herein for the provided sequences.

With respect to antibodies, the term "variable domain" refers to the variable domains of antibodies that are used in the binding and specificity of each particular antibody for its particular antigen. However, the variability is not evenly distributed throughout the variable domains of antibodies. Rather, it is concentrated in three segments called hypervariable regions (also known as CDRs) in both the light chain and the heavy chain variable domains. More highly conserved portions of variable domains are called the "framework regions," "FWs," or "FRs." The variable domains of unmodified heavy and light chains each contain four FRs (FR1, FR2, FR3, and FR4), largely adopting a β-sheet configuration interspersed with three CDRs which form loops connecting and, in some cases, part of the β-sheet structure. The CDRs in each chain are held together in close proximity by the FRs and, with the CDRs from the other chain, contribute to the formation of the antigen-binding site of antibodies.

A "constant region" of an antibody refers to the constant region of the antibody light chain or the constant region of the antibody heavy chain, either alone or in combination.

"Epitope" refers to that portion of an antigen or other macromolecule capable of forming a binding interaction with the variable region binding pocket of an antibody. Such binding interactions can be manifested as an intermolecular contact with one or more amino acid residues of one or more CDRs. Antigen-binding can involve, for example, a CDR3 or a CDR3 pair or, in some cases, interactions of up to all six CDRs of the VH and VL chains. An epitope can be a linear peptide sequence ("continuous") or can be composed of noncontiguous amino acid sequences ("conformational" or "discontinuous"). An antibody can recognize one or more amino acid sequences; therefore, an epitope can define more than one distinct amino acid sequence. Epitopes recognized by antibodies can be determined by peptide mapping and sequence analysis techniques well known to one of skill in the art. Binding interactions are manifested as intermolecular contacts between an epitope on an antigen and one or more amino acid residues of a CDR. An epitope provided herein can refer to an amino acid sequence on a receptor binding domain or a spike domain.

An antibody selectively binds to a target if it binds with greater affinity, avidity, more readily, and/or with greater duration than it binds to other substances. For example, an antibody or antigen-binding fragment that selectively binds to a SARS-Cov-2 epitope is an antibody or antigen-binding fragment that binds this epitope with greater affinity, avidity, more readily, and/or with greater duration than it binds to SARS-Cov-1 or MERS. "

The term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The Fc region of an immunoglobulin generally comprises two constant domains, CH2 and CH3.

The terms "hypervariable region" and "CDR" when used herein, refer to the amino acid residues of an antibody which are responsible for antigen-binding. The CDRs comprise amino acid residues from three sequence regions which bind in a complementary manner to an antigen and are known as CDR1, CDR2, and CDR3 for each of the VH and VL chains. It is understood that the CDRs of different antibodies may contain insertions, thus the amino acid numbering may differ. CDR sequences of the antibodies and antigen-binding fragments have been provided herein.

As used herein, "framework region" or "FR" or "FW" refers to framework amino acid residues that form a part of the antigen-binding pocket or groove. In some embodiments, the framework residues form a loop that is a part of the antigen-binding pocket or groove and the amino acids residues in the loop may or may not contact the antigen. Framework regions generally comprise the regions between the CDRs. Framework regions of the antibodies and antigen-binding fragments have been provided herein below.

The loop amino acids of a FR can be assessed and determined by inspection of the three-dimensional structure of an antibody heavy chain and/or antibody light chain. The three-dimensional structure can be analyzed for solvent accessible amino acid positions as such positions are likely to form a loop and/or provide antigen contact in an antibody variable domain. Some of the solvent accessible positions can tolerate amino acid sequence diversity and others (e.g., structural positions) are, generally, less diversified. The three-dimensional structure of the antibody variable domain can be derived from a crystal structure or protein modeling.

In the present disclosure, the following abbreviations (in the parentheses) are used in accordance with the customs, as necessary: heavy chain (H chain), light chain (L chain), heavy chain variable region (VH), light chain variable region (VL), complementarity determining region (CDR), first complementarity determining region (CDR1), second complementarity determining region (CDR2), third complementarity determining region (CDR3), heavy chain first complementarity determining region (VH CDR1), heavy chain second complementarity determining region (VH CDR2), heavy chain third complementarity determining region (VH CDR3), light chain first complementarity determining region (VL CDR1), light chain second complementarity determining region (VL CDR2), and light chain third complementarity determining region (VL CDR3).

In some instances, an anti-SARS-Cov-2 antibody is a monoclonal antibody. As used herein, a "monoclonal antibody" refers to an antibody obtained from a population of substantially homogeneous antibodies, i.e., the individual antibodies comprising the population are identical except for possible naturally-occurring mutations that may be present in minor amounts. In contrast to polyclonal antibody preparations, which typically include different antibodies directed against different determinants (epitopes), each monoclonal antibody is directed against a single determinant on the antigen (epitope). The modifier "monoclonal" indicates the character of the antibody as being obtained from a substantially homogeneous population of antibodies and is not to be construed as requiring production of the antibody by any particular method, including the Tumbler methods described below.

In some instances, an anti-SARS-Cov-2 antibody or antigen-binding fragment is a humanized antibody or a humanized antigen-binding fragment. As used herein, "humanized" antibodies refer to forms of non-human (e.g., murine) antibodies that are specific chimeric immunoglobulins, immunoglobulin chains, or fragments thereof that contain minimal sequence derived from non-human immunoglobulin. For the most part, humanized antibodies are human immunoglobulins (recipient antibody) in which residues from a complementarity determining region (CDR) of the recipient are replaced by residues from a CDR of a non-human species (donor antibody) such as mouse, rat, or rabbit having the desired specificity, affinity, and biological activity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, a humanized antibody comprises substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in, for example, WO 99/58572. Other forms of humanized antibodies have one or more CDRs (one, two, three, four, five, or six) which are altered with respect to the original antibody, which are also termed one or more CDRs "derived from" one or more CDRs from the original antibody.

If needed, an antibody or an antigen-binding fragment herein can be assessed for immunogenicity and, as needed, be deimmunized (i.e., the antibody is made less immunoreactive by altering one or more T cell epitopes). As used herein, a "deimmunized antibody" means that one or more T cell epitopes in an antibody sequence have been modified such that a T cell response after administration of the antibody to a subject is reduced compared to an antibody that has not been deimmunized. Analysis of immunogenicity and T-cell epitopes present in the antibodies and antigen-binding fragments described herein can be carried out via the use of software and specific databases. Exemplary software and databases include iTope™ developed by Antitope of Cambridge, England. iTope™, is an in silico technology for analysis of peptide binding to human MHC class II alleles. The iTope™ software predicts peptide binding to human MHC class II alleles and thereby provides an initial screen for the location of such "potential T cell epitopes." iTope™ software predicts favorable interactions between amino acid side chains of a peptide and specific binding pockets within the binding grooves of 34 human MHC class II alleles. The location of key binding residues is achieved by the in silico generation of 9mer peptides that overlap by one amino acid spanning the test antibody variable region sequence. Each 9mer peptide can be tested against each of the 34 MHC class II allotypes and scored based on their potential "fit" and interactions with the MHC class II binding groove. Peptides that produce a high mean binding score (>0.55 in the iTope™ scoring function) against >50% of the MHC class II alleles are considered as potential T cell epitopes. In such regions, the core 9 amino acid sequence for peptide binding within the MHC class II groove is analyzed to determine the MHC class II pocket residues (P1, P4, P6, P7, and P9) and the possible T cell receptor (TCR) contact residues (P-1, P2, P3, P5, P8). After identification of any T-cell epitopes, amino acid residue changes, substitutions, additions, and/or deletions can be introduced to remove the identified T-cell epitope. Such changes can be made so as to preserve antibody structure and function while still removing the identified epitope. Exemplary changes can include, but are not limited to, conservative amino acid changes.

An anti-SARS-Cov-2 antibody or antigen-binding fragment can be a human antibody or human antigen-binding fragment. As used herein, a "human antibody" means an antibody having an amino acid sequence corresponding to that of an antibody produced by a human and/or that has been made using any suitable technique for making human antibodies. This definition of a human antibody includes antibodies comprising at least one human heavy chain polypeptide or at least one human light chain polypeptide. One such example is an antibody comprising murine light chain and human heavy chain polypeptides. In one embodiment, the human antibody is selected from a phage library, where that phage library expresses human antibodies (Vaughan et al., 1996, *Nature Biotechnology*, 14:309-314; Sheets et al., 1998, *PNAS USA*, 95:6157-6162; Hoogenboom and Winter, 1991, *J. Mol. Biol.*, 227:381; Marks et al., 1991, *J. Mol. Biol.*, 222:581). Human antibodies can also be made by introducing human immunoglobulin loci into transgenic animals, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or may have been immunized in vitro). See, e.g., Cole et al., Monoclonal Antibodies and Cancer Therapy, Alan R. Liss, p. 77 (1985); Boerner et al., 1991, *J. Immunol.*, 147 (1):86-95; and U.S. Pat. No. 5,750,373.

Any of the anti-SARS-Cov-2 antibodies or antigen-binding fragments described herein can be bispecific. Bispecific antibodies are antibodies that have binding specificities for at least two different antigens or different affinities for the same antigen. Bispecific antibodies can be prepared using the antibodies or antigen-binding fragments disclosed herein. Methods for making bispecific antibodies are described (see, e.g., Suresh et al., 1986, *Methods in Enzymology* 121:210). Traditionally, the recombinant production of bispecific antibodies was based on the co-expression of two immunoglobulin heavy chain-light chain pairs, with the two heavy chains having different specificities (Millstein and Cuello, 1983, *Nature*, 305, 537-539). Bispecific antibodies can be composed of a hybrid immunoglobulin heavy chain with a first binding specificity in one arm, and a hybrid immunoglobulin heavy chain-light chain pair (providing a second binding specificity) in the other arm. This asymmetric structure, with an immunoglobulin light chain in only one half of the bispecific molecule, facilitates the separation of the desired bispecific compound from unwanted immunoglobulin chain combinations. Bispecific antibody fragments may be connected via a linker. This approach is described in PCT Publication No. WO 94/04690.

According to one approach to making bispecific antibodies, antibody variable domains with the desired binding specificities (antibody-antigen combining sites) are fused to immunoglobulin constant domain sequences. The fusion can be with an immunoglobulin heavy chain constant domain, comprising at least part of the hinge, CH2 and CH3 regions. The first heavy chain constant region (CH1), containing the site necessary for light chain binding, can be present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

Heteroconjugate antibodies, comprising two covalently joined antibodies, are also within the scope of the disclosure. Such antibodies have been used to target immune system cells to unwanted cells (U.S. Pat. No. 4,676,980). Heteroconjugate antibodies may be made using any suitable cross-linking methods. Suitable cross-linking agents and techniques are described, for example, in U.S. Pat. No. 4,676,980.

In some instances, an anti-SARS-Cov-2 antibody described herein is a chimeric antibody. "Chimeric" forms of non-human (e.g., murine) antibodies include chimeric antibodies which contain minimal sequence derived from a non-human Ig. For the most part, chimeric antibodies are murine antibodies in which at least a portion of an immunoglobulin constant region (Fc), typically that of a human immunoglobulin, is inserted in place of the murine Fc. Chimeric or hybrid antibodies also may be prepared in vitro using suitable methods of synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate.

Provided herein are antibodies and antigen-binding fragments, modified antibodies and antigen-binding fragments, and binding agents that specifically bind to one or more epitopes on one or more target antigens. In one instance, a binding agent selectively binds to an epitope on a single antigen. In another instance, a binding agent is bivalent and either selectively binds to two distinct epitopes on a single antigen or binds to two distinct epitopes on two distinct antigens. In another instance, a binding agent is multivalent (i.e., trivalent, quatravalent, etc.) and the binding agent binds to three or more distinct epitopes on a single antigen or binds to three or more distinct epitopes on two or more (multiple) antigens.

Functional fragments of any of the antibodies herein are also contemplated. The terms "antigen-binding portion of an antibody," "antigen-binding fragment," "antigen-binding domain," "antibody fragment," or a "functional fragment of an antibody" are used interchangeably herein to refer to one or more fragments of an antibody that retain the ability to specifically bind to an antigen. Representative antigen-binding fragments include, but are not limited to, a Fab, a Fab', a F(ab')$_2$, a Fv, a scFv, a dsFv, a variable heavy domain, a variable light domain, a variable NAR domain, bi-specific scFv, a bi-specific Fab$_2$, a tri-specific Fab$_3$, an AVIMER®, a minibody, a diabody, a maxibody, a camelid, a VHH, an intrabody, fusion proteins comprising an antibody portion (e.g., a domain antibody), a single chain binding polypeptide, a scFv-Fc, or a Fab-Fc.

"F(ab')$_2$" and "Fab'" moieties can be produced by treating an Ig with a protease such as pepsin and papain, and include antibody fragments generated by digesting immunoglobulin near the disulfide bonds existing between the hinge regions in each of the two heavy chains. For example, papain cleaves IgG upstream of the disulfide bonds existing between the hinge regions in each of the two heavy chains to generate two homologous antibody fragments in which an light chain composed of $V_L$ and $C_L$ (light chain constant region), and a heavy chain fragment composed of $V_H$ and $C_{H\gamma 1}$ (γ1) region in the constant region of the heavy chain) are connected at their C terminal regions through a disulfide bond. Each of these two homologous antibody fragments is called Fab'. Pepsin also cleaves IgG downstream of the disulfide bonds existing between the hinge regions in each of the two heavy chains to generate an antibody fragment slightly larger than the fragment in which the two above-mentioned Fab' are connected at the hinge region. This antibody fragment is called F(ab')$_2$.

The Fab fragment also contains the constant domain of the light chain and the first constant domain ($C_H 1$) of the heavy chain. Fab' fragments differ from Fab fragments by the addition of a few residues at the carboxyl terminus of the heavy chain $C_H 1$ domain including one or more cysteine(s) from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

A "Fv" as used herein refers to an antibody fragment which contains a complete antigen-recognition and antigen-binding site. This region consists of a dimer of one heavy chain and one light chain variable domain in tight, non-covalent or covalent association (disulfide linked Fvs have been described, see, e.g., Reiter et al. (1996) *Nature Biotechnology* 14:1239-1245). It is in this configuration that the three CDRs of each variable domain interact to define an antigen-binding site on the surface of the $V_H$-$V_L$ dimer. Collectively, a combination of one or more of the CDRs from each of the VH and VL chains confer antigen-binding specificity to the antibody. For example, it would be understood that, for example, the CDRH3 and CDRL3 could be sufficient to confer antigen-binding specificity to an antibody when transferred to $V_H$ and $V_L$ chains of a recipient antibody or antigen-binding fragment and this combination of CDRs can be tested for binding, specificity, affinity, etc. using any of the techniques described herein. Even a single variable domain (or half of an Fv comprising only three CDRs specific for an antigen) has the ability to recognize and bind antigen, although likely at a lower specificity or affinity than when combined with a second variable domain. Furthermore, although the two domains of a Fv fragment ($V_L$ and $V_H$) are coded for by separate genes, they can be joined using recombinant methods by a synthetic linker that enables them to be made as a single protein chain in which the VL and VH regions pair to form monovalent molecules (known as single chain Fv (scFv); Bird et al. (1988) Science 242:423-426; Huston et al. (1988) *Proc. Natl. Acad. Sci. USA* 85:5879-5883; and Osbourn et al. (1998) *Nat. Biotechnol.* 16:778). Such scFvs are also intended to be encompassed within the term "antigen-binding portion" of an antibody. Any VH and VL sequences of specific scFv can be linked to an Fc region cDNA or genomic sequences in order to generate expression vectors encoding complete Ig (e.g., IgG) molecules or other isotypes. VH and VL can also be used in the generation of Fab, Fv, or other fragments of Igs using either protein chemistry or recombinant DNA technology.

"Single-chain Fv" or "sFv" antibody fragments comprise the VH and VL domains of an antibody, wherein these domains are present in a single polypeptide chain. In some embodiments, the Fv polypeptide further comprises a polypeptide linker between the VH and VL domains which enables the sFv to form the desired structure for antigen binding. For a review of sFvs, see, e.g., Pluckthun in The Pharmacology of Monoclonal Antibodies, Vol. 113, Rosenburg and Moore eds. Springer-Verlag, New York, pp. 269-315 (1994).

The term "AVIMER®" refers to a class of therapeutic proteins of human origin, which are unrelated to antibodies and antibody fragments, and are composed of several modular and reusable binding domains, referred to as A-domains (also referred to as class A module, complement type repeat, or LDL-receptor class A domain). They were developed from human extracellular receptor domains by in vitro exon shuffling and phage display (Silverman et al., 2005, *Nat. Biotechnol.* 23:1493-1494; Silverman et al., 2006, *Nat.*

Biotechnol. 24:220). The resulting proteins can contain multiple independent binding domains that can exhibit improved affinity and/or specificity compared with single-epitope binding proteins. Each of the known 217 human A-domains comprises ~35 amino acids (~4 kDa); and these domains are separated by linkers that average five amino acids in length. Native A-domains fold quickly and efficiently to a uniform, stable structure mediated primarily by calcium binding and disulfide formation. A conserved scaffold motif of only 12 amino acids is required for this common structure. The end result is a single protein chain containing multiple domains, each of which represents a separate function. Each domain of the proteins binds independently, and the energetic contributions of each domain are additive.

Antigen-binding polypeptides also include heavy chain dimers such as, for example, antibodies from camelids and sharks. Camelid and shark antibodies comprise a homodimeric pair of two chains of V-like and C-like domains (neither has a light chain). Since the VH region of a heavy chain dimer IgG in a camelid does not have to make hydrophobic interactions with a light chain, the region in the heavy chain that normally contacts a light chain is changed to hydrophilic amino acid residues in a camelid. VH domains of heavy-chain dimer IgGs are called $V_{HH}$ domains. Shark Ig-NARs comprise a homodimer of one variable domain (termed a V-NAR domain) and five C-like constant domains (C-NAR domains). In camelids, the diversity of antibody repertoire is determined by the CDRs 1, 2, and 3 in the VH or VHH regions. The CDR3 in the camel VHH region is characterized by its relatively long length, averaging 16 amino acids (Muyldermans et al., 1994, Protein Engineering 7(9): 1129). This is in contrast to CDR3 regions of antibodies of many other species. For example, the CDR3 of mouse VH has an average of 9 amino acids. Libraries of camelid-derived antibody variable regions, which maintain the in vivo diversity of the variable regions of a camelid, can be made by, for example, the methods disclosed in U.S. Patent Application Ser. No. 20050037421.

As used herein, a "maxibody" refers to a bivalent scFv covalently attached to the Fc region of an immunoglobulin, see, e.g., Fredericks et al., Protein Engineering, Design & Selection, 17:95-106 (2004) and Powers et al., Journal of Immunological Methods, 251:123-135 (2001).

As used herein, a "dsFv" can be a Fv fragment obtained by introducing a Cys residue into a suitable site in each of a heavy chain variable region and a light chain variable region, and then stabilizing the heavy chain variable region and the light chain variable region by a disulfide bond. The site in each chain, into which the Cys residue is to be introduced, can be determined based on a conformation predicted by molecular modeling. In the present disclosure, for example, a conformation is predicted from the amino acid sequences of the heavy chain variable region and light chain variable region of the above-described antibody, and DNA encoding each of the heavy chain variable region and the light chain variable region, into which a mutation has been introduced based on such prediction, is then constructed. The DNA construct is incorporated then into a suitable vector and prepared from a transformant obtained by transformation with the aforementioned vector.

Single chain variable region fragments ("scFv") of antibodies are described herein. Single chain variable region fragments may be made by linking light and/or heavy chain variable regions by using a short linking peptide. Bird et al. (1988) Science 242:423-426. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect, or mammalian cells, or prokaryotic, such as E. coli. Polynucleotides encoding the scFv of interest can be made by routine manipulations such as ligation of polynucleotides. The resultant scFv can be isolated using any suitable protein purification techniques.

Diabodies can be single chain antibodies. Diabodies can be bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen-binding sites (see, e.g., Holliger, P., et al., Proc. Natl. Acad. Sci. USA, 90:6444-6448 (1993); and Poljak, R. J., et al., Structure, 2:1121-1123 (1994)).

As used herein, a "minibody" refers to a scFv fused to CH3 via a peptide linker (hingeless) or via an IgG hinge has been described in Olafsen, et al., Protein Eng. Des. Sel., April 2004; 17(4):315-23.

As used herein, an "intrabody" refers to a single chain antibody which demonstrates intracellular expression and can manipulate intracellular protein function (Biocca, et al., EMBO J. 9:101-108, 1990; Colby et al., Proc Natl Acad. Sci. USA. 101:17616-21, 2004). Intrabodies, which comprise cell signal sequences which retain the antibody construct in intracellular regions, may be produced as described in Mhashilkar et al., (EMBO J., 14:1542-51, 1995) and Wheeler et al. (FASEB J. 17:1733-5. 2003). Transbodies are cell-permeable antibodies in which a protein transduction domains (PTD) is fused with single chain variable fragment (scFv) antibodies Heng et al. (Med Hypotheses. 64:1105-8, 2005).

A "scFv-Fc" fragment as described herein refers to an scFv attached to an Fc domain. For example, an Fc domain may be attached to the C-terminal of the scFv. The Fc domain may follow the VH or VL, depending on the orientation of the variable domains in the scFv (i.e., VH-VL or VL). Any suitable Fc domain known in the art or described herein may be used. In some cases, the Fc domain comprises an IgG1 Fc domain or an IgG4 Fc domain. A scFv-Fc format allows for rapid characterization of candidate scFvs isolated from phage display libraries before conversion into a full-length IgG. This format offers several advantages over the phage display-derived scFv, including bivalent binding, longer half-life, and Fc-mediated effector functions. Here, a detailed method is presented, which describes the cloning, expression, and purification of an scFv-Fc fragment, starting from scFv fragments obtained from a phage display library. This method facilitates the rapid screening of candidate antibodies, prior to a more time-consuming conversion into a full IgG format. In one instance, a single-chain Fv (scFv) includes the heavy and light chains in the Fv of an anti-SARS-Cov-2 antibody herein joined with a flexible peptide linker (e.g., of about 10, 12, 15 or more amino acid residues) in a single peptide chain. The single chain antibody may be monovalent, if only a single VH and VL are used, bivalent, if two VH and VL are used, or polyvalent, if more than two VH and VL are used. In some instances, the entire Fc region is attached to the scFv. In other instances, only the CH3 region of a Fc is attached to the scFv (a "scFv-CH).

A "scFab" as described herein refers to an antigen-binding domain that specifically binds to SARS-Cov-2 is fused via a peptide linker to the C-terminus to one of the heavy chains.

A "scFv zipper" as described herein refers to constructs of leucine zipper-based dimerization cassettes for the conversion of recombinant monomeric scFv antibody fragments to bivalent and bispecific dimers. A truncated murine IgG3 hinge region and a Fos or Jun leucine zipper are cloned into four scFv fragments. Cysteine residues flanking the zipper region are introduced to covalently link dimerized scFv fragments. The secreted fusion proteins form stable Fos•Fos or Jun•Jun homodimers.

A "cross-Fab fragment" or "xFab fragment" or "crossover Fab fragment" as described herein refers to a Fab fragment, wherein either the variable regions or the constant regions of the heavy and light chain are exchanged. Two different chain compositions of a crossover Fab molecule are possible and comprised within the scope of bispecific antibodies and antigen-binding fragments described herein. On the one hand, the variable regions of the Fab heavy and light chain are exchanged, i.e. the crossover Fab molecule comprises a peptide chain composed of the light chain variable region (VL) and the heavy chain constant region (CH1), and a peptide chain composed of the heavy chain variable region (VH) and the light chain constant region (CL). This crossover Fab molecule is also referred to as CrossFab VLVH. On the other hand, when the constant regions of the Fab heavy and light chain are exchanged, the crossover Fab molecule comprises a peptide chain composed of the heavy chain variable region (VH) and the light chain constant region (CL), and a peptide chain composed of the light chain variable region (VL) and the heavy chain constant region (CH1). This crossover Fab molecule is also referred to as CrossFab CLCH1.

A "Fab-Fc" fragment as described herein refers to a Fab fragment that is attached to a CH1, CH2, and/or a CH3 region of a Fc, where the molecule does not contain all of a CH1, CH2, and CH3.

The terms "single domain antibody" and "sdAb" refer to a single-chain antibody polypeptide consisting of a single monomeric variable antibody domain. The term "VHH" as used herein refers to molecules engineered from heavy-chain antibodies found in camelids. The terms "shark new antigen receptor", "VNAR" and "IgNAR" as used herein refer to molecules obtained from the heavy-chain antibodies of cartilaginous fish, such as sharks. Single-domain antibodies can also be obtained by splitting dimeric variable domains from common immunoglobulin G (IgG) into monomers. Single-domain antibodies are typically about 110 amino acids long and have a typical molecular weight in the region of from about 12 to about 15 kDa. As such, single-domain antibodies are much smaller than common antibodies (150-160 kDa), and even smaller than Fab fragments (which consist of one light chain and half a heavy chain and have a molecular weight of about 50 kDa) and single-chain variable fragments (which consist of two variable domains, one from a light and one from a heavy chain, and have a molecular weight of about 25 kDa).

Suitable linkers may be used to link various parts of recombinant or synthetic antibodies or antigen-binding fragments or to multimerize binding agents. A non-limiting example of a linking peptide is $(GGGGS)_n$, where n=3, 4, 5, 6, 7, 8, 9, 10, 11, 12, 13, 14, 15, 16, 17, 18, 19, 20, or more (SEQ ID NO: 105) and which bridges approximately 3.5 nm between the carboxy terminus of one variable region and the amino terminus of the other variable region. Linkers of other sequences have been designed and used. Methods of producing such antibodies are described in for instance U.S. Pat. No. 4,946,778, Pluckthun in The Pharmacology of Monoclonal Antibodies, vol. 113, Rosenburg and Moore eds. Springer-Verlag, New York, pp. 269-315 (1994), Bird et al., *Science* 242, 423-426 (1988), Huston et al., *PNAS USA* 85, 5879-5883 (1988) and McCafferty et al., *Nature* 348, 552-554 (1990). Linkers can in turn be modified for additional functions, such as attachment of drugs or attachment to solid supports. Fab and scFab fragments may be stabilized via natural disulfide bonds between the CL domain and the CH1 domain. Antigen-binding fragments comprising a heavy chain variable domain (VH) and a light chain variable domain (VL), such as the Fab, crossFab, scFv and scFab fragments as described herein might be further stabilized by introducing interchain disulfide bridges between the VH and the VL domain. Accordingly, in one embodiment, the Fab fragment(s), the crossFab fragment(s), the scFv fragment(s) and/or the scFab fragment(s) comprised in the antigen-binding receptors according to the invention might be further stabilized by generation of interchain disulfide bonds via insertion of cysteine residues. Such stabilized antigen-binding moieties are referred to by the term "ds". Cysteine engineered antibodies, in some embodiments, are made reactive for conjugation with linker-degrader intermediates described herein, by treatment with a reducing agent such as DTT (Cleland's reagent, dithiothreitol) or TCEP (tris(2-carboxyethyl)phosphine hydrochloride; Getz et al. (1999) *Anal. Biochem.* Vol 273:73-80; Soltec Ventures, Beverly, Mass.) followed by re-formation of the inter-chain disulfide bonds (re-oxidation) with a mild oxidant such as dehydroascorbic acid.

Also provided herein are affinity matured antibodies. For example, affinity matured antibodies can be produced by any suitable procedure (see, e.g., Marks et al., 1992, *Bio/Technology,* 10:779-783; Barbas et al., 1994, *Proc Nat. Acad. Sci, USA* 91:3809-3813; Schier et al., 1995, *Gene,* 169:147-155; Yelton et al., 1995, *J. Immunol.,* 155:1994-2004; Jackson et al., 1995, *J. Immunol.,* 154(7):3310-9; Hawkins et al, 1992, *J. Mol. Biol.,* 226:889-896; and WO2004/058184). The following methods may be used for adjusting the affinity of an antibody and for characterizing a CDR. One way of characterizing a CDR of an antibody and/or altering (such as improving) the binding affinity of a polypeptide, such as an antibody, is termed "library scanning mutagenesis." Generally, library scanning mutagenesis works as follows. One or more amino acid position in the CDR is replaced with two or more (such as 3, 4, 5, 6, 7, 8, 9, 10, 11, 12, 13, 14, 15, 16, 17, 18, 19, or 20) amino acids. This generates small libraries of clones (in some embodiments, one for every amino acid position that is analyzed), each with a complexity of two or more members (if two or more amino acids are substituted at every position). Generally, the library also includes a clone comprising the native (unsubstituted) amino acid. A small number of clones, for example, about 20-80 clones (depending on the complexity of the library), from each library can be screened for binding specificity or affinity to the target polypeptide (or other binding target), and candidates with increased, the same, decreased, or no binding are identified. Binding affinity may be determined using Biacore surface plasmon resonance analysis, which detects differences in binding affinity of about 2-fold or greater. Biacore can be particularly useful when the starting antibody already binds with a relatively high affinity, for example, a $K_D$ of about 10 nM or lower.

In some instances, an antibody or antigen-binding fragment is bi-specific or multi-specific and can specifically bind to more than one antigen. In some cases, such a bi-specific or multi-specific antibody or antigen-binding fragment can specifically bind to 2 or more different antigens. In some cases, a bi-specific antibody or antigen-binding fragment can be a bivalent antibody or antigen-binding fragment. In some cases, a multi specific antibody or antigen-binding fragment can be a bivalent antibody or antigen-binding fragment, a trivalent antibody or antigen-binding fragment, or a quatravalent antibody or antigen-binding fragment.

An antibody or antigen-binding fragment described herein can be an isolated, purified, recombinant, or synthetic.

As used herein, the term "affinity" refers to the equilibrium constant for the reversible binding of two agents and is expressed as $K_D$. The binding affinity ($K_D$) of an antibody or antigen-binding fragment described herein can be less than 50 nM, 49 nM, 48 nM, 47 nM, 46 nM, 45 nM, 44 nM, 43 nM, 42 nM, 41 nM, 40 nM, 39 nM, 38 nM, 37 nM, 36 nM, 35 nM, 34 nM, 33 nM, 32 nM, 31 nM, 30 nM, 29 nM, 28 nM, 27 nM, 26 nM, 25 nM, 24 nM, 23 nM, 22 nM, 21 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, 1 nM, 990 pM, 980 pM, 970 pM, 960 pM, 950 pM, 940 pM, 930 pM, 920 pM, 910 pM, 900 pM, 890 pM, 880 pM, 870 pM, 860 pM, 850 pM, 840 pM, 830 pM, 820 pM, 810 pM, 800 pM, 790 pM, 780 pM, 770 pM, 760 pM, 750 pM, 740 pM, 730 pM, 720 pM, 710 pM, or 700 pM, or any integer therebetween.

Binding affinity may be determined using surface plasmon resonance (SPR), Kinexa Biocensor, scintillation proximity assays, enzyme linked immunosorbent assay (ELISA), ORIGEN immunoassay (IGEN), fluorescence quenching, fluorescence transfer, yeast display, or any combination thereof. Binding affinity may also be screened using a suitable bioassay.

As used herein, the term "avidity" refers to the resistance of a complex of two or more agents to dissociation after dilution. Apparent affinities can be determined by methods such as an enzyme linked immunosorbent assay (ELISA) or any other technique familiar to one of skill in the art. Avidities can be determined by methods such as a Scatchard analysis or any other technique familiar to one of skill in the art.

An antibody or antigen-binding fragment can be modified by making one or more substitutions in the amino acid sequence using a conservative or a non-conservative substitution such that the resulting modified antibody exhibits about 80% homology to a sequence described herein.

The phrase "conservative amino acid substitution" refers to grouping of amino acids on the basis of certain common properties. A functional way to define common properties between individual amino acids is to analyze the normalized frequencies of amino acid changes between corresponding proteins of homologous organisms (Schulz, G. E. and R. H. Schirmer, Principles of Protein Structure, Springer-Verlag). According to such analyses, groups of amino acids may be defined where amino acids within a group exchange preferentially with each other, and therefore resemble each other most in their impact on the overall protein structure. Examples of amino acid groups defined in this manner include:

(i) a charged group, consisting of Glu and Asp, Lys, Arg and His;

(ii) a positively-charged group, consisting of Lys, Arg and His;

(iii) a negatively-charged group, consisting of Glu and Asp;

(iv) an aromatic group, consisting of Phe, Tyr and Trp;

(v) a nitrogen ring group, consisting of His and Trp;

(vi) a large aliphatic non-polar group, consisting of Val, Leu and Ile;

(vii) a slightly-polar group, consisting of Met and Cys;

(viii) a small-residue group, consisting of Ser, Thr, Asp, Asn, Gly, Ala, Glu, Gln and Pro;

(ix) an aliphatic group consisting of Val, Leu, Ile, Met and Cys; and (x) a small hydroxyl group consisting of Ser and Thr.

In addition to the groups presented above, each amino acid residue may form its own group, and the group formed by an individual amino acid may be referred to simply by the one and/or three letter abbreviation for that amino acid commonly used in the art as described above.

A "conserved residue" is an amino acid that is relatively invariant across a range of similar proteins. Often conserved residues will vary only by being replaced with a similar amino acid, as described above for "conservative amino acid substitution."

The letter "x" or "xaa" as used in amino acid sequences herein is intended to indicate that any of the twenty standard amino acids may be placed at this position unless specifically noted otherwise.

As used herein, "identity" means the percentage of identical nucleotide or amino acid residues at corresponding positions in two or more sequences when the sequences are aligned to maximize sequence matching, i.e., taking into account gaps and insertions. Identity can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. *Applied Math.*, 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., *Nucleic Acids Research* 12(1): 387 (1984)), BLASTP, BLASTN, and FASTA (Altschul, S. F. et al., *J. Molec. Biol.* 215: 403-410 (1990) and Altschul et al. *Nuc. Acids Res.* 25: 3389-3402 (1997)). The BLAST X program is publicly available from NCBI and other sources (BLAST Manual, Altschul, S., et al., NCBI NLM NIH Bethesda, Md. 20894; Altschul, S., et al., *J. Mol. Biol.* 215: 403-410 (1990). The well-known Smith Waterman algorithm may also be used to determine identity.

"Polynucleotide" or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component.

Other types of modifications include, for example, "caps," substitution of one or more of the naturally-occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses, or lyxoses, pyranose sugars, furanose sugars, sedoheptuloses, acyclic analogs, and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), (O)NR$_2$ ("amidate"), P(O)R, P(O)OR', CO, or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl, or araldyl. Not all linkages in a polynucleotide need be identical. The preceding description applies to all polynucleotides referred to herein, including RNA and DNA.

In one aspect, provided herein is one or more RNA molecules that encode one or more of the antibodies or antigen-binding fragments described herein. Such one or more RNA molecules may be present in a vector for administration to a subject.

Provide herein are polynucleotides (such as RNA, for example mRNA) encoding antibodies or antigen-binding fragments that can specifically bind to SARS-Cov-2. Antibody or antigen-binding fragments encoded by polynucleotides can include antibodies or antigen-binding fragments. Polynucleotides can be administered to a subject to prevent infection of the subject by SARS-Cov-2 or to treat a subject infected by SARS-Cov-2. In some cases, antibodies or antigen-binding fragments can be produced in a subject that has been administered a polynucleotide described herein.

Polynucleotides can comprise genetic material encoding an antibody or antigen-binding fragment (e.g., DNA or mRNA). In some cases, polynucleotides can be in a vector, such as a viral vector or an artificial chromosome such as a human artificial chromosome. In some cases, polynucleotides can additionally comprise a promoter, a terminator, a sequence encoding a tag, a sequence encoding a second antibody or antigen-binding fragment, or a sequence encoding a molecule that can aid in folding or function of the antibody or antigen-binding fragment.

In some cases, polynucleotides can be used to prevent and/or treat disease caused by SARS-Cov-2 or a similar virus (e.g., COVID-19); i.e., polynucleotides can have prophylactic or therapeutic uses, or both prophylactic and therapeutic uses. Accordingly, the present disclosure provides methods to prevent and/or treat infection by SARS-Cov-2. In some cases, such methods can comprise administering to a subject one or more mRNA molecules encoding an antibody or antigen-binding fragment that can specifically bind to SARS-Cov-2.

An antibody library herein can comprise a plurality of antibodies and/or antigen-binding fragments. The plurality of antibodies and/or antigen-binding fragments can be at least $1.0\times10^6$, $1.0\times10^7$, $1 0.0\times10^8$, $1.0\times10^9$, $1.0\times10^{10}$, $2.0\times10^{10}$, $3.0\times10^{10}$, $4.0\times10^{10}$, $5.0\times10^{10}$, $6.0\times10^{10}$, $7.0\times10^{10}$, $8.0\times10^{10}$, $9.0\times10^{10}$, or $10.0\times10^{10}$.

The practices of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Cabs, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); and The Antibodies (M. Zanetti and J. D. Capra, eds., Harwood Academic Publishers, 1995).

EXAMPLES

The application may be better understood by reference to the following non-limiting examples, which are provided as exemplary embodiments of the application. The following examples are presented in order to more fully illustrate embodiments and should in no way be construed, however, as limiting the broad scope of the application.

Example 1: Kinetics and Affinity Determination of an Anti-SARS-Cov-2 scFv by Surface Plasmon Resonance High-throughput surface plasmon resonance (SPR) kinetic experiments were performed on Carterra LSA Array SPR instrument (Carterra, Salt Lake City, Utah) equipped with HC200M sensor chip (catalog No. 4287, Carterra, Salt Lake City, Utah) at 25° C. Anti-COVID-19 scFv constructs were expressed with a V5 epitope tag to enable capture via immobilized anti-V5 antibody. Surfaces were prepared in HBSTE (10 mM HEPES pH 7.4, 150 mM NaCl, 3 mM EDTA, 0.01% (v/v) Tween-20) as running buffer. The capture surface was prepared by standard amine-coupling of anti-V5 tag antibody (catalog No. ab27671, Abcam, Cambridge, Mass.) on the entire chip surface as follows. The chip was activated with a 10-min injection of a freshly prepared 1:1:1 (v/v/v) mixture of 0.4 M 1-Ethyl-3-(3-Dimethylaminopropyl) carbodiimide hydrochloride (EDC)+0.1 M N-hydroxysulfosuccinimide (sNHS)+0.1 M 2-(N-morpholino) ethanesulfonic acid (MES) pH 5.5. Then, anti-V5 tag antibody was diluted to 50 μg/ml in 10 mM sodium acetate pH 4.3 and coupled for 14 min. Excess reactive esters were blocked with a 10-min injection of 1 M ethanolamine HCl pH 8.5. A library of anti-SARS-Cov-2 scFv clones was supplied as plates of crude bacterial periplasmic extracts (PPE) and diluted 2-fold in running buffer. ScFv samples were flow printed for 15-min in batches of 96 PPE's in parallel using the 96 channel printhead to generate a 384-ligand array comprising 1 spot per scFv. For the interaction analysis, the running buffer HBST (10 mM HEPES pH 7.4, 150 mM NaCl, 0.01% (v/v) Tween-20) was supplemented with 0.5 mg/ml BSA. Surfaces were stabilized with seven to eight buffer analyte injections. SARS-Cov-2, SARS-CoV-1, and MERS Receptor Binding Domain (RBD) proteins were prepared at concentrations of 0, 3.7, 11.1, 33.3, 100, 37, and 300 nM and these samples were injected as analyte for 5 min, allowing a 15-min dissociation time. Samples were injected in ascending concentration without any regeneration in between them. Binding data from the local reference spots were subtracted from the active spots and the nearest buffer blank analyte responses were subtracted to double-reference the data. The double-referenced data were fitted to a simple 1:1 *Langmuir* binding model in Carterra's Kinetic Inspection Tool to give kinetics ($k_a$, $k_d$), affinity ($K_D$), and $R_{max}$ value for each interaction.

| Clone ID | Captures RL (RU) | ka (M-1 s-1) | kd (s-1) | KD (nM) | Rmax (RU) |
|---|---|---|---|---|---|
| COVID19_P04_B10 | 1646 | 2.00E+05 | 5.00E-04 | 2.5 | 30 |
| COVID19_R01_C08 | 1578 | 7.66E+04 | 3.79E-03 | 49.5 | 52 |
| COVID19_P04_E10 | 1836 | 1.20E+05 | 5.30E-04 | 4.4 | 39 |
| COVID19_R01_B01 | 1136 | 4.40E+04 | 5.50E-04 | 12.5 | 18 |
| COVID19_R01_D02 | 1141 | 2.10E+05 | 5.80E-04 | 2.8 | 47 |
| COVID19_R01_A04 | 1230 | 1.10E+06 | 1.20E-02 | 10.9 | 30 |
| COVID19_P04_B03 | 1667 | 7.16E+05 | 1.41E-02 | 19.7 | 27 |
| COVID19_P04_B09 | 1544 | 2.30E+05 | 3.20E-04 | 1.4 | 15 |
| COVID19_P04_D08 | 1533 | 2.79E+05 | 1.13E-02 | 40.7 | 28 |
| COVID19_P04_G03 | 1742 | 6.30E+04 | 4.50E-04 | 7.1 | 30 |
| COVID19_R01_B10 | 1107 | 9.69E+04 | 2.94E-03 | 30.4 | 21 |
| COVID19_P04_C07 | 1899 | 1.70E+05 | 7.40E-03 | 43.5 | 52 |
| COVID19_P04_G05 | 1750 | 7.90E+04 | 5.70E-05 | 0.72 | 15 |

The described clones each had a superior binding affinity of less than 50 nM. The majority of the clones were identified as binding solely to SARS-Cov-2 (COV2), however, one clone (COVID19_B_R02_C08) was found to not only bind to Sars-Cov-2, but also to SARS1, SARS2, and Middle East Respiratory Syndrome (MERS) viruses.

| Clone ID | Binding Affinity For: |
|---|---|
| COVID19_P04_B10 | COV2 |
| COVID19_B_R02_C08 | COV2 + SARS1 + SARS2 + MERS |
| COVID19_P04_E10 | COV2 |
| COVID19_B_R02_B01 | COV2 |
| COVID19_B_R02_D02 | COV2 |
| COVID19_B_R02_A04 | COV2 |
| COVID19_P04_B03 | COV2 |
| COVID19_P04_B09 | COV2 |
| COVID19_P04_D08 | COV2 |
| COVID19_P04_G03 | COV2 |
| COVID19_B_R02_B10 | COV2 |
| COVID19_P04_C07 | COV2 |
| COVID19_P04_G05 | COV2 |

Example 2: In Vitro Neutralization Assay for SARS-Cov-2 Virus

Production and Titration of Pseudoviruses

For pseudovirus construction, spike genes from a SARS-CoV-2 virus strain, were codon-optimized for human cells and cloned into eukaryotic expression plasmid to generate the envelope recombinant plasmids. The pseudoviruses were produced and titrated using methods similar those described in Nie J. et al. (*Emerg Microbes Infect.* 2020 December; 9(1):680-686), 293T cells were transfected with pseudovirus vectors using Lipofectamine system (ThermoFisher) following the manufacturer's instruction. Twenty-four hours later, new media is replaced and after 48 h from the beginning of transfection SARS-Cov-2 pseudoviruses containing culture supernatants were harvested, filtered (0.45-µm pore size, Millipore, SLHP033RB) and stored at −80° C. in aliquots until use. The 50% tissue culture infectious dose (TCID50) of SARS-Cov-2 pseudovirus is determined using a single-use aliquot from the pseudovirus bank; all stocks were used only once to avoid inconsistencies that could have resulted from repeated freezing-thawing cycles. For titration of the SARS-Cov-2 pseudovirus, a 2-fold initial dilution is made in triplicates wells of 96-well culture plates followed by serial 3-fold dilutions (8 dilutions in total). The last column served as the cell control without the addition of pseudovirus. Then, 96-well plates were seeded with trypsin-treated Vero E6 mammalian transfectable cells adjusted to a pre-defined concentration. After 24 h incubation in a 5% $CO_2$ environment at 37° C., the culture supernatant is aspirated gently to leave 100 µl in each well; then, 100 µl of luciferase substrate is added to each well. Two min after incubation at room temperature, 150 µl of lysate is transferred to white solid 96-well plates for the detection of luminescence using a microplate luminometer (PerkinElmer). The positive well is determined as ten-fold relative luminescence unit (RLU) values higher than the cell background. The 50% tissue culture infectious dose (TCID50) is calculated using the Reed-Muench method, as described in Nie J et al. Id. In some cases the pseudovirus included a GFP reporter instead of Luciferase; in these cases, GFP fluorescence is measured by flow cytometry.

Pseudovirus-Based Neutralization Assay

Neutralization is measured by the reduction in luciferase gene expression or GFP gene expression as described previously Nie J et al. Id. The 50% inhibitory dilution (EC50) is defined as the dilution of the tested antibodies at which the relative light units (RLUs) were reduced by 50% compared with the virus control wells (virus+cells) after subtraction of the background RLUs in the control groups with cells only. In brief, pseudovirus in the TCID50 determined above is incubated with serial dilutions of the test samples (six dilutions in a 3-fold step-wise manner) in duplicate for 1 h at 37° C., together with the virus control and cell control wells in triplicate. Then, freshly trypsinized cells were added to each well. Following 24 h of incubation in a 5% CO2 environment at 37° C., the luminescence or fluoresce (depending on the reporter gene used) is measured as described above (relating to pseudovirus titration). The EC50 values were calculated with non-linear regression, i.e., log (inhibitor) vs. response (four parameters), using GraphPad Prism 8 (GraphPad Software, Inc., San Diego, Calif., USA).

Results

Neutralization has been observed for all clones tested. Tm1 (° C.) and IC50 (µg/mL) for a subset of the clones is as follows:

| Clone ID | Average Tm1 (° C.) | IC50 [µg/mL] plaque | IC50 [µg/mL] pseudotyped lenti neutralization |
|---|---|---|---|
| COVID19_R01_D02 | 72.3 | <3 | 0.62 |
| COVID19_R01_C08 | 68 | + | |
| COVID19_P04_G05 | 70.2 | | |
| COVID19_P04_B09 | 72.5 | | |
| COVID19_P04_B10 | 56.3 | | |
| COVID19_P04_E10 | 73.9 | + | |

Example 3: Competition of SARS-Cov-2/ACE2 Interaction with Anti-SARS-Cov-2 scFv by Biolayer Interferometry Competition assay of the interaction of SARS-Cov-2 with ACE2 is conducted in a classical sandwich and a premix assay format using a ForteBio Octet HTX biolayer interferometry instrument (Molecular Devices ForteBio LLC, Fremont, Calif.) at 25° C. with running buffer HBST (10 mM HEPES pH 7.4, 150 mM NaCl, 0.01% (v/v) Tween-20, pH 7.4) supplemented with 1 mg/mL BSA.

An Anti-V5 tag antibody (catalog No. ab27671, Abcam, Cambridge, Mass.) is biotinylated with a 5:1 molar ratio of sulfo-NHS-LC-LC-biotin (catalog No. 21338, ThermoFisher Scientific, Waltham, Mass.) and buffer exchanged into PBS using ThermoFisher Zeba 7K MWCO columns (catalog No. 89883, ThermoFisher Scientific, Waltham, Mass.).

Streptavidin sensor tips (catalog no. 18-5021, Molecular Devices ForteBio LLC, Fremont, Calif.) are equilibrated in buffer for 10-min before the run. Sample plates are agitated at 1000 rpm. At the start of the run, sensors are exposed to buffer for 60 sec to establish a baseline. The biotinylated anti-V5 tag antibody at 7 µg/mL are loaded onto the sensors for 5-min to prepare an anti-V5 surface. To block remaining free biotin binding sites, all sensors are exposed for 5-min with 20 µM amine-PEG2-biotin (catalog No. 21346, ThermoFisher Scientific, Waltham, Mass.) followed by two alternating 30-sec cycles of 10 mM glycine-HCl pH1.7 and buffer to precondition the sensors.

For the classical sandwich assay format, a baseline in buffer is established for 60-sec and anti-SARS-Cov-2 scFv clones as PPE undiluted are captured for 2-min onto the anti-V5 sensor tips. Baseline in buffer is recorded for 60-sec followed by association of SARS-Cov-2 at 100 nM for 2-min, a quick wash in buffer for 15-sec, and sandwiching of 500 nM ACE2 or buffer for 2-min. After each classical sandwich cycle, sensors are regenerated with two alternating 30-sec cycles of 10 mM glycine-HCl pH1.7 and buffer.

For the premix assay format, a baseline in buffer is established for 60-sec and anti-SARS-Cov-2 scFv clones as PPE undiluted are captured for 2-min onto the anti-V5 sensor tips. Baseline in buffer is recorded for 60-sec followed by association of buffer, a premixed complex of 100 nM SARS-Cov-2+500 nM ACE2, or 100 nM SARS-Cov-2. Dissociation in buffer is measured for 30-sec. After each binding cycle, sensors are regenerated with two alternating 30-sec cycles of 10 mM glycine-HCl pH1.7 and buffer. Capture of biotinylated ACE2 at 10 µg/mL is included as a self-blocking control in both assays.

Example 4: In Vivo Hamster Model for Sars-COV2 Infections

Competent 6-8 weeks old Syrian golden hamsters females (Charles River Laboratories or Harlan Laboratories) are housed three per cage in a biosafety level 3-4 animal facility in UTMB Galveston. Animals will be acclimatized in the BSL-3-4 biosafety containment 3-5 days before the experiment begins. Animal will be housed and treated as recommended by Institutional Biosafety and the Institutional Animal Care and Use Committees.

Animals are injected IP with 0.5-1 mL of either saline, a therapeutic antibody at 10 mg/Kg (as disclosed herein), or an isotype control antibody at 10 mg/Kg, 24 h before viral infection. Animals are acclimatized in the ABSL-3 biosafety containment. On the day of infection, hamsters (5 per group) will be inoculated with PBS or 10E5 ($1 \times 10^5$) virus load via nasal cavity in a total volume of 100 µL (50 µL into each naris).

Hamsters' bodyweight and viable signs (such as ruffled hair and lack of movement) will be monitored and recorded twice daily for 3 days and virus titers will be measured from a nasal swab on day 2. Hamsters will be sacrificed on day 3 and virus titers in homogenates of lung tissues will be determined.

H&E-stained lung tissues will be evaluated by a suitable scientist, medical professional, or veterinary professional (e.g., trained in pathology) to determine the severity of infection and amount of protection provided by the neutralizing antibodies. To determine the TCID50 in the lungs, tissues will be homogenized and spun down and the supernatants will be removed and analyzed by a TCID50 assay as described in a previous Example, above.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An antibody or an antigen-binding fragment that selectively binds to a severe acute respiratory syndrome coronavirus 2 (SARS-CoV-2), that comprises a variable heavy chain (VH) complementarity determining region 1 (CDR1) having an amino acid sequence of SEQ ID NO: 39; a VH CDR2 having an amino acid sequence of SEQ ID NO: 53; a VH CDR3 having an amino acid sequence of SEQ ID NO: 68; a variable light chain (VL) CDR1 having an amino acid sequence of SEQ ID NO: 7; a VL CDR2 having an amino acid sequence of SEQ ID NO: 15; and a VL CDR3 having an amino acid sequence of SEQ ID NO: 25.

2. The antibody or the antigen-binding fragment of claim 1, that comprises a VH having an amino acid sequence that is at least 90% identical to SEQ ID NO: 81 and a VL having an amino acid sequence that is at least 90% identical to SEQ ID NO: 93.

3. The antibody or the antigen-binding fragment of claim 2, wherein the antibody comprises a monoclonal antibody, a grafted antibody, a chimeric antibody, a human antibody, or a humanized antibody.

4. The antibody or the antigen-binding fragment of claim 2, wherein the binding affinity is less than 50 nanomolar (nM).

5. The antibody or the antigen-binding fragment of claim 2, wherein the antigen-binding fragment comprises a Fab, a Fab', a F(ab')$_2$, a variable fragment (Fv), a triabody, a tetrabody, a minibody, a bispecific F(ab')$_2$, a trispecific F(ab')$_2$, a diabody, a bispecific diabody, a single chain variable fragment (scFv), a scFv-Fc, a Fab-Fc, a VHH, or a bispecific scFv.

6. A method of preventing or treating a SARS-CoV-2 viral infection or COVID19 in a subject in need thereof, comprising administering to the subject the antibody or the antigen-binding fragment of claim 1.

7. The method of any claim 6, that further comprises administering one or more additional therapies or drugs to the subject.

8. A method of diagnosing a subject as being infected with a SARS-CoV-2 virus or suspected of being infected with a SARS-CoV-2 virus, the method comprising contacting a sample obtained from the subject with the antibody or the antigen-binding fragment of claim 1; detecting the presence or absence of an antibody/SARS-CoV-2 virus complex or an antigen-binding fragment/SARS-CoV-2 virus complex; and diagnosing the subject as being infected with a SARS-Cov-2 virus when the presence of the antibody/SARS-CoV-2 virus complex or the antigen-binding fragment/SARS-CoV-2 virus complex is detected.

9. The method of claim 8, wherein the sample comprises a nasal swab, a tissue sample, saliva, or blood.

10. The method of claim 8, wherein detecting the presence or absence of the antibody/SARS-CoV-2 virus complex or the antigen-binding fragment/SARS-CoV-2 virus complex comprises an enzyme linked immunosorbent assay (ELISA), an immunospot assay, a lateral flow assay, flow cytometry, immunohistochemistry, or a western blot.

11. An antibody or an antigen-binding fragment that selectively binds to a SARS-CoV-2, that comprises a VH having an amino acid sequence of SEQ ID NO: 81 and a VL having an amino acid sequence of SEQ ID NO: 93.

12. The antibody or the antigen-binding fragment of claim 1, wherein the binding affinity is less than 50 nM.

13. The antibody or the antigen-binding fragment of claim 1, wherein the antigen-binding fragment comprises a Fab, a Fab', a F(ab')$_2$, a variable fragment (Fv), a triabody, a tetrabody, a minibody, a bispecific F(ab')$_2$, a trispecific F(ab')$_2$, a diabody, a bispecific diabody, a single chain variable fragment (scFv), a scFv-Fc, a Fab-Fc, a VHH, or a bispecific scFv.

14. The antibody or the antigen-binding fragment of claim 1, wherein the antibody is an IgG, an IgM, an IgE, an IgA, an IgD, or is derived therefrom.

15. The antibody or the antigen-binding fragment of claim 2, wherein the antibody is an IgG, an IgM, an IgE, an IgA, an IgD, or is derived therefrom.

16. An antibody or an antigen-binding fragment that selectively binds to a SARS-CoV-2, that comprises:
   (i) a VH CDR1 having an amino acid sequence of SEQ ID NO: 41, a VH CDR2 having an amino acid sequence of SEQ ID NO: 55, a VH CDR3 having an amino acid sequence of SEQ ID NO: 70, a VL CDR1 having an amino acid sequence of SEQ ID NO: 9, a VL CDR2 having an amino acid sequence of SEQ ID NO: 14, and a VL CDR3 having an amino acid sequence of SEQ ID NO: 23;
   (ii) a VH CDR1 having an amino acid sequence of SEQ ID NO: 32, a VH CDR2 having an amino acid sequence of SEQ ID NO: 46, a VH CDR3 having an amino acid sequence of SEQ ID NO: 61, a VL CDR1 having an amino acid sequence of SEQ ID NO: 4, a VL CDR2 having an amino acid sequence of SEQ ID NO: 13, and a VL CDR3 having an amino acid sequence of SEQ ID NO: 20;
   (iii) a VH CDR1 having an amino acid sequence of SEQ ID NO: 36, a VH CDR2 having an amino acid sequence of SEQ ID NO: 50, a VH CDR3 having an amino acid sequence of SEQ ID NO: 65, a VL CDR1 having an amino acid sequence of SEQ ID NO: 6, a VL CDR2 having an amino acid sequence of SEQ ID NO: 14, and a VL CDR3 having an amino acid sequence of SEQ ID NO: 23; or (iv) a VH CDR1 having an amino acid sequence of SEQ ID NO: 30, a VH CDR2 having an amino acid sequence of SEQ ID NO: 44, a VH CDR3 having an amino acid sequence of SEQ ID NO: 59, a VL CDR1 having an amino acid sequence of SEQ ID NO: 4, a VL CDR2 having an amino acid sequence of SEQ ID NO: 13, and a VL CDR3 having an amino acid sequence of SEQ ID NO: 20.

* * * * *

SEQUENCE LISTING

<160> NUMBER OF SEQ ID NOS: 109

<210> SEQ ID NO 1
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 2
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: I or V
<220> FEATURE:
<221> NAME/KEY: MOD_RES
<222> LOCATION: (7)..(7)
<223> OTHER INFORMATION: G, R, or S
<220> FEATURE:
<221> NAME/KEY: MOD_RES
<222> LOCATION: (8)..(8)
<223> OTHER INFORMATION: R, S, or T
<220> FEATURE:
<221> NAME/KEY: MOD_RES
<222> LOCATION: (9)..(9)
<223> OTHER INFORMATION: N or Y
<220> FEATURE:
<221> NAME/KEY: MOD_RES
<222> LOCATION: (11)..(11)
<223> OTHER INFORMATION: A, N, or S

<400> SEQUENCE: 3

Phe Ala Ser Gln Ser Xaa Xaa Xaa Xaa Leu Xaa
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 4

Arg Ala Ser Gln Ser Ile Ser Ser Tyr Leu Asn
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Ala Ser Gln Ser Ile Gly Thr Tyr Leu Ser
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Ala Ser Gln Ser Val Arg Ser Asn Leu Ala
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Ala Ser Gln Ser Val Ser Asn Asn Leu Ala
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Ala Ser Gln Ser Val Ser Ser Ser Tyr Leu Ala
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Ala Ser Gln Ser Val Ser Ser Asn Leu Ala
1               5                   10

<210> SEQ ID NO 10
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 10

Trp Tyr Gln Gln Lys Pro Gly Lys Ala Pro Lys Leu Leu Ile Tyr
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Trp Tyr Gln Gln Lys Pro Gly Gln Ala Pro Arg Leu Leu Ile Tyr
1               5                   10                  15

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: A, G, or S
<220> FEATURE:
<221> NAME/KEY: MOD_RES
<222> LOCATION: (4)..(4)
<223> OTHER INFORMATION: S or T
<220> FEATURE:
<221> NAME/KEY: MOD_RES
<222> LOCATION: (5)..(5)
<223> OTHER INFORMATION: L or R
<220> FEATURE:
<221> NAME/KEY: MOD_RES
<222> LOCATION: (6)..(6)
<223> OTHER INFORMATION: Q or A
<220> FEATURE:
<221> NAME/KEY: MOD_RES
<222> LOCATION: (7)..(7)
<223> OTHER INFORMATION: S or T

<400> SEQUENCE: 12

Xaa Ala Ser Xaa Xaa Xaa Xaa
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ala Ala Ser Ser Leu Gln Ser
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 14

Gly Ala Ser Thr Arg Ala Thr
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Ala Ser Thr Arg Ala Thr
1               5

<210> SEQ ID NO 16
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr
            20                  25                  30

<210> SEQ ID NO 17
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gly Val Pro Ser Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr
            20                  25                  30

<210> SEQ ID NO 18
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr
            20                  25                  30

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic

```
        peptide
<220> FEATURE:
<221> NAME/KEY: MOD_RES
<222> LOCATION: (3)..(3)
<223> OTHER INFORMATION: Q or H
<220> FEATURE:
<221> NAME/KEY: MOD_RES
<222> LOCATION: (4)..(4)
<223> OTHER INFORMATION: A, R, S, or Y
<220> FEATURE:
<221> NAME/KEY: MOD_RES
<222> LOCATION: (5)..(5)
<223> OTHER INFORMATION: G, L, N, S, or Y
<220> FEATURE:
<221> NAME/KEY: MOD_RES
<222> LOCATION: (6)..(6)
<223> OTHER INFORMATION: N or S
<220> FEATURE:
<221> NAME/KEY: MOD_RES
<222> LOCATION: (7)..(7)
<223> OTHER INFORMATION: L, S, T, or W
<220> FEATURE:
<221> NAME/KEY: MOD_RES
<222> LOCATION: (8)..(8)
<223> OTHER INFORMATION: P or Q
<220> FEATURE:
<221> NAME/KEY: MOD_RES
<222> LOCATION: (9)..(9)
<223> OTHER INFORMATION: L, P, or V

<400> SEQUENCE: 19

Cys Gln Xaa Xaa Xaa Xaa Xaa Xaa Xaa Thr Trp
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Cys Gln Gln Ser Tyr Ser Thr Pro Leu Thr Phe
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Cys Gln Gln Tyr Gly Ser Ser Pro Leu Thr Phe
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Cys Gln Gln Ser Leu Ser Leu Pro Val Thr Phe
1               5                   10

<210> SEQ ID NO 23
```

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Cys Gln Gln Arg Asn Asn Trp Pro Pro Thr Phe
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Cys Gln Gln Phe Gly Thr Ser Pro Pro Gly Leu Ser Phe
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Cys Gln Gln Tyr Asn Asn Trp Pro Pro Thr Phe
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Cys Gln Gln Ala Ser Ser Thr Pro Leu Thr Phe
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Gly Gly Thr Lys Val Glu Ile Lys Arg
1               5                   10

<210> SEQ ID NO 28
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28
```

Glu Val Gln Leu Val Glu Ser Gly Gly Gly Leu Val Gln Pro Gly Gly
1               5                   10                  15

Ser Leu Arg Leu Ser Cys Ala Ala Ser Gly
            20                  25

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: F or L
<220> FEATURE:
<221> NAME/KEY: MOD_RES
<222> LOCATION: (2)..(2)
<223> OTHER INFORMATION: T, S, R, or A
<220> FEATURE:
<221> NAME/KEY: MOD_RES
<222> LOCATION: (3)..(3)
<223> OTHER INFORMATION: F or V
<220> FEATURE:
<221> NAME/KEY: MOD_RES
<222> LOCATION: (4)..(4)
<223> OTHER INFORMATION: S or T
<220> FEATURE:
<221> NAME/KEY: MOD_RES
<222> LOCATION: (5)..(5)
<223> OTHER INFORMATION: D, N, or S
<220> FEATURE:
<221> NAME/KEY: MOD_RES
<222> LOCATION: (6)..(6)
<223> OTHER INFORMATION: H, N, or Y
<220> FEATURE:
<221> NAME/KEY: MOD_RES
<222> LOCATION: (7)..(7)
<223> OTHER INFORMATION: A, G, or Y
<220> FEATURE:
<221> NAME/KEY: MOD_RES
<222> LOCATION: (8)..(8)
<223> OTHER INFORMATION: M or I
<220> FEATURE:
<221> NAME/KEY: MOD_RES
<222> LOCATION: (9)..(9)
<223> OTHER INFORMATION: S, T, or N

<400> SEQUENCE: 29

Xaa Xaa Xaa Xaa Xaa Xaa Xaa Xaa Xaa
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Phe Arg Phe Ser Asp Ala Ala Ile His
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 31

Phe Thr Val Ser Ser Asn Tyr Met Asn
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Leu Ser Val Thr Ser Asn Tyr Met Ser
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Phe Thr Phe Ala Ser His Ala Met Ser
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Phe Thr Phe Thr Asn Tyr Ala Met Thr
1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Phe Thr Phe Ser Asn His Tyr Met Ser
1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Phe Thr Phe Ser Asn Ser Asp Met Asn
1               5

<210> SEQ ID NO 37
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 37

Phe Ser Phe Ser Ser Tyr Gly Met Ser
1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Phe Thr Phe Ser Asp His Tyr Met Ser
1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Phe Thr Phe Asp Asp Tyr Ala Met His
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Phe Thr Val Ser Ser Asn Tyr Met Ser
1               5

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Phe Ser Phe Ser Ser Tyr Gly Met Ser
1               5

<210> SEQ ID NO 42
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Trp Val Arg Gln Ala Pro Gly Lys Gly Leu Glu Trp Val
1               5                   10
```

```
<210> SEQ ID NO 43
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: A or S
<220> FEATURE:
<221> NAME/KEY: MOD_RES
<222> LOCATION: (2)..(2)
<223> OTHER INFORMATION: A or T
<220> FEATURE:
<221> NAME/KEY: MOD_RES
<222> LOCATION: (3)..(3)
<223> OTHER INFORMATION: I or M
<220> FEATURE:
<221> NAME/KEY: MOD_RES
<222> LOCATION: (4)..(4)
<223> OTHER INFORMATION: N or S
<220> FEATURE:
<221> NAME/KEY: MOD_RES
<222> LOCATION: (5)..(5)
<223> OTHER INFORMATION: G, R, N, T, or Y
<220> FEATURE:
<221> NAME/KEY: MOD_RES
<222> LOCATION: (6)..(6)
<223> OTHER INFORMATION: D, I, S, or T
<220> FEATURE:
<221> NAME/KEY: MOD_RES
<222> LOCATION: (8)..(8)
<223> OTHER INFORMATION: D, G, or S
<220> FEATURE:
<221> NAME/KEY: MOD_RES
<222> LOCATION: (9)..(9)
<223> OTHER INFORMATION: D, N, S, T, or Y
<220> FEATURE:
<221> NAME/KEY: MOD_RES
<222> LOCATION: (10)..(10)
<223> OTHER INFORMATION: I, K, or T
<220> FEATURE:
<221> NAME/KEY: MOD_RES
<222> LOCATION: (11)..(11)
<223> OTHER INFORMATION: E, F, or Y

<400> SEQUENCE: 43

Xaa Xaa Xaa Xaa Xaa Xaa Gly Xaa Xaa Xaa Xaa Tyr Ala
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ser Ala Ile Ser Gly Ser Gly Gly Ser Thr Tyr Tyr Ala
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45
```

```
Ser Val Val Tyr Pro Gly Gly Ser Thr Tyr Tyr Ala
1               5                   10
```

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

```
Ser Val Ile Tyr Pro Gly Gly Ser Thr Phe Tyr Ala
1               5                   10
```

<210> SEQ ID NO 47
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

```
Ser Gly Ile Ser Ser Asp Gly Ser Ile Thr Thr Tyr Ala
1               5                   10
```

<210> SEQ ID NO 48
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

```
Ser Thr Met Ser Asn Ile Gly Gly Asp Thr Tyr Tyr Ala
1               5                   10
```

<210> SEQ ID NO 49
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

```
Ser Ala Ile Ser Gly Ser Gly Gly Ser Thr Tyr Tyr Ala
1               5                   10
```

<210> SEQ ID NO 50
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

```
Ser Ala Ile Ser Gly Thr Gly Asp Thr Thr Glu Tyr Ala
1               5                   10
```

<210> SEQ ID NO 51
<211> LENGTH: 13
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 51

Ser Ala Met Asn Arg Asp Gly Ser Tyr Ile Tyr Tyr Ala
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ser Ala Ile Ser Thr Ser Gly Asp Ser Thr Phe Tyr Ala
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ala Ile Ile Tyr Glu Gly Gly Ser Pro His Tyr Ala
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ser Val Ile Tyr Pro Gly Gly Ser Thr Phe Tyr Ala
1               5                   10

<210> SEQ ID NO 55
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ser Ala Met Asn Arg Asp Gly Ser Tyr Ile Tyr Tyr Ala
1               5                   10

<210> SEQ ID NO 56
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Asp Ser Val Lys Gly Arg Phe Thr Ile Ser Arg Asp Asn Ser Lys Asn
1               5                   10                  15
```

```
Thr Leu Tyr Leu Gln Met Asn Ser Leu Arg Ala Glu Asp Thr Ala Val
            20                  25                  30

Tyr Tyr

<210> SEQ ID NO 57
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Asp Ser Val Lys Gly Arg Phe Thr Ile Ser Arg Asp Asn Ser Lys Asn
1               5                   10                  15

Thr Leu Tyr Leu Gln Met Asn Asn Leu Arg Ala Glu Asp Thr Ala Val
            20                  25                  30

Tyr Tyr

<210> SEQ ID NO 58
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: N, R, or S
<220> FEATURE:
<221> NAME/KEY: MOD_RES
<222> LOCATION: (7)..(7)
<223> OTHER INFORMATION: A, L, V, or Y
<220> FEATURE:
<221> NAME/KEY: MOD_RES
<222> LOCATION: (8)..(8)
<223> OTHER INFORMATION: G, M, or Y
<220> FEATURE:
<221> NAME/KEY: MOD_RES
<222> LOCATION: (9)..(9)
<223> OTHER INFORMATION: I, L, or F
<220> FEATURE:
<221> NAME/KEY: MOD_RES
<222> LOCATION: (10)..(10)
<223> OTHER INFORMATION: D or G

<400> SEQUENCE: 58

Cys Ala Arg Asp Arg Xaa Xaa Xaa Xaa Xaa Tyr Trp
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Cys Ala Arg Asp Arg Ser Tyr Gly Ile Asp Tyr Trp
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 60

Cys Ala Arg Asp Arg Ser Tyr Tyr Leu Asp Tyr Trp
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Cys Ala Arg Asp Arg Ser Tyr Tyr Leu Asp Tyr Trp
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Cys Ala Arg Asp Arg Gly Trp Tyr Leu Asp Tyr Trp
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Cys Ala Arg Asp Arg Arg Val Tyr Leu Asp Tyr Trp
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Cys Ala Arg Asp Arg Ser Tyr Tyr Leu Asp Tyr Trp
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Cys Ala Arg Asp Arg Ser Leu Met Leu Asp Tyr Trp
1               5                   10

<210> SEQ ID NO 66

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Cys Ala Arg Asp Arg Ser Tyr Tyr Val Gly Tyr Trp
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Cys Ala Arg Asp Arg Ser Tyr Tyr Leu Asp Tyr Trp
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Cys Ala Arg Asp Arg Ser Gly Tyr Leu Asp Tyr Trp
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Cys Ala Arg Asp Arg Ser Tyr Tyr Leu Asp Tyr Trp
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Cys Ala Arg Asp Arg Ser Tyr Tyr Val Gly Tyr Trp
1               5                   10

<210> SEQ ID NO 71
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71
```

Gly Gln Gly Thr Leu Val Thr Val Ser Ser
1               5                   10

<210> SEQ ID NO 72
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Arg Phe Ser Asp Ala
            20                  25                  30

Ala Ile His Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ser Tyr Gly Ile Asp Tyr Trp Gly Gln Gly Thr Leu
            100                 105                 110

Val Thr Val Ser Ser
            115

<210> SEQ ID NO 73
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Asn Trp Val Arg Gln Ala Pro Gly Lys Gly Leu Glu Trp Val
        35                  40                  45

Ser Val Val Tyr Pro Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Arg Ser Tyr Tyr Leu Asp Tyr Trp Gly Gln Gly Thr Leu Val
            100                 105                 110

Thr Val Ser Ser
        115

<210> SEQ ID NO 74
<211> LENGTH: 116
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Ser Val Thr Ser Asn
            20                  25                  30

Tyr Met Ser Trp Val Arg Gln Ala Pro Gly Lys Gly Leu Glu Trp Val
        35                  40                  45

Ser Val Ile Tyr Pro Gly Gly Ser Thr Phe Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Arg Ser Tyr Tyr Leu Asp Tyr Trp Gly Gln Gly Thr Leu Val
            100                 105                 110

Thr Val Ser Ser
        115

<210> SEQ ID NO 75
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ala Ser His
            20                  25                  30

Ala Met Ser Trp Val Arg Gln Ala Pro Gly Lys Gly Leu Glu Trp Val
        35                  40                  45

Ser Gly Ile Ser Ser Asp Gly Ser Ile Thr Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Trp Tyr Leu Asp Tyr Trp Gly Gln Gly Thr Leu
            100                 105                 110

Val Thr Val Ser Ser
        115

<210> SEQ ID NO 76
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr

```
                    20                  25                  30
Ala Met Thr Trp Val Arg Gln Ala Pro Gly Lys Gly Leu Glu Trp Val
                35                  40                  45

Ser Thr Met Ser Asn Ile Gly Gly Asp Thr Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Arg Val Tyr Leu Asp Tyr Trp Gly Gln Gly Thr Leu
            100                 105                 110

Val Thr Val Ser Ser
        115

<210> SEQ ID NO 77
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn His
            20                  25                  30

Tyr Met Ser Trp Val Arg Gln Ala Pro Gly Lys Gly Leu Glu Trp Val
                35                  40                  45

Ser Ala Ile Ser Gly Ser Gly Gly Ser Thr Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ser Tyr Tyr Leu Asp Tyr Trp Gly Gln Gly Thr Leu
            100                 105                 110

Val Thr Val Ser Ser
        115

<210> SEQ ID NO 78
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ser
            20                  25                  30

Asp Met Asn Trp Val Arg Gln Ala Pro Gly Lys Gly Leu Glu Trp Val
                35                  40                  45

Ser Ala Ile Ser Gly Thr Gly Asp Thr Thr Glu Tyr Ala Asp Ser Val
            50                  55                  60

Lys Gly Arg Phe Thr Ile Ser Arg Asp Asn Ser Lys Asn Thr Leu Tyr
```

-continued

```
            65                  70                  75                  80
Leu Gln Met Asn Ser Leu Arg Ala Glu Asp Thr Ala Val Tyr Tyr Cys
                85                  90                  95

Ala Arg Asp Arg Ser Leu Met Leu Asp Tyr Trp Gly Gln Gly Thr Leu
            100                 105                 110

Val Thr Val Ser Ser
        115

<210> SEQ ID NO 79
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Gly Met Ser Trp Val Arg Gln Ala Pro Gly Lys Gly Leu Glu Trp Val
        35                  40                  45

Ser Ala Met Asn Arg Asp Gly Ser Tyr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ser Tyr Tyr Val Gly Tyr Trp Gly Gln Gly Thr Leu
            100                 105                 110

Val Thr Val Ser Ser
        115

<210> SEQ ID NO 80
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Ser Trp Val Arg Gln Ala Pro Gly Lys Gly Leu Glu Trp Val
        35                  40                  45

Ser Ala Ile Ser Thr Ser Gly Asp Ser Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Asn Leu Arg Ala Glu Asp Thr Ala Val Tyr Tyr Cys
                85                  90                  95

Ala Arg Asp Arg Ser Tyr Tyr Leu Asp Tyr Trp Gly Gln Gly Thr Leu
            100                 105                 110

Val Thr Val Ser Ser
```

<210> SEQ ID NO 81
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ala Ile Ile Tyr Glu Gly Gly Ser Pro His Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Arg Ser Gly Tyr Leu Asp Tyr Trp Gly Gln Gly Thr Leu Val
            100                 105                 110

Thr Val Ser Ser
        115

<210> SEQ ID NO 82
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Pro Gly Gly Ser Thr Phe Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Arg Ser Tyr Tyr Leu Asp Tyr Trp Gly Gln Gly Thr Leu Val
            100                 105                 110

Thr Val Ser Ser
        115

<210> SEQ ID NO 83
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 83

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Gly Met Ser Trp Val Arg Gln Ala Pro Gly Lys Gly Leu Glu Trp Val
        35                  40                  45

Ser Ala Met Asn Arg Asp Gly Ser Tyr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ser Tyr Tyr Val Gly Tyr Trp Gly Gln Gly Thr Leu
            100                 105                 110

Val Thr Val Ser Ser
        115

<210> SEQ ID NO 84
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg
            100                 105

<210> SEQ ID NO 85
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Leu
                 85                  90                  95

Thr Phe Gly Gly Gly Thr Lys Val Glu Ile Lys Arg
                100                 105

<210> SEQ ID NO 86
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Leu
                 85                  90                  95

Thr Phe Gly Gly Gly Thr Lys Val Glu Ile Lys Arg
                100                 105

<210> SEQ ID NO 87
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Leu
                 85                  90                  95

Thr Phe Gly Gly Gly Thr Lys Val Glu Ile Lys Arg
                100                 105

<210> SEQ ID NO 88

```
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Gly Ser Ser Pro Leu
                85                  90                  95

Thr Phe Gly Gly Gly Thr Lys Val Glu Ile Lys Arg
            100                 105

<210> SEQ ID NO 89
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Gly Thr Tyr
            20                  25                  30

Leu Ser Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ser Leu Ser Leu Pro Val
                85                  90                  95

Thr Phe Gly Gly Gly Thr Lys Val Glu Ile Lys Arg
            100                 105

<210> SEQ ID NO 90
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Arg Ser Asn
            20                  25                  30
```

```
Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Arg Asn Asn Trp Pro Pro
                 85                  90                  95

Thr Phe Gly Gly Gly Thr Lys Val Glu Ile Lys Arg
                100                 105

<210> SEQ ID NO 91
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Arg Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Arg Asn Asn Trp Pro Pro
                 85                  90                  95

Thr Phe Gly Gly Gly Thr Lys Val Glu Ile Lys Arg
                100                 105

<210> SEQ ID NO 92
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Arg Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Phe Gly Thr Ser Pro Pro
                 85                  90                  95

Gly Leu Ser Phe Gly Gly Gly Thr Lys Val Glu Ile Lys Arg
                100                 105                 110
```

<210> SEQ ID NO 93
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Asn Asn
            20                  25                  30

Leu Ala Trp Tyr Gln Gln Lys Pro Gly Gln Ala Pro Arg Leu Leu Ile
        35                  40                  45

Tyr Asp Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Thr Phe Gly Gly Gly Thr Lys Val Glu Ile Lys Arg
            100                 105

<210> SEQ ID NO 94
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Glu Phe Thr Leu Thr Ile Ser Ser Leu Gln
65                  70                  75                  80

Ser Glu Asp Phe Ala Val Tyr Tyr Cys Gln Gln Ala Ser Ser Thr Pro
                85                  90                  95

Leu Thr Phe Gly Gly Gly Thr Lys Val Glu Ile Lys Arg
            100                 105

<210> SEQ ID NO 95
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn

```
                    20                  25                  30
Leu Ala Trp Tyr Gln Gln Lys Pro Gly Gln Ala Pro Arg Leu Leu Ile
             35                  40                  45
Tyr Gly Ala Ser Thr Arg Ala Thr Gly Ile Pro Ala Arg Phe Ser Gly
         50                  55                  60
Ser Gly Ser Gly Thr Glu Phe Thr Leu Thr Ile Ser Ser Leu Gln Ser
 65                  70                  75                  80
Glu Asp Phe Ala Val Tyr Tyr Cys Gln Gln Arg Asn Asn Trp Pro Pro
                 85                  90                  95
Thr Phe Gly Gly Gly Thr Lys Val Glu Ile Lys Arg
            100                 105
```

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

```
Phe Ala Phe Ser Ser Tyr Ala Met His
 1               5
```

<210> SEQ ID NO 97
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

```
Ala Val Ile Ser Tyr Asp Gly Ser Asn Lys Tyr Tyr Ala
 1               5                  10
```

<210> SEQ ID NO 98
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

```
Cys Ala Arg Asp Arg Ser Tyr Tyr Leu Asp Tyr
 1               5                  10
```

<210> SEQ ID NO 99
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

```
Arg Ala Ser Gln Ser Val Arg Ser Asn Leu Ala
 1               5                  10
```

<210> SEQ ID NO 100
<211> LENGTH: 7
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 100

Asp Ala Ser Thr Arg Ala Thr
1               5

<210> SEQ ID NO 101
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Cys Gln Gln Arg Ser Asn Trp Pro Pro Thr
1               5                   10

<210> SEQ ID NO 102
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Glu Val Gln Leu Val Gln Ser Gly Gly Gly Val Val Gln Pro Gly Lys
1               5                   10                  15

Ser Leu Arg Leu Ser Cys Ala Ala Ser Gly Phe Ala Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ser Tyr Tyr Leu Asp Tyr Trp Gly Gln Gly Thr Leu
            100                 105                 110

Val Thr Val Ser Ser
        115

<210> SEQ ID NO 103
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Glu Thr Thr Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Ser Asn
            20                  25                  30

Leu Ala Trp Tyr Gln Gln Lys Pro Gly Gln Ala Pro Arg Pro Leu Ile
        35                  40                  45

Tyr Asp Ala Ser Thr Arg Ala Thr Gly Ile Pro Asp Arg Phe Ser Gly
    50                  55                  60
```

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Val Lys
            100                 105

<210> SEQ ID NO 104
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 104

His His His His His His
1               5

<210> SEQ ID NO 105
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(100)
<223> OTHER INFORMATION: This sequence may encompass 3-20 "Gly Gly Gly
      Gly Ser" repeating units
<220> FEATURE:
<223> OTHER INFORMATION: See specification as filed for detailed
      description of substitutions and preferred embodiments

<400> SEQUENCE: 105

Gly Gly Gly Gly Ser Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
                20                  25                  30

Gly Gly Ser Gly Gly Gly Gly Ser Gly Gly Gly Gly Ser Gly Gly Gly
            35                  40                  45

Gly Ser Gly Gly Gly Gly Ser Gly Gly Gly Gly Ser Gly Gly Gly Gly
        50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Gly Ser Gly Gly Gly Gly Ser Gly
                85                  90                  95

Gly Gly Gly Ser
            100

<210> SEQ ID NO 106
<211> LENGTH: 208
<212> TYPE: PRT
<213> ORGANISM: Middle East respiratory syndrome-related coronavirus

<400> SEQUENCE: 106

Val Glu Cys Asp Phe Ser Pro Leu Leu Ser Gly Thr Pro Pro Gln Val
1               5                   10                  15

Tyr Asn Phe Lys Arg Leu Val Phe Thr Asn Cys Asn Tyr Asn Leu Thr
                20                  25                  30

Lys Leu Leu Ser Leu Phe Ser Val Asn Asp Phe Thr Cys Ser Gln Ile

```
                35                  40                  45
Ser Pro Ala Ile Ala Ser Asn Cys Tyr Ser Ser Leu Ile Leu Asp
 50                  55                  60

Tyr Phe Ser Tyr Pro Leu Ser Met Lys Ser Asp Leu Ser Val Ser
65                  70                  75                  80

Ala Gly Pro Ile Ser Gln Phe Asn Tyr Lys Gln Ser Phe Ser Asn Pro
                 85                  90                  95

Thr Cys Leu Ile Leu Ala Thr Val Pro His Asn Leu Thr Thr Ile Thr
                100                 105                 110

Lys Pro Leu Lys Tyr Ser Tyr Ile Asn Lys Cys Ser Arg Leu Leu Ser
                115                 120                 125

Asp Asp Arg Thr Glu Val Pro Gln Leu Val Asn Ala Asn Gln Tyr Ser
                130                 135                 140

Pro Cys Val Ser Ile Val Pro Ser Thr Val Trp Glu Asp Gly Asp Tyr
145                 150                 155                 160

Tyr Arg Lys Gln Leu Ser Pro Leu Glu Gly Gly Gly Trp Leu Val Ala
                165                 170                 175

Ser Gly Ser Thr Val Ala Met Thr Glu Gln Leu Gln Met Gly Phe Gly
                180                 185                 190

Ile Thr Val Gln Tyr Gly Thr Asp Thr Asn Ser Val Cys Pro Lys Leu
                195                 200                 205
```

<210> SEQ ID NO 107
<211> LENGTH: 200
<212> TYPE: PRT
<213> ORGANISM: Severe acute respiratory syndrome coronavirus 2

<400> SEQUENCE: 107

```
Arg Phe Pro Asn Ile Thr Asn Leu Cys Pro Phe Gly Glu Val Phe Asn
1               5                   10                  15

Ala Thr Arg Phe Ala Ser Val Tyr Ala Trp Asn Arg Lys Arg Ile Ser
                20                  25                  30

Asn Cys Val Ala Asp Tyr Ser Val Leu Tyr Asn Ser Ala Ser Phe Ser
                35                  40                  45

Thr Phe Lys Cys Tyr Gly Val Ser Pro Thr Lys Leu Asn Asp Leu Cys
 50                  55                  60

Phe Thr Asn Val Tyr Ala Asp Ser Phe Val Ile Arg Gly Asp Glu Val
65                  70                  75                  80

Arg Gln Ile Ala Pro Gly Gln Thr Gly Lys Ile Ala Asp Tyr Asn Tyr
                85                  90                  95

Lys Leu Pro Asp Asp Phe Thr Gly Cys Val Ile Ala Trp Asn Ser Asn
                100                 105                 110

Asn Leu Asp Ser Lys Val Gly Gly Asn Tyr Asn Tyr Leu Tyr Arg Leu
                115                 120                 125

Phe Arg Lys Ser Asn Leu Lys Pro Phe Glu Arg Asp Ile Ser Thr Glu
130                 135                 140

Ile Tyr Gln Ala Gly Ser Thr Pro Cys Asn Gly Val Glu Gly Phe Asn
145                 150                 155                 160

Cys Tyr Phe Pro Leu Gln Ser Tyr Gly Phe Gln Pro Thr Asn Gly Val
                165                 170                 175

Gly Tyr Gln Pro Tyr Arg Val Val Val Leu Ser Phe Glu Leu Leu His
                180                 185                 190

Ala Pro Ala Thr Val Cys Gly Pro
195                 200
```

<210> SEQ ID NO 108
<211> LENGTH: 202
<212> TYPE: PRT
<213> ORGANISM: Human SARS coronavirus

<400> SEQUENCE:

-continued

```
His Gly Lys Leu Arg Pro Phe Glu Arg Asp Ile Ser Asn Val Pro Phe
    130                 135                 140

Ser Pro Asp Gly Lys Pro Cys Thr Pro Pro Ala Phe Asn Cys Tyr Trp
145                 150                 155                 160

Pro Leu Asn Asp Tyr Gly Phe Phe Thr Thr Asn Gly Ile Gly Tyr Gln
                165                 170                 175

Pro Tyr Arg Val Val Val Leu Ser Phe Glu Leu Leu Asn Ala Pro Ala
                180                 185                 190

Thr Val Cys Gly Pro Lys Leu Ser Thr Asp
            195                 200
```